US007977047B2

(12) United States Patent
Cole et al.

(10) Patent No.: US 7,977,047 B2
(45) Date of Patent: Jul. 12, 2011

(54) **DELETE SEQUENCE IN *M. TUBERCULOSIS*, METHOD FOR DETECTING MYCOBACTERIA USING THESE SEQUENCES AND VACCINES**

(75) Inventors: Stewart Cole, Paris (FR); Roland Brosch, Paris (FR); Stephen Gordon, Surrey (GB); Karin Eiglmeier, Paris (FR); Thierry Garnier, Paris (FR); Glyn Hewinson, Hants (GB)

(73) Assignee: Institut Pasteur, Paris (FR)

( * ) Notice: Subject to any disclaimer, the term of this patent is extended or adjusted under 35 U.S.C. 154(b) by 590 days.

(21) Appl. No.: 10/505,405

(22) PCT Filed: Feb. 25, 2003

(86) PCT No.: PCT/IB03/00986

§ 371 (c)(1),
(2), (4) Date: Jan. 13, 2006

(87) PCT Pub. No.: WO03/070981

PCT Pub. Date: Aug. 28, 2003

(65) Prior Publication Data

US 2006/0127897 A1 Jun. 15, 2006

(30) Foreign Application Priority Data

Feb. 25, 2002 (EP) .................................... 02290458

(51) Int. Cl.
*C12Q 1/68* (2006.01)
*C12N 1/00* (2006.01)
*C12N 15/00* (2006.01)
*C07H 21/02* (2006.01)

(52) U.S. Cl. ......... 435/6; 435/243; 435/320.1; 536/23.1

(58) Field of Classification Search ........................ None
See application file for complete search history.

(56) References Cited

U.S. PATENT DOCUMENTS

| | | | | |
|---|---|---|---|---|
| 5,474,796 | A * | 12/1995 | Brennan | 427/2.13 |
| 6,221,353 | B1 * | 4/2001 | Laqueyrerie et al. | 424/168.1 |
| 6,291,190 | B1 | 9/2001 | Behr et al. | |
| 2001/0053519 | A1 * | 12/2001 | Fodor et al. | 435/6 |

FOREIGN PATENT DOCUMENTS

WO WO 00/55362 9/2000

OTHER PUBLICATIONS

New England Biolabs 1998/99 Catalog (NEB Catalog).*
GENBANK Accession No. L26330 (uploaded to NCBI Jun. 4, 1994).*
BLAST search completed @ NCBI on Aug. 13, 2008.*
NCBI (GENANK Accession No. U15183; Mar. 9, 1995).*
Santos et al. (J Med Microbiol. Oct. 1993;39(4):298-304).*
International Search Report in the corresponding PCT application No. PCT/IB03/009864 filed Mar. 13, 2003.
European Search Report in the corresponding European application No. EP 02 290 458.5, filed Feb. 24, 2002.
Cole et al., Deciphering the biology of *Mycobacterium tuberculosis* from the complete genome sequence, *Nature,* vol. 393, Jun. 11, 1998.
Cole et al., "Deciphering the biology of *Mycobacterium tuberculosis* from the complete genome sequence" *Database Genbank, NCBI,* whole document (Nature 393, 537-544 (1998)).
Mahairas et al., "Molecular Analysis of Genetic Differences between *Mycobacterium bovis* BCG and Virulent *M. bovis", Journal of Bacteriology,* vol. 178, No. 5, Mar. 1996, pp. 1274-1282, American Society for Microbiology.
Gordon et al., "Identification of variable regions in the genomes of tubercle bacilli using bacterial artificial chromosome arrays", *Molecular Microbiology* (1999) 32(3), pp. 643-655, 1999 Blackwell Science Ltd.
Sreevatsan et al., "Restricted structural gene polymorphism in the *Mycobacterium tuberculosis* complex indicates evolutionarily recent global dissemination", *Proc. Natl. Acad. Sci.* USA, vol. 94, pp. 9869-9874, Sep. 1997.
Brosch, R. et al., "A new evolutionary scenario for the *Mycobacterium tuberculosis* complex", *PNAS* vol. 99, No. 6, Mar. 19, 2002.
Brosch et al., "A new evolutionary scenario for the *Mycobacterium tuberculosis* complex", *Database GENBANK, NCBI,* whole document (PNAS 99(6) 3684-3689 (2002)).
Boddinghaus et al., "Detection and Identification of Mycobacteria by Amplification of rRNA", *Journal of Clinical Microbiology,* vol. 28, No. 8, Aug. 1990, pp. 1751-1759, American Society for Microbiology.
Sreevatsan et al., "Restricted structural gene polymorphism in the *Mycobacterium tuberculosis* complex indicates evolutionarily recent global dissemination", *Microbiology,* Proc. Natl. Acad. Sci. USA, vol. 94, pp. 9869-9874, Sep. 1997.
Stead et al., "When Did *Mycobacterium tuberculosis* Infection First Occur in the New World?", Am J Respir Crit Care Med, vol. 151, pp. 1267-1268, 1995.
Behr et al., "Comparative Genomics of BCG Vaccines by Whole-Genome DNA Microarray", Reports, *Science,* vol. 284, pp. 1520-1523, May 28, 1999.
Brosch et al., "Genomic Analysis Reveals Variation between *Mycobacterium tuberculosis* H37Rv and the Attenuated *M. tuberculosis* H37Ra Strain", *Infection and Immunity,* vol. 67, No. 11, Nov. 1999, pp. 5768-5774, American Society for Microbiology.
Kremer et al., "Comparison of Methods Based on Different Molecular Epidemiological Markers for Typing of *Mycobacterium tuberculosis* Complex Strains: Interlaboratory Study of Discriminatory Power and Reproducibility", *Journal of Clinical Microbiology,* vol. 37, No. 8, Aug. 1999, pp. 2607-2618.

(Continued)

*Primary Examiner* — Christopher M. Babic
(74) *Attorney, Agent, or Firm* — Finnegan, Henderson, Farabow, Garrett & Dunner, L.L.P.

(57) ABSTRACT

The present invention is the identification of a nucleotide sequence which make it possible in particular to distinguish an infection resulting from the vast majority of *Mycobacterium tuberculosis* strains from an infection resulting from *Mycobacterium africanum, Mycobacterium canetti, Mycobacterium microti, Mycobacterium bovis, Mycobacterium bovis* BCG. The subject of the present invention is also a method for detecting the sequences in question by the products of expression of these sequences and the kits for carrying out these methods. Finally, the subject of the present invention is novel vaccines.

20 Claims, 6 Drawing Sheets

OTHER PUBLICATIONS

Figure 1:
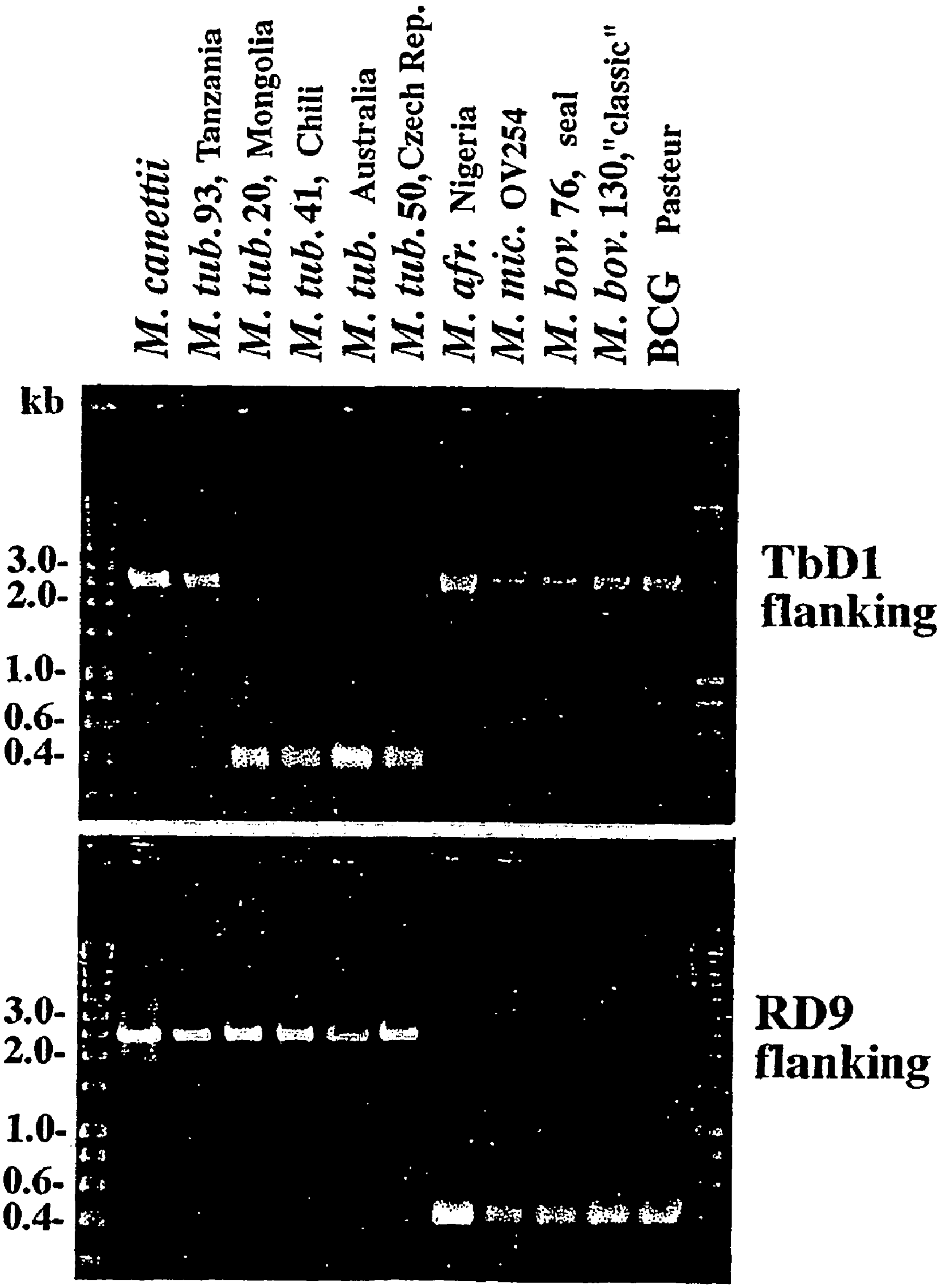

Supply et al., "Automated High-Throughput Genotyping for Study of Global Epidemiology of *Mycobacterium tuberculosis* Based on Mycrobacterial Interspersed Repetitive Units", Journal of Clinical *Microbiology,* vol. 39, No. 10, , pp. 3563-3571, Oct. 2001.

Van Soolingen et al., "DNA Fingerprinting of *Mycobacterium tuberculosis" Methods in Enzymology,* vol. 235, pp. 196-205, Academic Press, Inc. 1994.

Heym et al., "Implications of multidrug resistance for the future of short-course chemotherapy of tuberculosis: a molecular study", *The Lancet,* vol. 344, pp. 293-298, Jul. 30, 1994.

Scorpio et al., "Rapid Differentiation of Bovine and Human Tubercle Bacilli Based on a Characteristic Mutation in the Bovine Pyrazinamidase Gene", *Journal of Clinical Microbiology,* vol. 35, No. 1, pp. 106-110, Jan. 1997, American Society for Microbiology.

Sreevatsan et al., "Identification of a Polymorphic Nucleotide in *oxy*R Specific for *Mycobacterium bovis", Journal of Clinical Microbiology,* vol. 34, No. 8, pp. 2007-2010, Aug. 1996, American Society for Microbiology.

Van Embden et al., "Genetic Variation and Evolutionary Origin of the Direct Repeat Locus of *Mycobacterium tuberculosis* Complex Bacteria", *Journal of Bacteriology,* vol. 182, No. 9, pp. 2393-2401, May 2000, American Society for Microbiology.

Van Soolingen et al., "A Novel Pathogenic Taxon of the *Mycobacterium tuberculosis* Complex, Canetti: Characterization of an Exceptional Isolate from Africa", *International Journal of Systematic Bacteriology,* vol. 47, No. 4, pp. 1236-1245, Oct. 1997, International Union of Microbiological Societies.

Papa et al., "Serological Specificity of *Mycobacterium tuberculosis* Glycolipids", *ACTA Leprologica* (1989), vol. 7 (Suppl. 1), pp. 98-101.

Wells, A.Q., "Tuberculosis in Wild Voles", *The Lancet,* p. 1221, May 22, 1937.

Van Soolingen et al., "Diagnosis of *Myobacterium microti* Infections among Humans by Using Novel Genetic Markers", *Journal of Clinical Microbiology,* vol. 36, No. 7, pp. 1840-1845, Jul. 1998, American Society for Microbiology, 1998.

Brodin et al., "Bacterial Artificial Chromosome-Based Comparative Genomic Analysis Identifies *Mycobacterium microti* as a Natural ESAT-6 Deletion Mutant", *Infection and Immunity,* vol. 70, No. 10, pp. 5568-5578, Oct. 2002, American Society for Microbiology.

Aranaz et al., "*Mycobacterium tuberculosis* subsp. *Caprae* subsp. Nov.: a taxonomic study of a new member of the *Mycobacterium tuberculosis* complex isolated from goats in Spain", *International Journal of Systematic Bacteriology,* (1999), vol. 49, pp. 1263-1273, IUMS.

Van Soolingen et al., "Use of Various Genetic Markers in Differentiation of *Mycobacterium bovis* Strains from Animals and Humans and for Studying Epidemiology of Bovine Tuberculosis", *Journal of Clinical Microbiology,* vol. 32, No. 10, pp. 2425-2433, Oct. 1994.

Samper et al., "Transmission between HIV-infected patients of multidrug-resistant tuberculosis caused by *Mycobacterium bovis", Aids,* vol. 11, No. 10, pp. 1237-1242, 1997, Rapid Science Publishers.

Gordon, S.V. et al., Genomics of *Mycobacterium bovis, Tuberculosis* (2001), vol. 81(1/2), pp. 157-163, Harcourt Publishers Ltd.

Brosch et al., "Genomics, Biology, and Evolution of the *Mycobacterium tuberculosis* Complex", *Molecular Genetics of Mycobacteria,* pp. 19-36, ASM Press, 2000, Washington DC.

Fletcher et al., "Widespread Occurrence of *Mycobacterium tuberculosis* DNA from $18^{th}$-$19^{th}$ Century Hungarians", *American Journal of Physical Anthropology,* vol. 120, pp. 144-152 (2003), Wiley Liss, Inc. 2003.

Mays et al., "Paleopathological and Biomolecular Study of Tuberculosis in a Medieval Skeletal Collection from England", *American Journal of Physical Anthropology,* vol. 114, pp. 298-311 (2001), Wiley-Liss, Inc.

Salo et al., "Identification of *Mycobacterium tuberculosis* DNA in a pre-Columbian Peruvian mummy", *Microbiology,* Proc. Natl. Acad. Sci. USA, vol. 91, pp. 2091-2094, Mar. 1994.

Rothschild et al., "*Mycobacterium tuberculosis Complex* DNA from an Extinct Bison Dated 17,000 Years before the Present", *Clinical Infectious Diseases* 2001, vol. 33, pp. 305-311, Origins of Tuberculosis in North America, Aug. 1.

Parsons et al., "Rapid and Simple Approach for Identification of *Mycobacterium tuberculosis* Complex Isolates by PCR-Based Genomic Deletion Analysis", *Journal of Clinical Microbiology,* vol. 40, No. 7, pp. 2339-2345, Jul. 2002, American Society for Microbiology.

Eisenach et al., "Polymerase Chain Reaction Amplification of a Repetitive DNA Sequence Specific for *Mycobacterium tuberculiosis", The Journal of Infectious Diseases,* 1990, vol. 161, pp. 977-981, The University of Chicago, 1990.

Thierry et al., "Characterization of a *Mycobacterium tuberculosis* Insertion Sequence, IS6110, and Its Application in Diagnosis", *Journal of Clinical Microbiology,* vol. 28, No. 12, Dec. 1990, pp. 2668-2673, American Society for Microbiology.

Brisson-Noel et al., "Diagnosis of tuberculosis by DNA amplification in clinical practice evaluation", *The Lancet,* vol. 338, pp. 364-366, Aug. 10, 1991.

Clarridge III et al., "Large-Scale Use of Polymerase Chain Reaction for Detection of *Mycobacterium tuberculosis* in a Routine Mycobacteriology Laboratory", *Journal of Clinical Microbiology,* vol. 31, No. 8, pp. 2049-2056. Date : Aug. 1993.

Gormican et al., "Use of polymerase chain reaction for early identification of *Mycobacterium tuberculosis* in positive cultures", *J. Clin Pathol* 1992, vol. 45, pp. 601-604, Department of Medical Microbiology, University College Hospital, Galway, Ireland, Nov. 20, 1991.

Cousins et al., "Use of Polymerase Chain Reaction for Rapid Diagnosis of Tuberculosis", *Journal of Clinical Microbiology,* vol. 30, No. 1, Jan. 1992, pp. 255-258, American Society for Microbiology.

Del Portillo et al., Amplification of a Species-Specific DNA Fragment of *Mycobacterium tuberculosis* and Its Possible Use in Diagnosis *Journal of Clinical Microbiology,* vol. 29, No. 10, pp. 2163-2168, Oct. 1991, American Society for Microbiology.

Folgueira et al., "Polymerase chain reaction for rapid diagnosis of tuberculous meningitis in AIDS patients", *Neurology* 1994, vol. 44, pp. 1336-1338.

Forbes et al., "Direct Detection of *Mycobacterium tuberculosis* in Respiratory Specimens in a Clinical Laboratory by Polymerase Chain Reaction", *Journal of Clinical Microbiology,* vol. 31, No. 7, pp. 1688-1694, Jul. 1993, American Society for Microbiology.

Hermans et al., "Specific Detection of *Mycobacterium tuberculosis* Complex Strains by Polymerase Chain Reaction", *Journal of Clinical Microbiology,* vol. 28, No. 6, Jun. 1990, pp. 1204-1213, American Society for Microbiology.

Kaltwasser et al., "Enzymatic DNA amplification (PCR) in the diagnosis of extrapulmonary *Mycobacterium tuberculosis* infection", *Molecular and Cellular Probes* (1993) vol. 7, pp. 467-470, Academic Press Limited.

Kocagoz et al., "Detection of *Mycobacterium tuberculosis* in Sputum Samples by Polymerase Chain Reaction Using a Simplified Procedure", *Journal of Clinical Microbiology,* vol. 31, No. 6, pp. 1435-1438, Jun. 1993, American Society for Microbiology.

Kolk et al, "Detection of *Mycobacterium tuberculosis* in Clinical Samples by Using Polymerase Chain Reaction and a Nonradioactive Detection System", *Journal of Clinical Microbiology,* vol. 30, No. 10, pp. 2567-2575, Oct. 1992, American Society for Microbiology.

Kox et al., "A More Reliable PCR for detection of *Mycobactgerium tuberculosis* in Clinical Samples", *Journla of Clinical Microbiology,* vol. 32, No. 3, pp. 672-678, Mar. 1994, American Society for Microbiology.

Liu et al., "Rapid diagnosis of tuberculous meningitis by a simplified nested amplification protocol", *Neurology,* vol. 44, pp. 1161-1164, 1994.

Thierry et al., Characterization of a *Mycobacterium tuberculosis* Insertion Sequence. IS6110, and Its Application in Diagnosis, *Journal of Clinical Microbiology,* vol. 28, No. 12, pp. 2668-2673, American Society for Microbiology, Date: Dec. 1990.

Miller et al., "Evaluation of Gen-Probe Amplified *Mycobacterium tuberculosis* Direct Test and PCR for Direct Detection of

*Mycobacterium tuberculosis* in Clinical Specimens", *Journal of Clinical Microbiology,* vol. 32, No. 2, pp. 393-397, Feb. 1994, American Society for Microbiology.
Reischl, et al., "PCR-Based Detection of Mycobacteria in Sputum Samples Using a Simple and Reliable DNA Extraction Protocol", *Benchmarks,* vol. 17, No. 5 (1994), pp. 844-845.
Schluger et al., Clinical Utility of the Polymerase Chain Reaction in the Diagnosis of Infections due to *Mycobacterium tuberculosis,* Chest/105/4/Apr. 1994, pp. 1116-1121.
Shawar et al., "Detection of *Mycobacterium tuberculosis* in Clinical Samples by Two-Step Polymerase Chain Reaction and Nonisotopic Hybridization Methods", *Journal of Clinical Microbiology,* vol. 31, No. 1, pp. 61-65, Jan. 1993, American Society for Microbiology.
Urdea et al., "A Comparison of non-radioisotopic hybridization assay methods using fluorescent, chemilluminescent and enzyme labeled synthetic oligodeoxyribonucleotide probes", *Nucleic Acids Research,* vol. 16, No. 11, pp. 4937-4956, 1988.
Sanchez-Pescador et al., "Rapid Chemiluminescent Nucleic Acid Assays for Detection of TEM-1 β-Lactamase-Mediated Penicillin Resistance in *Neisseria gonorrhoeae* and Other Bacteria", *Journal of Clinical Microbiology,* vol. 26, No. 10, pp. 1934-1938, Oct. 1988, American Society for Microbiology.
Matthews et al., "Analytical Strategies for the Use of DNA Probes", Review, *Analytical Biochemistry,* vol. 169, pp. 1-25, 1988, Academic Press, Inc., 1988.
Schmidt, "Opening Remarks", *Reviews of Infectious Diseases,* vol. 11, Supp. 2, Mar.-Apr. 1989, Fogarty International Center, National Institutes of Health, Bethesda, Maryland.
Merlich et al., Molecular evidence for tuberculosis in an ancient Egyptian mummy, *The Lancet,* vol. 350, p. 1404, Nov. 8, 1997, Departments of Pathology, Anthropology, and Radiology, Ludwig-Maximillians-Universitat München, 80337 Germany.
Radhakrishnan et al, "Implications of Low Frequency of IS6110 in Fingerprinting Field Isolates of *Mycobacterium tuberculosis* from Kerala, India", *Journal of Clinical Microbiology,* vol. 39, No. 4, p. 1683, Apr. 2001, American Society for Microbiology, 2001.

* cited by examiner gatcccgtcg ccgcggcgct ggagctggcc gccgggcccg cagccgcccc gcgcgaggtc 60
gtgctggcga gcaaagccac catgcgcgcc acagccagcc ccggatcgct ggaccttgag 120
caacacgaac tcgccaaacg cttagaactt gggccgcagg cgaaatcggt ccagtcgccc 180
gagttcgccg ctcgcttggc tgccgctcaa cacaggtagc gcctaccagc ctcgctggtt 240
tccatggcgt gccccagtcc gaagctgctg ctgcttgact ccgcgcgctg ggcccgagcg 300
cgcgctgttg tacggcccaa acggcgtgtc ggtgtacagt cgcgcgctcg cggcttcagt 360
ccggcccccc gactccggca ggcccgacgg cgcccagcgc tagcccgaag ttccccttg 420
taggggcggg ctgagtttcg atctgtttcg tgagcaggtg tttctgtgtt caacttccct 480
caacatgtac tcatgtatta ttgagaatag ctcggcgtgt catcctctga tgacgctatt 540
atcgcgctga ccgcgtgtta taaagtaatc atgtacatta cccgggtacc caaccgggga 600
tccccgccgg cggtgctgtt gcgggaaagc ttccgcgaaa acggcaaggt caagacgcgt 660
accctggcca acctctcacg ctggcccgag cacaagctgg acagactgga ccgggcgctt 720
aagggcttgc cgcccgcgga ctgggatcta gccgaggcct tcgatatcac ccgcagcctg 780
ccgcacgggc atgtggccgc ggtggccggc accgccgaga agctgggcat acccgagctg 840
atcgacccca ccccgtcgcg gcggcgcaac ctggtgctgg ccatgctgat cgggcagatc 900
atcgagcccg gatcgaaact ggcgatcgcg cgcgggctgc gcgcccagac cgccaccagc 960
acgctgggtg cggtgctggg tgtctcgggc gccgatgagg acgacctgta tgacgcgatg 1020
gactgggcgc tggagcgcaa agacggcatc gaaaacgcct tggccgcacg gcatctgacc 1080
aacggcaccc tggtgctcta tgacgtatcc tcggcggcgt tcgagggcca cacctgcccg 1140
ctgggagcga tcgggcacgc ccgcgacggg gtcaaaggcc ggctgcagat cgtctacggg 1200
ctgctgtgct cacccaaggg agcgccggtg gccatcgagg tgttcaaggg caacaccgcc 1260
gacccgaaaa ctctgaaagc tcaaatcgac aagctcaaaa cccggttcgg gttgacccgc 1320
atcgccctgg tgggcgatcg gggcatgctc acttccgcgc gcatccgtga cgagctgcgt 1380
ccggcgcacc tggattggat cagcgcgctg cgcgccccgc agatcaagat cctgctcgag 1440
gacggggcgc tgcagctgtc gctgttcgat gagcagaacc tgttcgagat cactcacccc 1500
gactatcccg gtgagcggct ggtgtgctgc cacaaccccg ccctggccga cgagcgcgcc 1560
cgcaaacgcg ccgagctgct ggcggccacc gaaaaggagc tgcaggccat cgccgaagcc 1620
acccgccgcc aacgccggcc gttacgcggt acagacaaga tcggcctgcg ggtgggcaag 1680
gtgcgcaaca agttcaagat ggccaagcac tttgacctgc acatcaccga tgaggccttc 1740
agcttcaccc gcaaccagaa cagtatcgcc gccgaggccg ccctcgacgg catctacgtg 1800
ctacgcacca gcctgcccga caacgccctg ggccgcgacg acgtggtggg ccgctacaaa 1860
gacctcgccg acgtcgaacg cttcttccgc accctcaaca gcgaactgga cgtacgcccc 1920
atccggcatc ggctggccga ccgggtccgc gcccacatgt tcttgcacat gctctcctac 1980
tacatcagct ggcacatgaa acaagccctg gccccaatcc tgttcaccga caacgacaaa 2040
cccgccgccg ccgccaaacg cgccgacccc gtcgcgccag cccaacgctc cgacgaagcg 2100
ctgaacaagg cagcacgcaa acgcaccgaa gacaaccaac cggtgcacag cttcaccagc 2160
ctgctcaccg acctggccac catctgcgcc aactacatcc aacccacaga cgacctgcca 2220
gcattcacca aaaccaccac ccccaccccc acacaacggc gcgccttcga cctactggcc 2280
gtttcccacc gccacggcct ggcgtagtca gtaccgaacc acaaatgccc aggtcaacga 2340
cacaaaccgc gccggatcag ggggaacttc gggctagccg ggcgcgccgg 2390

Figure 6

SEQUENCE LISTING

```
<160> NUMBER OF SEQ ID NOS: 117

<210> SEQ ID NO 1
<211> LENGTH: 3953
<212> TYPE: DNA
<213> ORGANISM: Mycobacterium tuberculosis
<220> FEATURE:
<221> NAME/KEY: CDS
<222> LOCATION: (735)..(3638)

<400> SEQUENCE: 1

tccagcgcgg ccatcagcga tgaactctgg gacctgctac ccggctacct catcttccgg      60

tccatcatcc ccaaccggcc gcccacccag gacacggtgc aagccctcgt cgacgacgtg     120

atactcccca gcctcacccg atccaccggt tgagtcagcg gtgcgaatgg ctgggcaccg     180

ttgtggtgtc cggtcccgta ccgtactgtt gaatccgcgg atccccgcct gaggtacggg     240

gcgtggtcgc gccccgggca atagcgtcgc cggttatcga aaggctaacg ggtgcagggg     300

atttcagtga ctggcctggt caaacgcggc tggatggtgc tggttgccgt ggcggtggtg     360

gcggtcgcgg gattcagcgt ctatcggttg cacggcatct tcggctcgca cgacaccacc     420

tcgaccgccg gtggtgtcgc gaacgacatc aagccgttca accccaaaca ggtaaccctc     480

gaggtctttg gcgctcccgg aaccgtggca acgatcaatt atctggacgt ggatgccaca     540

cctcggcaag tcctggacac gaccctgccg tggtcataca cgatcacgac gaccctgccc     600

gcggtcttcg ccaatgttgt cgcgcaaggc gacagcaatt ccatcggctg ccgcatcacc     660

gtcaacggtg tagtcaagga cgaaaggatc gtcaacgaag tgcgcgccta taccttctgc     720

ctcgacaagt cctc atg agc aac cac cac cgc ccg cgg cct tgg ttg ccg       770
                Met Ser Asn His His Arg Pro Arg Pro Trp Leu Pro
                1               5                   10

cac acc atc cga cgg ctt tcg ttg ccg atc ttg ctg ttt tgg gtg ggt       818
His Thr Ile Arg Arg Leu Ser Leu Pro Ile Leu Leu Phe Trp Val Gly
        15                  20                  25

gtg gcc gcc ata acc aat gcc gcc gtg ccg caa ttg gag gtg gtc ggg       866
Val Ala Ala Ile Thr Asn Ala Ala Val Pro Gln Leu Glu Val Val Gly
    30                  35                  40

gag gcg cat aac gtc gca cag agc tcc ccg gat gac ccg tcg ctg cag       914
Glu Ala His Asn Val Ala Gln Ser Ser Pro Asp Asp Pro Ser Leu Gln
45                  50                  55                  60

gcg atg aaa cgc atc ggc aag gtg ttc cac gag ttc gat tcc gac agt       962
Ala Met Lys Arg Ile Gly Lys Val Phe His Glu Phe Asp Ser Asp Ser
                65                  70                  75

gcg gcc atg atc gtc ttg gaa ggc gat aag ccg ctc ggc aac gac gcc      1010
Ala Ala Met Ile Val Leu Glu Gly Asp Lys Pro Leu Gly Asn Asp Ala
            80                  85                  90

cac cgg ttc tac gac acc ctg ctc cgc aac ctt tca aac gac acc aaa      1058
His Arg Phe Tyr Asp Thr Leu Leu Arg Asn Leu Ser Asn Asp Thr Lys
        95                  100                 105

cac gtc gag cac gtt cag gac ttc tgg ggc gat ccg ctg acc gcg gcc      1106
His Val Glu His Val Gln Asp Phe Trp Gly Asp Pro Leu Thr Ala Ala
```

-continued

```
    110                 115                 120

ggc tcg caa agc acc gac ggc aaa gcc gcc tac gtt cag gtc tat ctc      1154
Gly Ser Gln Ser Thr Asp Gly Lys Ala Ala Tyr Val Gln Val Tyr Leu
125                 130                 135                 140

gcc ggc aac caa ggc gag gcg ttg tca atc gag tcc gtc gac gcg gtg      1202
Ala Gly Asn Gln Gly Glu Ala Leu Ser Ile Glu Ser Val Asp Ala Val
                145                 150                 155

cgc gac atc gtc gcc cat acg cca cca ccg gcc ggg gtc aag gcc tac      1250
Arg Asp Ile Val Ala His Thr Pro Pro Pro Ala Gly Val Lys Ala Tyr
            160                 165                 170

gtc acc ggc gcg gcc ccg ctc atg gcc gat cag ttt cag gtg ggc agc      1298
Val Thr Gly Ala Ala Pro Leu Met Ala Asp Gln Phe Gln Val Gly Ser
        175                 180                 185

aaa gga acc gcg aaa gtt acc ggg ata act ctg gtt gtg atc gcg gtg      1346
Lys Gly Thr Ala Lys Val Thr Gly Ile Thr Leu Val Val Ile Ala Val
    190                 195                 200

atg ttg ctc ttc gta tac cgt tcc gtc gtc acc atg gtc ctg gtg ctt      1394
Met Leu Leu Phe Val Tyr Arg Ser Val Val Thr Met Val Leu Val Leu
205                 210                 215                 220

atc acg gtt ctt att gag ttg gcc gcg gcc cgc ggg atc gtc gct ttt      1442
Ile Thr Val Leu Ile Glu Leu Ala Ala Ala Arg Gly Ile Val Ala Phe
                225                 230                 235

ctc gga aac gcc ggg gta atc ggg ctg tcg aca tac tcg acg aat ctg      1490
Leu Gly Asn Ala Gly Val Ile Gly Leu Ser Thr Tyr Ser Thr Asn Leu
            240                 245                 250

ctc aca cta ttg gta atc gcg gcg ggc aca gac tac gcg att ttt gtc      1538
Leu Thr Leu Leu Val Ile Ala Ala Gly Thr Asp Tyr Ala Ile Phe Val
        255                 260                 265

ctc ggc cgc tat cac gag gcg cgc tac gcc gca cag gat cgg gaa acg      1586
Leu Gly Arg Tyr His Glu Ala Arg Tyr Ala Ala Gln Asp Arg Glu Thr
    270                 275                 280

gcc ttc tac acg atg tat cgc ggg acc gcc cac gtc gtc ttg ggc tcg      1634
Ala Phe Tyr Thr Met Tyr Arg Gly Thr Ala His Val Val Leu Gly Ser
285                 290                 295                 300

ggt ctg acc gtt gcc ggc gcg gtg tat tgc ctg agc ttt acc cgg cta      1682
Gly Leu Thr Val Ala Gly Ala Val Tyr Cys Leu Ser Phe Thr Arg Leu
                305                 310                 315

ccc tat ttt caa agc ctg ggt att ccc gcc tcg ata ggg gtg atg att      1730
Pro Tyr Phe Gln Ser Leu Gly Ile Pro Ala Ser Ile Gly Val Met Ile
            320                 325                 330

gcg ttg gca gcc gcg ctc agc ctg gcc cca tcc gtg ctc atc ttg ggc      1778
Ala Leu Ala Ala Ala Leu Ser Leu Ala Pro Ser Val Leu Ile Leu Gly
        335                 340                 345

agt cgt ttc ggt tgt ttc gaa ccc aag cgc agg atg agg acc agg gga      1826
Ser Arg Phe Gly Cys Phe Glu Pro Lys Arg Arg Met Arg Thr Arg Gly
    350                 355                 360

tgg cgg cgc atc ggc acg gcc atc gtg cgt tgg ccg gga ccc atc ctg      1874
Trp Arg Arg Ile Gly Thr Ala Ile Val Arg Trp Pro Gly Pro Ile Leu
365                 370                 375                 380

gca gtg gcg tgc gca att gcg gtg gtg ggt ctg ctc gcg ctg ccg gga      1922
Ala Val Ala Cys Ala Ile Ala Val Val Gly Leu Leu Ala Leu Pro Gly
                385                 390                 395

tac aaa acg agc tac gac gct cgc tat tac atg ccc gcc acc gcc ccg      1970
Tyr Lys Thr Ser Tyr Asp Ala Arg Tyr Tyr Met Pro Ala Thr Ala Pro
            400                 405                 410

gcc aat att ggc tac atg gcc gcg gag cga cat ttt ccc caa gcg cgg      2018
Ala Asn Ile Gly Tyr Met Ala Ala Glu Arg His Phe Pro Gln Ala Arg
        415                 420                 425

ctg aat ccc gaa cta ctg atg atc gag acg gat cac gat atg cgc aat      2066
Leu Asn Pro Glu Leu Leu Met Ile Glu Thr Asp His Asp Met Arg Asn
```

-continued

```
    430                 435                 440

ccg gcc gac atg ctc atc ttg gat agg atc gcc aag gct gtc ttc cat      2114
Pro Ala Asp Met Leu Ile Leu Asp Arg Ile Ala Lys Ala Val Phe His
445                 450                 455                 460

ctg ccc ggc ata ggg ctg gtg cag gcc atg acc cgg ccg cta gga acc      2162
Leu Pro Gly Ile Gly Leu Val Gln Ala Met Thr Arg Pro Leu Gly Thr
                465                 470                 475

ccg att gac cac agc tcg ata ccg ttt cag atc agc atg caa agc gtc      2210
Pro Ile Asp His Ser Ser Ile Pro Phe Gln Ile Ser Met Gln Ser Val
            480                 485                 490

ggc cag att cag aat ctc aag tat cag agg gac cga gca gcc gac ttg      2258
Gly Gln Ile Gln Asn Leu Lys Tyr Gln Arg Asp Arg Ala Ala Asp Leu
        495                 500                 505

ctg aag cag gcc gaa gag ctg ggg aag acg atc gaa atc ttg cag cgc      2306
Leu Lys Gln Ala Glu Glu Leu Gly Lys Thr Ile Glu Ile Leu Gln Arg
    510                 515                 520

caa tat gcc cta cag cag gaa ctc gcg gcc gct act cac gag caa gcc      2354
Gln Tyr Ala Leu Gln Gln Glu Leu Ala Ala Ala Thr His Glu Gln Ala
525                 530                 535                 540

gaa agc ttt cac caa acg atc gcc acg gta aac gaa ctg cga gat agg      2402
Glu Ser Phe His Gln Thr Ile Ala Thr Val Asn Glu Leu Arg Asp Arg
                545                 550                 555

atc gcc aat ttc gac gat ttc ttc agg ccg att cgt agt tac ttt tac      2450
Ile Ala Asn Phe Asp Asp Phe Phe Arg Pro Ile Arg Ser Tyr Phe Tyr
            560                 565                 570

tgg gaa aag cac tgc tac gat atc ccg agc tgc tgg gcg ctg aga tcc      2498
Trp Glu Lys His Cys Tyr Asp Ile Pro Ser Cys Trp Ala Leu Arg Ser
        575                 580                 585

gtc ttt gac acg atc gac ggt atc gac caa ctc ggc gag cag ctg gcc      2546
Val Phe Asp Thr Ile Asp Gly Ile Asp Gln Leu Gly Glu Gln Leu Ala
    590                 595                 600

agc gtg acc gta acc ttg gac aag ttg gct gcg atc cag cct caa ttg      2594
Ser Val Thr Val Thr Leu Asp Lys Leu Ala Ala Ile Gln Pro Gln Leu
605                 610                 615                 620

gtg gcg ctg cta cca gac gag atc gcc agc cag cag atc aat cgg gaa      2642
Val Ala Leu Leu Pro Asp Glu Ile Ala Ser Gln Gln Ile Asn Arg Glu
                625                 630                 635

ctg gcg ctg gct aac tac gcc acc atg tcc ggg atc tat gcc cag acg      2690
Leu Ala Leu Ala Asn Tyr Ala Thr Met Ser Gly Ile Tyr Ala Gln Thr
            640                 645                 650

gcg gcc ttg atc gaa aac gct gcc gcc atg gga caa gcc ttt gac gcc      2738
Ala Ala Leu Ile Glu Asn Ala Ala Ala Met Gly Gln Ala Phe Asp Ala
        655                 660                 665

gcc aag aac gac gac tcc ttc tat ctg ccg ccg gag gct ttt gac aac      2786
Ala Lys Asn Asp Asp Ser Phe Tyr Leu Pro Pro Glu Ala Phe Asp Asn
    670                 675                 680

cca gat ttc cag cgc ggc ctg aaa ttg ttc ctg tcg gca gac ggt aag      2834
Pro Asp Phe Gln Arg Gly Leu Lys Leu Phe Leu Ser Ala Asp Gly Lys
685                 690                 695                 700

gcg gct cgg atg atc atc tcc cat gaa ggc gat ccc gcc acc ccc gaa      2882
Ala Ala Arg Met Ile Ile Ser His Glu Gly Asp Pro Ala Thr Pro Glu
                705                 710                 715

ggc att tcg cat atc gac gcg atc aag cag gcg gcc cac gag gcc gtg      2930
Gly Ile Ser His Ile Asp Ala Ile Lys Gln Ala Ala His Glu Ala Val
            720                 725                 730

aag ggc act ccc atg gcg ggt gct ggg atc tat ctg gcc ggc acg gcc      2978
Lys Gly Thr Pro Met Ala Gly Ala Gly Ile Tyr Leu Ala Gly Thr Ala
        735                 740                 745

gcc acc ttc aag gac att caa gac ggc gcc acc tac gac ctc ctg atc      3026
Ala Thr Phe Lys Asp Ile Gln Asp Gly Ala Thr Tyr Asp Leu Leu Ile
```

```
    750                 755                 760

gcc gga ata gcc gcg ctg agc ttg att ttg ctc atc atg atg atc att     3074
Ala Gly Ile Ala Ala Leu Ser Leu Ile Leu Leu Ile Met Met Ile Ile
765                 770                 775                 780

acc cga agc ctg gtt gcg gcg ctg gtg atc gtg ggc acg gtg gcg ctg     3122
Thr Arg Ser Leu Val Ala Ala Leu Val Ile Val Gly Thr Val Ala Leu
                785                 790                 795

tcg ttg ggc gct tct ttt ggc ctg tcc gtg ctg gtg tgg cag cat ctt     3170
Ser Leu Gly Ala Ser Phe Gly Leu Ser Val Leu Val Trp Gln His Leu
            800                 805                 810

ctc ggt atc cag ttg tac tgg atc gtg ctc gcg ctg gcc gtc atc ctg     3218
Leu Gly Ile Gln Leu Tyr Trp Ile Val Leu Ala Leu Ala Val Ile Leu
        815                 820                 825

ctc ctg gcc gtg gga tcg gac tat aac ttg ctg ctg att tcc cga ttc     3266
Leu Leu Ala Val Gly Ser Asp Tyr Asn Leu Leu Leu Ile Ser Arg Phe
    830                 835                 840

aag gag gag atc ggt gca ggt ttg aac acc ggc atc atc cgt gcg atg     3314
Lys Glu Glu Ile Gly Ala Gly Leu Asn Thr Gly Ile Ile Arg Ala Met
845                 850                 855                 860

gcc ggc acc ggc ggg gtg gtg acc gct gcc ggc ctg gtg ttc gcc gcc     3362
Ala Gly Thr Gly Gly Val Val Thr Ala Ala Gly Leu Val Phe Ala Ala
                865                 870                 875

act atg tct tcg ttc gtg ttc agt gat ttg cgg gtc ctc ggt cag atc     3410
Thr Met Ser Ser Phe Val Phe Ser Asp Leu Arg Val Leu Gly Gln Ile
            880                 885                 890

ggg acc acc att ggt ctt ggg ctg ctg ttc gac acg ctg gtg gtg cgc     3458
Gly Thr Thr Ile Gly Leu Gly Leu Leu Phe Asp Thr Leu Val Val Arg
        895                 900                 905

gcg ttc atg acc ccg tcc atc gcg gtg ctg ctc ggg cgc tgg ttc tgg     3506
Ala Phe Met Thr Pro Ser Ile Ala Val Leu Leu Gly Arg Trp Phe Trp
    910                 915                 920

tgg ccg caa cga gtg cgc ccg cgc cct gcc agc agg atg ctt cgg ccg     3554
Trp Pro Gln Arg Val Arg Pro Arg Pro Ala Ser Arg Met Leu Arg Pro
925                 930                 935                 940

tac ggc ccg cgg ccc gtg gtt cgt gaa ttg ctg ctg cgc gag ggc aac     3602
Tyr Gly Pro Arg Pro Val Val Arg Glu Leu Leu Leu Arg Glu Gly Asn
                945                 950                 955

gat gac ccg aga act cag gtg gct acc cac cgt taa ggtggtggga          3648
Asp Asp Pro Arg Thr Gln Val Ala Thr His Arg
            960                 965

tgccgctttc aggggaatat gcgccgagcc cgctcgactg gtcgcgcgag caagccgaca   3708

cgtatatgaa gtccggcgga accgagggca cacagctgca gggaaagccg gtcatcctgc   3768

tcaccaccgt cggggcgaag accggcaaac tccgtaagac cccgctgatg cgcgtcgagc   3828

acgacggcca gtacgcgatc gtcgcctcgc tgggtggggc gccgaaaaat ccggtctggt   3888

accacaacgt cgtgaagaac ccacgggtcg agctgcagga cggcaccgga ccggcgacta   3948

cgacg                                                               3953
```

<210> SEQ ID NO 2
<211> LENGTH: 967
<212> TYPE: PRT
<213> ORGANISM: Mycobacterium tuberculosis

<400> SEQUENCE: 2

```
Met Ser Asn His His Arg Pro Arg Pro Trp Leu Pro His Thr Ile Arg
1               5                   10                  15

Arg Leu Ser Leu Pro Ile Leu Leu Phe Trp Val Gly Val Ala Ala Ile
            20                  25                  30
```

-continued

```
Thr Asn Ala Ala Val Pro Gln Leu Glu Val Val Gly Glu Ala His Asn
        35                  40                  45

Val Ala Gln Ser Ser Pro Asp Asp Pro Ser Leu Gln Ala Met Lys Arg
    50                  55                  60

Ile Gly Lys Val Phe His Glu Phe Asp Ser Asp Ser Ala Ala Met Ile
65                  70                  75                  80

Val Leu Glu Gly Asp Lys Pro Leu Gly Asn Asp Ala His Arg Phe Tyr
                85                  90                  95

Asp Thr Leu Leu Arg Asn Leu Ser Asn Asp Thr Lys His Val Glu His
            100                 105                 110

Val Gln Asp Phe Trp Gly Asp Pro Leu Thr Ala Ala Gly Ser Gln Ser
        115                 120                 125

Thr Asp Gly Lys Ala Ala Tyr Val Gln Val Tyr Leu Ala Gly Asn Gln
    130                 135                 140

Gly Glu Ala Leu Ser Ile Glu Ser Val Asp Ala Val Arg Asp Ile Val
145                 150                 155                 160

Ala His Thr Pro Pro Pro Ala Gly Val Lys Ala Tyr Val Thr Gly Ala
                165                 170                 175

Ala Pro Leu Met Ala Asp Gln Phe Gln Val Gly Ser Lys Gly Thr Ala
            180                 185                 190

Lys Val Thr Gly Ile Thr Leu Val Val Ile Ala Val Met Leu Leu Phe
        195                 200                 205

Val Tyr Arg Ser Val Val Thr Met Val Leu Val Leu Ile Thr Val Leu
    210                 215                 220

Ile Glu Leu Ala Ala Ala Arg Gly Ile Val Ala Phe Leu Gly Asn Ala
225                 230                 235                 240

Gly Val Ile Gly Leu Ser Thr Tyr Ser Thr Asn Leu Leu Thr Leu Leu
                245                 250                 255

Val Ile Ala Ala Gly Thr Asp Tyr Ala Ile Phe Val Leu Gly Arg Tyr
            260                 265                 270

His Glu Ala Arg Tyr Ala Ala Gln Asp Arg Glu Thr Ala Phe Tyr Thr
        275                 280                 285

Met Tyr Arg Gly Thr Ala His Val Val Leu Gly Ser Gly Leu Thr Val
    290                 295                 300

Ala Gly Ala Val Tyr Cys Leu Ser Phe Thr Arg Leu Pro Tyr Phe Gln
305                 310                 315                 320

Ser Leu Gly Ile Pro Ala Ser Ile Gly Val Met Ile Ala Leu Ala Ala
                325                 330                 335

Ala Leu Ser Leu Ala Pro Ser Val Leu Ile Leu Gly Ser Arg Phe Gly
            340                 345                 350

Cys Phe Glu Pro Lys Arg Arg Met Arg Thr Arg Gly Trp Arg Arg Ile
        355                 360                 365

Gly Thr Ala Ile Val Arg Trp Pro Gly Pro Ile Leu Ala Val Ala Cys
    370                 375                 380

Ala Ile Ala Val Val Gly Leu Leu Ala Leu Pro Gly Tyr Lys Thr Ser
385                 390                 395                 400

Tyr Asp Ala Arg Tyr Tyr Met Pro Ala Thr Ala Pro Ala Asn Ile Gly
                405                 410                 415

Tyr Met Ala Ala Glu Arg His Phe Pro Gln Ala Arg Leu Asn Pro Glu
            420                 425                 430

Leu Leu Met Ile Glu Thr Asp His Asp Met Arg Asn Pro Ala Asp Met
        435                 440                 445

Leu Ile Leu Asp Arg Ile Ala Lys Ala Val Phe His Leu Pro Gly Ile
    450                 455                 460
```

```
Gly Leu Val Gln Ala Met Thr Arg Pro Leu Gly Thr Pro Ile Asp His
465                 470                 475                 480

Ser Ser Ile Pro Phe Gln Ile Ser Met Gln Ser Val Gly Gln Ile Gln
                485                 490                 495

Asn Leu Lys Tyr Gln Arg Asp Arg Ala Ala Asp Leu Leu Lys Gln Ala
            500                 505                 510

Glu Glu Leu Gly Lys Thr Ile Glu Ile Leu Gln Arg Gln Tyr Ala Leu
        515                 520                 525

Gln Gln Glu Leu Ala Ala Ala Thr His Glu Gln Ala Glu Ser Phe His
    530                 535                 540

Gln Thr Ile Ala Thr Val Asn Glu Leu Arg Asp Arg Ile Ala Asn Phe
545                 550                 555                 560

Asp Asp Phe Phe Arg Pro Ile Arg Ser Tyr Phe Tyr Trp Glu Lys His
                565                 570                 575

Cys Tyr Asp Ile Pro Ser Cys Trp Ala Leu Arg Ser Val Phe Asp Thr
            580                 585                 590

Ile Asp Gly Ile Asp Gln Leu Gly Glu Gln Leu Ala Ser Val Thr Val
        595                 600                 605

Thr Leu Asp Lys Leu Ala Ala Ile Gln Pro Gln Leu Val Ala Leu Leu
    610                 615                 620

Pro Asp Glu Ile Ala Ser Gln Gln Ile Asn Arg Glu Leu Ala Leu Ala
625                 630                 635                 640

Asn Tyr Ala Thr Met Ser Gly Ile Tyr Ala Gln Thr Ala Ala Leu Ile
                645                 650                 655

Glu Asn Ala Ala Ala Met Gly Gln Ala Phe Asp Ala Ala Lys Asn Asp
            660                 665                 670

Asp Ser Phe Tyr Leu Pro Pro Glu Ala Phe Asp Asn Pro Asp Phe Gln
        675                 680                 685

Arg Gly Leu Lys Leu Phe Leu Ser Ala Asp Gly Lys Ala Ala Arg Met
    690                 695                 700

Ile Ile Ser His Glu Gly Asp Pro Ala Thr Pro Glu Gly Ile Ser His
705                 710                 715                 720

Ile Asp Ala Ile Lys Gln Ala Ala His Glu Ala Val Lys Gly Thr Pro
                725                 730                 735

Met Ala Gly Ala Gly Ile Tyr Leu Ala Gly Thr Ala Ala Thr Phe Lys
            740                 745                 750

Asp Ile Gln Asp Gly Ala Thr Tyr Asp Leu Leu Ile Ala Gly Ile Ala
        755                 760                 765

Ala Leu Ser Leu Ile Leu Leu Ile Met Met Ile Ile Thr Arg Ser Leu
    770                 775                 780

Val Ala Ala Leu Val Ile Val Gly Thr Val Ala Leu Ser Leu Gly Ala
785                 790                 795                 800

Ser Phe Gly Leu Ser Val Leu Val Trp Gln His Leu Leu Gly Ile Gln
                805                 810                 815

Leu Tyr Trp Ile Val Leu Ala Leu Ala Val Ile Leu Leu Leu Ala Val
            820                 825                 830

Gly Ser Asp Tyr Asn Leu Leu Leu Ile Ser Arg Phe Lys Glu Glu Ile
        835                 840                 845

Gly Ala Gly Leu Asn Thr Gly Ile Ile Arg Ala Met Ala Gly Thr Gly
    850                 855                 860

Gly Val Val Thr Ala Ala Gly Leu Val Phe Ala Ala Thr Met Ser Ser
865                 870                 875                 880

Phe Val Phe Ser Asp Leu Arg Val Leu Gly Gln Ile Gly Thr Thr Ile
```

-continued

```
                885                 890                 895

Gly Leu Gly Leu Leu Phe Asp Thr Leu Val Val Arg Ala Phe Met Thr
            900                 905                 910

Pro Ser Ile Ala Val Leu Leu Gly Arg Trp Phe Trp Trp Pro Gln Arg
        915                 920                 925

Val Arg Pro Arg Pro Ala Ser Arg Met Leu Arg Pro Tyr Gly Pro Arg
    930                 935                 940

Pro Val Val Arg Glu Leu Leu Leu Arg Glu Gly Asn Asp Asp Pro Arg
945                 950                 955                 960

Thr Gln Val Ala Thr His Arg
                965


<210> SEQ ID NO 3
<211> LENGTH: 148
<212> TYPE: PRT
<213> ORGANISM: Mycobacterium tuberculosis

<400> SEQUENCE: 3

Val Gln Gly Ile Ser Val Thr Gly Leu Val Lys Arg Gly Trp Met Val
1               5                   10                  15

Leu Val Ala Val Ala Val Val Ala Val Ala Gly Phe Ser Val Tyr Arg
            20                  25                  30

Leu His Gly Ile Phe Gly Ser His Asp Thr Thr Ser Thr Ala Gly Gly
        35                  40                  45

Val Ala Asn Asp Ile Lys Pro Phe Asn Pro Lys Gln Val Thr Leu Glu
    50                  55                  60

Val Phe Gly Ala Pro Gly Thr Val Ala Thr Ile Asn Tyr Leu Asp Val
65                  70                  75                  80

Asp Ala Thr Pro Arg Gln Val Leu Asp Thr Thr Leu Pro Trp Ser Tyr
                85                  90                  95

Thr Ile Thr Thr Thr Leu Pro Ala Val Phe Ala Asn Val Val Ala Gln
            100                 105                 110

Gly Asp Ser Asn Ser Ile Gly Cys Arg Ile Thr Val Asn Gly Val Val
        115                 120                 125

Lys Asp Glu Arg Ile Val Asn Glu Val Arg Ala Tyr Thr Phe Cys Leu
    130                 135                 140

Asp Lys Ser Ser
145


<210> SEQ ID NO 4
<211> LENGTH: 2153
<212> TYPE: DNA
<213> ORGANISM: Mycobacterium tuberculosis

<400> SEQUENCE: 4

ctggttgccg tggcggtggt ggcggtcgcg ggattcagcg tctatcggtt gcacggcatc      60

ttcggctcgc acgacaccac ctcgaccgcc ggtggtgtcg cgaacgacat caagccgttc     120

aaccccaaac aggtaaccct cgaggtcttt ggcgctcccg gaaccgtggc aacgatcaat     180

tatctggacg tggatgccac acctcggcaa gtcctggaca cgaccctgcc gtggtcatac     240

acgatcacga cgaccctgcc cgcggtcttc gccaatgttg tcgcgcaagg cgacagcaat     300

tccatcggct gccgcatcac cgtcaacggt gtagtcaagg acgaaaggat cgtcaacgaa     360

gtgcgcgcct ataccttctg cctcgacaag tcctcatgag caaccaccac cgcccgcggc     420

cttggttgcc gcacaccatc cgacggcttt cgttgccgat cttgctgttt tgggtgggtg     480

tggccgccat aaccaatgcc gccgtgccgc aattggaggt ggtcggggag gcgcataacg     540
```

```
tcgcacagag ctccccggat gacccgtcgc tgcaggcgat gaaacgcatc ggcaaggtgt    600
tccacgagtt cgattccgac agtgcggcca tgatcgtctt ggaaggcgat aagccgctcg    660
gcaacgacgc ccaccggttc tacgacaccc tgctccgcaa cctttcaaac gacaccaaac    720
acgtcgagca cgttcaggac ttctggggcg atccgctgac cgcggccggc tcgcaaagca    780
ccgacggcaa agccgcctac gttcaggtct atctcgccgg caaccaaggc gaggcgttgt    840
caatcgagtc cgtcgacgcg gtgcgcgaca tcgtcgccca tacgccacca ccggccgggg    900
tcaaggccta cgtcaccggc gcggccccgc tcatggccga tcagtttcag gtgggcagca    960
aaggaaccgc gaaagttacc gggataactc tggttgtgat cgcggtgatg ttgctcttcg   1020
tataccgttc cgtcgtcacc atggtcctgg tgcttatcac ggttcttatt gagttggccg   1080
cggcccgcgg gatcgtcgct ttctcggaa acgccggggt aatcgggctg tcgacatact   1140
cgacgaatct gctcacacta ttggtaatcg cggcgggcac agactacgcg atttttgtcc   1200
tcggccgcta tcacgaggcg cgctacgccg cacaggatcg ggaaacggcc ttctacacga   1260
tgtatcgcgg gaccgcccac gtcgtcttgg gctcgggtct gaccgttgcc ggcgcggtgt   1320
attgcctgag ctttacccgg ctaccctatt ttcaaagcct gggtattccc gcctcgatag   1380
gggtgatgat tgcgttggca gccgcgctca gcctggcccc atccgtgctc atcttgggca   1440
gtcgtttcgg ttgtttcgaa cccaagcgca ggatgaggac caggggatgg cggcgcatcg   1500
gcacggccat cgtgcgttgg ccgggaccca tcctggcagt ggcgtgcgca attgcggtgg   1560
tgggtctgct cgcgctgccg ggatacaaaa cgagctacga cgctcgctat tacatgcccg   1620
ccaccgcccc ggccaatatt ggctacatgg ccgcggagcg acattttccc caagcgcggc   1680
tgaatcccga actactgatg atcgagacgg atcacgatat gcgcaatccg gccgacatgc   1740
tcatcttgga taggatcgcc aaggctgtct tccatctgcc cggcataggg ctggtgcagg   1800
ccatgacccg gccgctagga accccgattg accacagctc gataccgttt cagatcagca   1860
tgcaaagcgt cggccagatt cagaatctca agtatcagag ggaccgagca gccgacttgc   1920
tgaagcaggc cgaagagctg ggaagacga tcgaaatctt gcagcgccaa tatgccctac   1980
agcaggaact cgcggccgct actcacgagc aagccgaaag ctttcaccaa acgatcgcca   2040
cggtaaacga actgcgagat aggatcgcca atttcgacga tttcttcagg ccgattcgta   2100
gttactttta ctgggaaaag cactgctacg atatcccgag ctgctgggcg ctg          2153
```

<210> SEQ ID NO 5
<211> LENGTH: 2904
<212> TYPE: DNA
<213> ORGANISM: Mycobacterium complex
<220> FEATURE:
<221> NAME/KEY: CDS
<222> LOCATION: (1)..(2901)

<400> SEQUENCE: 5

```
atg agc aac cac cac cgc ccg cgg cct tgg ttg ccg cac acc atc cga       48
Met Ser Asn His His Arg Pro Arg Pro Trp Leu Pro His Thr Ile Arg
1               5                   10                  15

cgg ctt tcg ttg ccg atc ttg ctg ttt tgg gtg ggt gtg gcc gcc ata       96
Arg Leu Ser Leu Pro Ile Leu Leu Phe Trp Val Gly Val Ala Ala Ile
            20                  25                  30

acc aat gcc gcc gtg ccg caa ttg gag gtg gtc ggg gag gcg cat aac      144
Thr Asn Ala Ala Val Pro Gln Leu Glu Val Val Gly Glu Ala His Asn
        35                  40                  45

gtc gca cag agc tcc ccg gat gac ccg tcg ctg cag gcg atg aaa cgc      192
Val Ala Gln Ser Ser Pro Asp Asp Pro Ser Leu Gln Ala Met Lys Arg
```

-continued

```
    50                  55                  60

atc ggc aag gtg ttc cac gag ttc gat tcc gac agt gcg gcc atg atc       240
Ile Gly Lys Val Phe His Glu Phe Asp Ser Asp Ser Ala Ala Met Ile
65                  70                  75                  80

gtc ttg gaa ggc gat aag ccg ctc ggc aac gac gcc cac cgg ttc tac       288
Val Leu Glu Gly Asp Lys Pro Leu Gly Asn Asp Ala His Arg Phe Tyr
                85                  90                  95

gac acc ctg ctc cgc aac ctt tca aac gac acc aaa cac gtc gag cac       336
Asp Thr Leu Leu Arg Asn Leu Ser Asn Asp Thr Lys His Val Glu His
            100                 105                 110

gtt cag gac ttc tgg ggc gat ccg ctg acc gcg gcc ggc tcg caa agc       384
Val Gln Asp Phe Trp Gly Asp Pro Leu Thr Ala Ala Gly Ser Gln Ser
        115                 120                 125

acc gac ggc aaa gcc gcc tac gtt cag gtc tat ctc gcc ggc aac caa       432
Thr Asp Gly Lys Ala Ala Tyr Val Gln Val Tyr Leu Ala Gly Asn Gln
    130                 135                 140

ggc gag gcg ttg tca atc gag tcc gtc gac gcg gtg cgc gac atc gtc       480
Gly Glu Ala Leu Ser Ile Glu Ser Val Asp Ala Val Arg Asp Ile Val
145                 150                 155                 160

gcc cat acg cca cca ccg gcc ggg gtc aag gcc tac gtc acc ggc gcg       528
Ala His Thr Pro Pro Pro Ala Gly Val Lys Ala Tyr Val Thr Gly Ala
                165                 170                 175

gcc ccg ctc atg gcc gat cag ttt cag gtg ggc agc aaa gga acc gcg       576
Ala Pro Leu Met Ala Asp Gln Phe Gln Val Gly Ser Lys Gly Thr Ala
            180                 185                 190

aaa gtt acc ggg ata act ctg gtt gtg atc gcg gtg atg ttg ctc ttc       624
Lys Val Thr Gly Ile Thr Leu Val Val Ile Ala Val Met Leu Leu Phe
        195                 200                 205

gta tac cgt tcc gtc gtc acc atg gtc ctg gtg ctt atc acg gtt ctt       672
Val Tyr Arg Ser Val Val Thr Met Val Leu Val Leu Ile Thr Val Leu
    210                 215                 220

att gag ttg gcc gcg gcc cgc ggg atc gtc gct ttt ctc gga aac gcc       720
Ile Glu Leu Ala Ala Ala Arg Gly Ile Val Ala Phe Leu Gly Asn Ala
225                 230                 235                 240

ggg gta atc ggg ctg tcg aca tac tcg acg aat ctg ctc aca cta ttg       768
Gly Val Ile Gly Leu Ser Thr Tyr Ser Thr Asn Leu Leu Thr Leu Leu
                245                 250                 255

gta atc gcg gcg ggc aca gac tac gcg att ttt gtc ctc ggc cgc tat       816
Val Ile Ala Ala Gly Thr Asp Tyr Ala Ile Phe Val Leu Gly Arg Tyr
            260                 265                 270

cac gag gcg cgc tac gcc gca cag gat cgg gaa acg gcc ttc tac acg       864
His Glu Ala Arg Tyr Ala Ala Gln Asp Arg Glu Thr Ala Phe Tyr Thr
        275                 280                 285

atg tat cgc ggg acc gcc cac gtc gtc ttg ggc tcg ggt ctg acc gtt       912
Met Tyr Arg Gly Thr Ala His Val Val Leu Gly Ser Gly Leu Thr Val
    290                 295                 300

gcc ggc gcg gtg tat tgc ctg agc ttt acc cgg cta ccc tat ttt caa       960
Ala Gly Ala Val Tyr Cys Leu Ser Phe Thr Arg Leu Pro Tyr Phe Gln
305                 310                 315                 320

agc ctg ggt att ccc gcc tcg ata ggg gtg atg att gcg ttg gca gcc      1008
Ser Leu Gly Ile Pro Ala Ser Ile Gly Val Met Ile Ala Leu Ala Ala
                325                 330                 335

gcg ctc agc ctg gcc cca tcc gtg ctc atc ttg ggc agt cgt ttc ggt      1056
Ala Leu Ser Leu Ala Pro Ser Val Leu Ile Leu Gly Ser Arg Phe Gly
            340                 345                 350

tgt ttc gaa ccc aag cgc agg atg agg acc agg gga tgg cgg cgc atc      1104
Cys Phe Glu Pro Lys Arg Arg Met Arg Thr Arg Gly Trp Arg Arg Ile
        355                 360                 365

ggc acg gcc atc gtg cgt tgg ccg gga ccc atc ctg gca gtg gcg tgc      1152
Gly Thr Ala Ile Val Arg Trp Pro Gly Pro Ile Leu Ala Val Ala Cys
```

-continued

```
    370                 375                 380

gca att gcg gtg gtg ggt ctg ctc gcg ctg ccg gga tac aaa acg agc     1200
Ala Ile Ala Val Val Gly Leu Leu Ala Leu Pro Gly Tyr Lys Thr Ser
385                 390                 395                 400

tac gac gct cgc tat tac atg ccc gcc acc gcc ccg gcc aat att ggc     1248
Tyr Asp Ala Arg Tyr Tyr Met Pro Ala Thr Ala Pro Ala Asn Ile Gly
                405                 410                 415

tac atg gcc gcg gag cga cat ttt ccc caa gcg cgg ctg aat ccc gaa     1296
Tyr Met Ala Ala Glu Arg His Phe Pro Gln Ala Arg Leu Asn Pro Glu
            420                 425                 430

cta ctg atg atc gag acg gat cac gat atg cgc aat ccg gcc gac atg     1344
Leu Leu Met Ile Glu Thr Asp His Asp Met Arg Asn Pro Ala Asp Met
        435                 440                 445

ctc atc ttg gat agg atc gcc aag gct gtc ttc cat ctg ccc ggc ata     1392
Leu Ile Leu Asp Arg Ile Ala Lys Ala Val Phe His Leu Pro Gly Ile
    450                 455                 460

ggg ctg gtg cag gcc atg acc cgg ccg cta gga acc ccg att gac cac     1440
Gly Leu Val Gln Ala Met Thr Arg Pro Leu Gly Thr Pro Ile Asp His
465                 470                 475                 480

agc tcg ata ccg ttt cag atc agc atg caa agc gtc ggc cag att cag     1488
Ser Ser Ile Pro Phe Gln Ile Ser Met Gln Ser Val Gly Gln Ile Gln
                485                 490                 495

aat ctc aag tat cag agg gac cga gca gcc gac ttg ctg aag cag gcc     1536
Asn Leu Lys Tyr Gln Arg Asp Arg Ala Ala Asp Leu Leu Lys Gln Ala
            500                 505                 510

gaa gag ctg ggg aag acg atc gaa atc ttg cag cgc caa tat gcc cta     1584
Glu Glu Leu Gly Lys Thr Ile Glu Ile Leu Gln Arg Gln Tyr Ala Leu
        515                 520                 525

cag cag gaa ctc gcg gcc gct act cac gag caa gcc gaa agc ttt cac     1632
Gln Gln Glu Leu Ala Ala Ala Thr His Glu Gln Ala Glu Ser Phe His
    530                 535                 540

caa acg atc gcc acg gta aag gaa ctg cga gat agg atc gcc aat ttc     1680
Gln Thr Ile Ala Thr Val Lys Glu Leu Arg Asp Arg Ile Ala Asn Phe
545                 550                 555                 560

gac gat ttc ttc agg ccg att cgt agt tac ttt tac tgg gaa aag cac     1728
Asp Asp Phe Phe Arg Pro Ile Arg Ser Tyr Phe Tyr Trp Glu Lys His
                565                 570                 575

tgc tac gat atc ccg agc tgc tgg gcg ctg aga tcc gtc ttt gac acg     1776
Cys Tyr Asp Ile Pro Ser Cys Trp Ala Leu Arg Ser Val Phe Asp Thr
            580                 585                 590

atc gac ggt atc gac caa ctc ggc gag cag ctg gcc agc gtg acc gta     1824
Ile Asp Gly Ile Asp Gln Leu Gly Glu Gln Leu Ala Ser Val Thr Val
        595                 600                 605

acc ttg gac aag ttg gct gcg atc cag cct caa ttg gtg gcg ctg cta     1872
Thr Leu Asp Lys Leu Ala Ala Ile Gln Pro Gln Leu Val Ala Leu Leu
    610                 615                 620

cca gac gag atc gcc agc cag cag atc aat cgg gaa ctg gcg ctg gct     1920
Pro Asp Glu Ile Ala Ser Gln Gln Ile Asn Arg Glu Leu Ala Leu Ala
625                 630                 635                 640

aac tac gcc acc atg tcc ggg atc tat gcc cag acg gcg gcc ttg atc     1968
Asn Tyr Ala Thr Met Ser Gly Ile Tyr Ala Gln Thr Ala Ala Leu Ile
                645                 650                 655

gaa aac gct gcc gcc atg gga caa gcc ttt gac gcc gcc aag aac gac     2016
Glu Asn Ala Ala Ala Met Gly Gln Ala Phe Asp Ala Ala Lys Asn Asp
            660                 665                 670

gac tcc ttc tat ctg ccg ccg gag gct ttt gac aac cca gat ttc cag     2064
Asp Ser Phe Tyr Leu Pro Pro Glu Ala Phe Asp Asn Pro Asp Phe Gln
        675                 680                 685

cgc ggc ctg aaa ttg ttc ctg tcg gca gac ggt aag gcg gct cgg atg     2112
Arg Gly Leu Lys Leu Phe Leu Ser Ala Asp Gly Lys Ala Ala Arg Met
```

-continued

```
    690                 695                 700

atc atc tcc cat gaa ggc gat ccc gcc acc ccc gaa ggc att tcg cat      2160
Ile Ile Ser His Glu Gly Asp Pro Ala Thr Pro Glu Gly Ile Ser His
705                 710                 715                 720

atc gac gcg atc aag cag gcg gcc cac gag gcc gtg aag ggc act ccc      2208
Ile Asp Ala Ile Lys Gln Ala Ala His Glu Ala Val Lys Gly Thr Pro
                725                 730                 735

atg gcg ggt gct ggg atc tat ctg gcc ggc acg gcc gcc acc ttc aag      2256
Met Ala Gly Ala Gly Ile Tyr Leu Ala Gly Thr Ala Ala Thr Phe Lys
            740                 745                 750

gac att caa gac ggc gcc acc tac gac ctc ctg atc gcc gga ata gcc      2304
Asp Ile Gln Asp Gly Ala Thr Tyr Asp Leu Leu Ile Ala Gly Ile Ala
        755                 760                 765

gcg ctg agc ttg att ttg ctc atc atg atg atc att acc cga agc ctg      2352
Ala Leu Ser Leu Ile Leu Leu Ile Met Met Ile Ile Thr Arg Ser Leu
    770                 775                 780

gtt gcg gcg ctg gtg atc gtg ggc acg gtg gcg ctg tcg ttg ggc gct      2400
Val Ala Ala Leu Val Ile Val Gly Thr Val Ala Leu Ser Leu Gly Ala
785                 790                 795                 800

tct ttt ggc ctg tcc gtg ctg gtg tgg cag cat ctt ctc ggt atc cag      2448
Ser Phe Gly Leu Ser Val Leu Val Trp Gln His Leu Leu Gly Ile Gln
                805                 810                 815

ttg tac tgg atc gtg ctc gcg ctg gcc gtc atc ctg ctc ctg gcc gtg      2496
Leu Tyr Trp Ile Val Leu Ala Leu Ala Val Ile Leu Leu Leu Ala Val
            820                 825                 830

gga tcg gac tat aac ttg ctg ctg att tcc cga ttc aag gag gag atc      2544
Gly Ser Asp Tyr Asn Leu Leu Leu Ile Ser Arg Phe Lys Glu Glu Ile
        835                 840                 845

ggt gca ggt ttg aac acc ggc atc atc cgt gcg atg gcc ggc acc ggc      2592
Gly Ala Gly Leu Asn Thr Gly Ile Ile Arg Ala Met Ala Gly Thr Gly
    850                 855                 860

ggg gtg gtg acc gct gcc ggc ctg gtg ttc gcc gcc act atg tct tcg      2640
Gly Val Val Thr Ala Ala Gly Leu Val Phe Ala Ala Thr Met Ser Ser
865                 870                 875                 880

ttc gtg ttc agt gat ttg cgg gtc ctc ggt cag atc ggg acc acc att      2688
Phe Val Phe Ser Asp Leu Arg Val Leu Gly Gln Ile Gly Thr Thr Ile
                885                 890                 895

ggt ctt ggg ctg ctg ttc gac acg ctg gtg gtg cgc gcg ttc atg acc      2736
Gly Leu Gly Leu Leu Phe Asp Thr Leu Val Val Arg Ala Phe Met Thr
            900                 905                 910

ccg tcc atc gcg gtg ctg ctc ggg cgc tgg ttc tgg tgg ccg caa cga      2784
Pro Ser Ile Ala Val Leu Leu Gly Arg Trp Phe Trp Trp Pro Gln Arg
        915                 920                 925

gtg cgc ccg cgc cct gcc agc agg atg ctt cgg ccg tac ggc ccg cgg      2832
Val Arg Pro Arg Pro Ala Ser Arg Met Leu Arg Pro Tyr Gly Pro Arg
    930                 935                 940

ccc gtg gtt cgt gaa ttg ctg ctg cgc gag ggc aac gat gac ccg aga      2880
Pro Val Val Arg Glu Leu Leu Leu Arg Glu Gly Asn Asp Asp Pro Arg
945                 950                 955                 960

act cag gtg gct acc cac cgt taa                                      2904
Thr Gln Val Ala Thr His Arg
                965

<210> SEQ ID NO 6
<211> LENGTH: 967
<212> TYPE: PRT
<213> ORGANISM: Mycobacterium complex

<400> SEQUENCE: 6

Met Ser Asn His His Arg Pro Arg Pro Trp Leu Pro His Thr Ile Arg
1               5                   10                  15
```

-continued

```
Arg Leu Ser Leu Pro Ile Leu Leu Phe Trp Val Gly Val Ala Ala Ile
            20                  25                  30

Thr Asn Ala Ala Val Pro Gln Leu Glu Val Val Gly Glu Ala His Asn
        35                  40                  45

Val Ala Gln Ser Ser Pro Asp Asp Pro Ser Leu Gln Ala Met Lys Arg
    50                  55                  60

Ile Gly Lys Val Phe His Glu Phe Asp Ser Asp Ser Ala Ala Met Ile
65                  70                  75                  80

Val Leu Glu Gly Asp Lys Pro Leu Gly Asn Asp Ala His Arg Phe Tyr
                85                  90                  95

Asp Thr Leu Leu Arg Asn Leu Ser Asn Asp Thr Lys His Val Glu His
            100                 105                 110

Val Gln Asp Phe Trp Gly Asp Pro Leu Thr Ala Ala Gly Ser Gln Ser
        115                 120                 125

Thr Asp Gly Lys Ala Ala Tyr Val Gln Val Tyr Leu Ala Gly Asn Gln
    130                 135                 140

Gly Glu Ala Leu Ser Ile Glu Ser Val Asp Ala Val Arg Asp Ile Val
145                 150                 155                 160

Ala His Thr Pro Pro Pro Ala Gly Val Lys Ala Tyr Val Thr Gly Ala
                165                 170                 175

Ala Pro Leu Met Ala Asp Gln Phe Gln Val Gly Ser Lys Gly Thr Ala
            180                 185                 190

Lys Val Thr Gly Ile Thr Leu Val Val Ile Ala Val Met Leu Leu Phe
        195                 200                 205

Val Tyr Arg Ser Val Val Thr Met Val Leu Val Leu Ile Thr Val Leu
    210                 215                 220

Ile Glu Leu Ala Ala Ala Arg Gly Ile Val Ala Phe Leu Gly Asn Ala
225                 230                 235                 240

Gly Val Ile Gly Leu Ser Thr Tyr Ser Thr Asn Leu Leu Thr Leu Leu
                245                 250                 255

Val Ile Ala Ala Gly Thr Asp Tyr Ala Ile Phe Val Leu Gly Arg Tyr
            260                 265                 270

His Glu Ala Arg Tyr Ala Ala Gln Asp Arg Glu Thr Ala Phe Tyr Thr
        275                 280                 285

Met Tyr Arg Gly Thr Ala His Val Val Leu Gly Ser Gly Leu Thr Val
    290                 295                 300

Ala Gly Ala Val Tyr Cys Leu Ser Phe Thr Arg Leu Pro Tyr Phe Gln
305                 310                 315                 320

Ser Leu Gly Ile Pro Ala Ser Ile Gly Val Met Ile Ala Leu Ala Ala
                325                 330                 335

Ala Leu Ser Leu Ala Pro Ser Val Leu Ile Leu Gly Ser Arg Phe Gly
            340                 345                 350

Cys Phe Glu Pro Lys Arg Arg Met Arg Thr Arg Gly Trp Arg Arg Ile
        355                 360                 365

Gly Thr Ala Ile Val Arg Trp Pro Gly Pro Ile Leu Ala Val Ala Cys
    370                 375                 380

Ala Ile Ala Val Val Gly Leu Leu Ala Leu Pro Gly Tyr Lys Thr Ser
385                 390                 395                 400

Tyr Asp Ala Arg Tyr Tyr Met Pro Ala Thr Ala Pro Ala Asn Ile Gly
                405                 410                 415

Tyr Met Ala Ala Glu Arg His Phe Pro Gln Ala Arg Leu Asn Pro Glu
            420                 425                 430

Leu Leu Met Ile Glu Thr Asp His Asp Met Arg Asn Pro Ala Asp Met
```

-continued

```
        435                 440                 445

Leu Ile Leu Asp Arg Ile Ala Lys Ala Val Phe His Leu Pro Gly Ile
    450                 455                 460

Gly Leu Val Gln Ala Met Thr Arg Pro Leu Gly Thr Pro Ile Asp His
465                 470                 475                 480

Ser Ser Ile Pro Phe Gln Ile Ser Met Gln Ser Val Gly Gln Ile Gln
                485                 490                 495

Asn Leu Lys Tyr Gln Arg Asp Arg Ala Ala Asp Leu Leu Lys Gln Ala
            500                 505                 510

Glu Glu Leu Gly Lys Thr Ile Glu Ile Leu Gln Arg Gln Tyr Ala Leu
        515                 520                 525

Gln Gln Glu Leu Ala Ala Ala Thr His Glu Gln Ala Glu Ser Phe His
    530                 535                 540

Gln Thr Ile Ala Thr Val Lys Glu Leu Arg Asp Arg Ile Ala Asn Phe
545                 550                 555                 560

Asp Asp Phe Phe Arg Pro Ile Arg Ser Tyr Phe Tyr Trp Glu Lys His
                565                 570                 575

Cys Tyr Asp Ile Pro Ser Cys Trp Ala Leu Arg Ser Val Phe Asp Thr
            580                 585                 590

Ile Asp Gly Ile Asp Gln Leu Gly Glu Gln Leu Ala Ser Val Thr Val
        595                 600                 605

Thr Leu Asp Lys Leu Ala Ala Ile Gln Pro Gln Leu Val Ala Leu Leu
    610                 615                 620

Pro Asp Glu Ile Ala Ser Gln Gln Ile Asn Arg Glu Leu Ala Leu Ala
625                 630                 635                 640

Asn Tyr Ala Thr Met Ser Gly Ile Tyr Ala Gln Thr Ala Ala Leu Ile
                645                 650                 655

Glu Asn Ala Ala Ala Met Gly Gln Ala Phe Asp Ala Ala Lys Asn Asp
            660                 665                 670

Asp Ser Phe Tyr Leu Pro Pro Glu Ala Phe Asp Asn Pro Asp Phe Gln
        675                 680                 685

Arg Gly Leu Lys Leu Phe Leu Ser Ala Asp Gly Lys Ala Ala Arg Met
    690                 695                 700

Ile Ile Ser His Glu Gly Asp Pro Ala Thr Pro Glu Gly Ile Ser His
705                 710                 715                 720

Ile Asp Ala Ile Lys Gln Ala Ala His Glu Ala Val Lys Gly Thr Pro
                725                 730                 735

Met Ala Gly Ala Gly Ile Tyr Leu Ala Gly Thr Ala Ala Thr Phe Lys
            740                 745                 750

Asp Ile Gln Asp Gly Ala Thr Tyr Asp Leu Leu Ile Ala Gly Ile Ala
        755                 760                 765

Ala Leu Ser Leu Ile Leu Leu Ile Met Met Ile Ile Thr Arg Ser Leu
    770                 775                 780

Val Ala Ala Leu Val Ile Val Gly Thr Val Ala Leu Ser Leu Gly Ala
785                 790                 795                 800

Ser Phe Gly Leu Ser Val Leu Val Trp Gln His Leu Leu Gly Ile Gln
                805                 810                 815

Leu Tyr Trp Ile Val Leu Ala Leu Ala Val Ile Leu Leu Leu Ala Val
            820                 825                 830

Gly Ser Asp Tyr Asn Leu Leu Leu Ile Ser Arg Phe Lys Glu Glu Ile
        835                 840                 845

Gly Ala Gly Leu Asn Thr Gly Ile Ile Arg Ala Met Ala Gly Thr Gly
    850                 855                 860
```

```
Gly Val Val Thr Ala Ala Gly Leu Val Phe Ala Ala Thr Met Ser Ser
865                 870                 875                 880

Phe Val Phe Ser Asp Leu Arg Val Leu Gly Gln Ile Gly Thr Thr Ile
                885                 890                 895

Gly Leu Gly Leu Leu Phe Asp Thr Leu Val Val Arg Ala Phe Met Thr
            900                 905                 910

Pro Ser Ile Ala Val Leu Leu Gly Arg Trp Phe Trp Trp Pro Gln Arg
        915                 920                 925

Val Arg Pro Arg Pro Ala Ser Arg Met Leu Arg Pro Tyr Gly Pro Arg
    930                 935                 940

Pro Val Val Arg Glu Leu Leu Leu Arg Glu Gly Asn Asp Asp Pro Arg
945                 950                 955                 960

Thr Gln Val Ala Thr His Arg
                965


<210> SEQ ID NO 7
<211> LENGTH: 1758
<212> TYPE: DNA
<213> ORGANISM: Mycobacterium complex
<220> FEATURE:
<221> NAME/KEY: CDS
<222> LOCATION: (1)..(1758)

<400> SEQUENCE: 7

atg agc aac cac cac cgc ccg cgg cct tgg ttg ccg cac acc atc cga       48
Met Ser Asn His His Arg Pro Arg Pro Trp Leu Pro His Thr Ile Arg
1               5                   10                  15

cgg ctt tcg ttg ccg atc ttg ctg ttt tgg gtg ggt gtg gcc gcc ata       96
Arg Leu Ser Leu Pro Ile Leu Leu Phe Trp Val Gly Val Ala Ala Ile
            20                  25                  30

acc aat gcc gcc gtg ccg caa ttg gag gtg gtc ggg gag gcg cat aac      144
Thr Asn Ala Ala Val Pro Gln Leu Glu Val Val Gly Glu Ala His Asn
        35                  40                  45

gtc gca cag agc tcc ccg gat gac ccg tcg ctg cag gcg atg aaa cgc      192
Val Ala Gln Ser Ser Pro Asp Asp Pro Ser Leu Gln Ala Met Lys Arg
    50                  55                  60

atc ggc aag gtg ttc cac gag ttc gat tcc gac agt gcg gcc atg atc      240
Ile Gly Lys Val Phe His Glu Phe Asp Ser Asp Ser Ala Ala Met Ile
65                  70                  75                  80

gtc ttg gaa ggc gat aag ccg ctc ggc aac gac gcc cac cgg ttc tac      288
Val Leu Glu Gly Asp Lys Pro Leu Gly Asn Asp Ala His Arg Phe Tyr
                85                  90                  95

gac acc ctg ctc cgc aac ctt tca aac gac acc aaa cac gtc gag cac      336
Asp Thr Leu Leu Arg Asn Leu Ser Asn Asp Thr Lys His Val Glu His
            100                 105                 110

gtt cag gac ttc tgg ggc gat ccg ctg acc gcg gcc ggc tcg caa agc      384
Val Gln Asp Phe Trp Gly Asp Pro Leu Thr Ala Ala Gly Ser Gln Ser
        115                 120                 125

acc gac ggc aaa gcc gcc tac gtt cag gtc tat ctc gcc ggc aac caa      432
Thr Asp Gly Lys Ala Ala Tyr Val Gln Val Tyr Leu Ala Gly Asn Gln
    130                 135                 140

ggc gag gcg ttg tca atc gag tcc gtc gac gcg gtg cgc gac atc gtc      480
Gly Glu Ala Leu Ser Ile Glu Ser Val Asp Ala Val Arg Asp Ile Val
145                 150                 155                 160

gcc cat acg cca cca ccg gcc ggg gtc aag gcc tac gtc acc ggc gcg      528
Ala His Thr Pro Pro Pro Ala Gly Val Lys Ala Tyr Val Thr Gly Ala
                165                 170                 175

gcc ccg ctc atg gcc gat cag ttt cag gtg ggc agc aaa gga acc gcg      576
Ala Pro Leu Met Ala Asp Gln Phe Gln Val Gly Ser Lys Gly Thr Ala
            180                 185                 190
```

-continued

```
aaa gtt acc ggg ata act ctg gtt gtg atc gcg gtg atg ttg ctc ttc      624
Lys Val Thr Gly Ile Thr Leu Val Val Ile Ala Val Met Leu Leu Phe
        195                 200                 205

gta tac cgt tcc gtc gtc acc atg gtc ctg gtg ctt atc acg gtt ctt      672
Val Tyr Arg Ser Val Val Thr Met Val Leu Val Leu Ile Thr Val Leu
    210                 215                 220

att gag ttg gcc gcg gcc cgc ggg atc gtc gct ttt ctc gga aac gcc      720
Ile Glu Leu Ala Ala Ala Arg Gly Ile Val Ala Phe Leu Gly Asn Ala
225                 230                 235                 240

ggg gta atc ggg ctg tcg aca tac tcg acg aat ctg ctc aca cta ttg      768
Gly Val Ile Gly Leu Ser Thr Tyr Ser Thr Asn Leu Leu Thr Leu Leu
                245                 250                 255

gta atc gcg gcg ggc aca gac tac gcg att ttt gtc ctc ggc cgc tat      816
Val Ile Ala Ala Gly Thr Asp Tyr Ala Ile Phe Val Leu Gly Arg Tyr
            260                 265                 270

cac gag gcg cgc tac gcc gca cag gat cgg gaa acg gcc ttc tac acg      864
His Glu Ala Arg Tyr Ala Ala Gln Asp Arg Glu Thr Ala Phe Tyr Thr
        275                 280                 285

atg tat cgc ggg acc gcc cac gtc gtc ttg ggc tcg ggt ctg acc gtt      912
Met Tyr Arg Gly Thr Ala His Val Val Leu Gly Ser Gly Leu Thr Val
    290                 295                 300

gcc ggc gcg gtg tat tgc ctg agc ttt acc cgg cta ccc tat ttt caa      960
Ala Gly Ala Val Tyr Cys Leu Ser Phe Thr Arg Leu Pro Tyr Phe Gln
305                 310                 315                 320

agc ctg ggt att ccc gcc tcg ata ggg gtg atg att gcg ttg gca gcc     1008
Ser Leu Gly Ile Pro Ala Ser Ile Gly Val Met Ile Ala Leu Ala Ala
                325                 330                 335

gcg ctc agc ctg gcc cca tcc gtg ctc atc ttg ggc agt cgt ttc ggt     1056
Ala Leu Ser Leu Ala Pro Ser Val Leu Ile Leu Gly Ser Arg Phe Gly
            340                 345                 350

tgt ttc gaa ccc aag cgc agg atg agg acc agg gga tgg cgg cgc atc     1104
Cys Phe Glu Pro Lys Arg Arg Met Arg Thr Arg Gly Trp Arg Arg Ile
        355                 360                 365

ggc acg gcc atc gtg cgt tgg ccg gga ccc atc ctg gca gtg gcg tgc     1152
Gly Thr Ala Ile Val Arg Trp Pro Gly Pro Ile Leu Ala Val Ala Cys
    370                 375                 380

gca att gcg gtg gtg ggt ctg ctc gcg ctg ccg gga tac aaa acg agc     1200
Ala Ile Ala Val Val Gly Leu Leu Ala Leu Pro Gly Tyr Lys Thr Ser
385                 390                 395                 400

tac gac gct cgc tat tac atg ccc gcc acc gcc ccg gcc aat att ggc     1248
Tyr Asp Ala Arg Tyr Tyr Met Pro Ala Thr Ala Pro Ala Asn Ile Gly
                405                 410                 415

tac atg gcc gcg gag cga cat ttt ccc caa gcg cgg ctg aat ccc gaa     1296
Tyr Met Ala Ala Glu Arg His Phe Pro Gln Ala Arg Leu Asn Pro Glu
            420                 425                 430

cta ctg atg atc gag acg gat cac gat atg cgc aat ccg gcc gac atg     1344
Leu Leu Met Ile Glu Thr Asp His Asp Met Arg Asn Pro Ala Asp Met
        435                 440                 445

ctc atc ttg gat agg atc gcc aag gct gtc ttc cat ctg ccc ggc ata     1392
Leu Ile Leu Asp Arg Ile Ala Lys Ala Val Phe His Leu Pro Gly Ile
    450                 455                 460

ggg ctg gtg cag gcc atg acc cgg ccg cta gga acc ccg att gac cac     1440
Gly Leu Val Gln Ala Met Thr Arg Pro Leu Gly Thr Pro Ile Asp His
465                 470                 475                 480

agc tcg ata ccg ttt cag atc agc atg caa agc gtc ggc cag att cag     1488
Ser Ser Ile Pro Phe Gln Ile Ser Met Gln Ser Val Gly Gln Ile Gln
                485                 490                 495

aat ctc aag tat cag agg gac cga gca gcc gac ttg ctg aag cag gcc     1536
Asn Leu Lys Tyr Gln Arg Asp Arg Ala Ala Asp Leu Leu Lys Gln Ala
            500                 505                 510
```

```
gaa gag ctg ggg aag acg atc gaa atc ttg cag cgc caa tat gcc cta      1584
Glu Glu Leu Gly Lys Thr Ile Glu Ile Leu Gln Arg Gln Tyr Ala Leu
        515                 520                 525

cag cag gaa ctc gcg gcc gct act cac gag caa gcc gaa agc ttt cac      1632
Gln Gln Glu Leu Ala Ala Ala Thr His Glu Gln Ala Glu Ser Phe His
    530                 535                 540

caa acg atc gcc acg gta aag gaa ctg cga gat agg atc gcc aat ttc      1680
Gln Thr Ile Ala Thr Val Lys Glu Leu Arg Asp Arg Ile Ala Asn Phe
545                 550                 555                 560

gac gat ttc ttc agg ccg att cgt agt tac ttt tac tgg gaa aag cac      1728
Asp Asp Phe Phe Arg Pro Ile Arg Ser Tyr Phe Tyr Trp Glu Lys His
                565                 570                 575

tgc tac gat atc ccg agc tgc tgg gcg ctg                              1758
Cys Tyr Asp Ile Pro Ser Cys Trp Ala Leu
            580                 585


<210> SEQ ID NO 8
<211> LENGTH: 586
<212> TYPE: PRT
<213> ORGANISM: Mycobacterium complex

<400> SEQUENCE: 8

Met Ser Asn His His Arg Pro Arg Pro Trp Leu Pro His Thr Ile Arg
1               5                   10                  15

Arg Leu Ser Leu Pro Ile Leu Leu Phe Trp Val Gly Val Ala Ala Ile
            20                  25                  30

Thr Asn Ala Ala Val Pro Gln Leu Glu Val Val Gly Glu Ala His Asn
        35                  40                  45

Val Ala Gln Ser Ser Pro Asp Asp Pro Ser Leu Gln Ala Met Lys Arg
    50                  55                  60

Ile Gly Lys Val Phe His Glu Phe Asp Ser Asp Ser Ala Ala Met Ile
65                  70                  75                  80

Val Leu Glu Gly Asp Lys Pro Leu Gly Asn Asp Ala His Arg Phe Tyr
                85                  90                  95

Asp Thr Leu Leu Arg Asn Leu Ser Asn Asp Thr Lys His Val Glu His
            100                 105                 110

Val Gln Asp Phe Trp Gly Asp Pro Leu Thr Ala Ala Gly Ser Gln Ser
        115                 120                 125

Thr Asp Gly Lys Ala Ala Tyr Val Gln Val Tyr Leu Ala Gly Asn Gln
    130                 135                 140

Gly Glu Ala Leu Ser Ile Glu Ser Val Asp Ala Val Arg Asp Ile Val
145                 150                 155                 160

Ala His Thr Pro Pro Pro Ala Gly Val Lys Ala Tyr Val Thr Gly Ala
                165                 170                 175

Ala Pro Leu Met Ala Asp Gln Phe Gln Val Gly Ser Lys Gly Thr Ala
            180                 185                 190

Lys Val Thr Gly Ile Thr Leu Val Val Ile Ala Val Met Leu Leu Phe
        195                 200                 205

Val Tyr Arg Ser Val Val Thr Met Val Leu Val Leu Ile Thr Val Leu
    210                 215                 220

Ile Glu Leu Ala Ala Ala Arg Gly Ile Val Ala Phe Leu Gly Asn Ala
225                 230                 235                 240

Gly Val Ile Gly Leu Ser Thr Tyr Ser Thr Asn Leu Leu Thr Leu Leu
                245                 250                 255

Val Ile Ala Ala Gly Thr Asp Tyr Ala Ile Phe Val Leu Gly Arg Tyr
            260                 265                 270

His Glu Ala Arg Tyr Ala Ala Gln Asp Arg Glu Thr Ala Phe Tyr Thr
```

```
        275                 280                 285

Met Tyr Arg Gly Thr Ala His Val Val Leu Gly Ser Gly Leu Thr Val
    290                 295                 300

Ala Gly Ala Val Tyr Cys Leu Ser Phe Thr Arg Leu Pro Tyr Phe Gln
305                 310                 315                 320

Ser Leu Gly Ile Pro Ala Ser Ile Gly Val Met Ile Ala Leu Ala Ala
                325                 330                 335

Ala Leu Ser Leu Ala Pro Ser Val Leu Ile Leu Gly Ser Arg Phe Gly
            340                 345                 350

Cys Phe Glu Pro Lys Arg Arg Met Arg Thr Arg Gly Trp Arg Arg Ile
        355                 360                 365

Gly Thr Ala Ile Val Arg Trp Pro Gly Pro Ile Leu Ala Val Ala Cys
    370                 375                 380

Ala Ile Ala Val Val Gly Leu Leu Ala Leu Pro Gly Tyr Lys Thr Ser
385                 390                 395                 400

Tyr Asp Ala Arg Tyr Tyr Met Pro Ala Thr Ala Pro Ala Asn Ile Gly
                405                 410                 415

Tyr Met Ala Ala Glu Arg His Phe Pro Gln Ala Arg Leu Asn Pro Glu
            420                 425                 430

Leu Leu Met Ile Glu Thr Asp His Asp Met Arg Asn Pro Ala Asp Met
        435                 440                 445

Leu Ile Leu Asp Arg Ile Ala Lys Ala Val Phe His Leu Pro Gly Ile
    450                 455                 460

Gly Leu Val Gln Ala Met Thr Arg Pro Leu Gly Thr Pro Ile Asp His
465                 470                 475                 480

Ser Ser Ile Pro Phe Gln Ile Ser Met Gln Ser Val Gly Gln Ile Gln
                485                 490                 495

Asn Leu Lys Tyr Gln Arg Asp Arg Ala Ala Asp Leu Leu Lys Gln Ala
            500                 505                 510

Glu Glu Leu Gly Lys Thr Ile Glu Ile Leu Gln Arg Gln Tyr Ala Leu
        515                 520                 525

Gln Gln Glu Leu Ala Ala Ala Thr His Glu Gln Ala Glu Ser Phe His
    530                 535                 540

Gln Thr Ile Ala Thr Val Lys Glu Leu Arg Asp Arg Ile Ala Asn Phe
545                 550                 555                 560

Asp Asp Phe Phe Arg Pro Ile Arg Ser Tyr Phe Tyr Trp Glu Lys His
                565                 570                 575

Cys Tyr Asp Ile Pro Ser Cys Trp Ala Leu
            580                 585


<210> SEQ ID NO 9
<211> LENGTH: 447
<212> TYPE: DNA
<213> ORGANISM: Mycobacterium complex
<220> FEATURE:
<221> NAME/KEY: CDS
<222> LOCATION: (1)..(444)

<400> SEQUENCE: 9

gtg cag ggg att tca gtg act ggc ctg gtc aaa cgc ggc tgg atg gtg       48
Val Gln Gly Ile Ser Val Thr Gly Leu Val Lys Arg Gly Trp Met Val
1               5                   10                  15

ctg gtt gcc gtg gcg gtg gtg gcg gtc gcg gga ttc agc gtc tat cgg       96
Leu Val Ala Val Ala Val Val Ala Val Ala Gly Phe Ser Val Tyr Arg
            20                  25                  30

ttg cac ggc atc ttc ggc tcg cac gac acc acc tcg acc gcc ggt ggt      144
Leu His Gly Ile Phe Gly Ser His Asp Thr Thr Ser Thr Ala Gly Gly
```

-continued

```
        35                  40                  45

gtc gcg aac gac atc aag ccg ttc aac ccc aaa cag gta acc ctc gag      192
Val Ala Asn Asp Ile Lys Pro Phe Asn Pro Lys Gln Val Thr Leu Glu
    50                  55                  60

gtc ttt ggc gct ccc gga acc gtg gca acg atc aat tat ctg gac gtg      240
Val Phe Gly Ala Pro Gly Thr Val Ala Thr Ile Asn Tyr Leu Asp Val
65                  70                  75                  80

gat gcc aca cct cgg caa gtc ctg gac acg acc ctg ccg tgg tca tac      288
Asp Ala Thr Pro Arg Gln Val Leu Asp Thr Thr Leu Pro Trp Ser Tyr
                85                  90                  95

acg atc acg acg acc ctg ccc gcg gtc ttc gcc aat gtt gtc gcg caa      336
Thr Ile Thr Thr Thr Leu Pro Ala Val Phe Ala Asn Val Val Ala Gln
            100                 105                 110

ggc gac agc aat tcc atc ggc tgc cgc atc acc gtc aac ggt gta gtc      384
Gly Asp Ser Asn Ser Ile Gly Cys Arg Ile Thr Val Asn Gly Val Val
        115                 120                 125

aag gac gaa agg atc gtc aac gaa gtg cgc gcc tat acc ttc tgc ctc      432
Lys Asp Glu Arg Ile Val Asn Glu Val Arg Ala Tyr Thr Phe Cys Leu
    130                 135                 140

gac aag tcc tca tga                                                  447
Asp Lys Ser Ser
145


<210> SEQ ID NO 10
<211> LENGTH: 148
<212> TYPE: PRT
<213> ORGANISM: Mycobacterium complex

<400> SEQUENCE: 10

Val Gln Gly Ile Ser Val Thr Gly Leu Val Lys Arg Gly Trp Met Val
1               5                   10                  15

Leu Val Ala Val Ala Val Val Ala Val Ala Gly Phe Ser Val Tyr Arg
            20                  25                  30

Leu His Gly Ile Phe Gly Ser His Asp Thr Thr Ser Thr Ala Gly Gly
        35                  40                  45

Val Ala Asn Asp Ile Lys Pro Phe Asn Pro Lys Gln Val Thr Leu Glu
    50                  55                  60

Val Phe Gly Ala Pro Gly Thr Val Ala Thr Ile Asn Tyr Leu Asp Val
65                  70                  75                  80

Asp Ala Thr Pro Arg Gln Val Leu Asp Thr Thr Leu Pro Trp Ser Tyr
                85                  90                  95

Thr Ile Thr Thr Thr Leu Pro Ala Val Phe Ala Asn Val Val Ala Gln
            100                 105                 110

Gly Asp Ser Asn Ser Ile Gly Cys Arg Ile Thr Val Asn Gly Val Val
        115                 120                 125

Lys Asp Glu Arg Ile Val Asn Glu Val Arg Ala Tyr Thr Phe Cys Leu
    130                 135                 140

Asp Lys Ser Ser
145


<210> SEQ ID NO 11
<211> LENGTH: 399
<212> TYPE: DNA
<213> ORGANISM: Mycobacterium complex
<220> FEATURE:
<221> NAME/KEY: CDS
<222> LOCATION: (1)..(399)

<400> SEQUENCE: 11

ctg gtt gcc gtg gcg gtg gtg gcg gtc gcg gga ttc agc gtc tat cgg       48
```

-continued

```
Leu Val Ala Val Ala Val Val Ala Val Ala Gly Phe Ser Val Tyr Arg
1               5                   10                  15

ttg cac ggc atc ttc ggc tcg cac gac acc acc tcg acc gcc ggt ggt        96
Leu His Gly Ile Phe Gly Ser His Asp Thr Thr Ser Thr Ala Gly Gly
            20                  25                  30

gtc gcg aac gac atc aag ccg ttc aac ccc aaa cag gta acc ctc gag       144
Val Ala Asn Asp Ile Lys Pro Phe Asn Pro Lys Gln Val Thr Leu Glu
        35                  40                  45

gtc ttt ggc gct ccc gga acc gtg gca acg atc aat tat ctg gac gtg       192
Val Phe Gly Ala Pro Gly Thr Val Ala Thr Ile Asn Tyr Leu Asp Val
    50                  55                  60

gat gcc aca cct cgg caa gtc ctg gac acg acc ctg ccg tgg tca tac       240
Asp Ala Thr Pro Arg Gln Val Leu Asp Thr Thr Leu Pro Trp Ser Tyr
65                  70                  75                  80

acg atc acg acg acc ctg ccc gcg gtc ttc gcc aat gtt gtc gcg caa       288
Thr Ile Thr Thr Thr Leu Pro Ala Val Phe Ala Asn Val Val Ala Gln
                85                  90                  95

ggc gac agc aat tcc atc ggc tgc cgc atc acc gtc aac ggt gta gtc       336
Gly Asp Ser Asn Ser Ile Gly Cys Arg Ile Thr Val Asn Gly Val Val
            100                 105                 110

aag gac gaa agg atc gtc aac gaa gtg cgc gcc tat acc ttc tgc ctc       384
Lys Asp Glu Arg Ile Val Asn Glu Val Arg Ala Tyr Thr Phe Cys Leu
        115                 120                 125

gac aag tcc tca tga                                                   399
Asp Lys Ser Ser
    130
```

<210> SEQ ID NO 12
<211> LENGTH: 132
<212> TYPE: PRT
<213> ORGANISM: Mycobacterium complex

<400> SEQUENCE: 12

```
Leu Val Ala Val Ala Val Val Ala Val Ala Gly Phe Ser Val Tyr Arg
1               5                   10                  15

Leu His Gly Ile Phe Gly Ser His Asp Thr Thr Ser Thr Ala Gly Gly
            20                  25                  30

Val Ala Asn Asp Ile Lys Pro Phe Asn Pro Lys Gln Val Thr Leu Glu
        35                  40                  45

Val Phe Gly Ala Pro Gly Thr Val Ala Thr Ile Asn Tyr Leu Asp Val
    50                  55                  60

Asp Ala Thr Pro Arg Gln Val Leu Asp Thr Thr Leu Pro Trp Ser Tyr
65                  70                  75                  80

Thr Ile Thr Thr Thr Leu Pro Ala Val Phe Ala Asn Val Val Ala Gln
                85                  90                  95

Gly Asp Ser Asn Ser Ile Gly Cys Arg Ile Thr Val Asn Gly Val Val
            100                 105                 110

Lys Asp Glu Arg Ile Val Asn Glu Val Arg Ala Tyr Thr Phe Cys Leu
        115                 120                 125

Asp Lys Ser Ser
    130
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

-continued cgttcaaccc caaacaggta 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aatcgaactc gtggaacacc 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
attcagcgtc tatcggttgc 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agcagctcgg gatatcgtag 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ctacctcatc ttccggtcca 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
catagatccc ggacatggtg 20

<210> SEQ ID NO 19
<211> LENGTH: 2390
<212> TYPE: DNA
<213> ORGANISM: Mycobacterium canettii
<220> FEATURE:
<221> NAME/KEY: CDS
<222> LOCATION: (517)..(2307)

<400> SEQUENCE: 19
gatcccgtcg ccgcggcgct ggagctggcc gccgggcccg cagccgcccc gcgcgaggtc 60

```
gtgctggcga gcaaagccac catgcgcgcc acagccagcc ccggatcgct ggaccttgag    120

caacacgaac tcgccaaacg cttagaactt gggccgcagg cgaaatcggt ccagtcgccc    180

gagttcgccg ctcgcttggc tgccgctcaa cacaggtagc gcctaccagc ctcgctggtt    240

tccatggcgt gccccagtcc gaagctgctg ctgcttgact ccgcgcgctg ggcccgagcg    300

cgcgctgttg tacggcccaa acggcgtgtc ggtgtacagt cgcgcgctcg cggcttcagt    360

ccggcccccc gactccggca ggcccgacgg cgcccagcgc tagcccgaag ttccccccttg    420

taggggcggg ctgagtttcg atctgtttcg tgagcaggtg tttctgtgtt caacttccct    480

caacatgtac tcatgtatta ttgagaatag ctcggc gtg tca tcc tct gat gac     534
                                       Val Ser Ser Ser Asp Asp
                                       1               5

gct att atc gcg ctg acc gcg tgt tat aaa gta atc atg tac att acc     582
Ala Ile Ile Ala Leu Thr Ala Cys Tyr Lys Val Ile Met Tyr Ile Thr
            10                  15                  20

cgg gta ccc aac cgg gga tcc ccg ccg gcg gtg ctg ttg cgg gaa agc     630
Arg Val Pro Asn Arg Gly Ser Pro Pro Ala Val Leu Leu Arg Glu Ser
        25                  30                  35

ttc cgc gaa aac ggc aag gtc aag acg cgt acc ctg gcc aac ctc tca     678
Phe Arg Glu Asn Gly Lys Val Lys Thr Arg Thr Leu Ala Asn Leu Ser
    40                  45                  50

cgc tgg ccc gag cac aag ctg gac aga ctg gac cgg gcg ctt aag ggc     726
Arg Trp Pro Glu His Lys Leu Asp Arg Leu Asp Arg Ala Leu Lys Gly
55                  60                  65                  70

ttg ccg ccc gcg gac tgg gat cta gcc gag gcc ttc gat atc acc cgc     774
Leu Pro Pro Ala Asp Trp Asp Leu Ala Glu Ala Phe Asp Ile Thr Arg
                75                  80                  85

agc ctg ccg cac ggg cat gtg gcc gcg gtg gcc ggc acc gcc gag aag     822
Ser Leu Pro His Gly His Val Ala Ala Val Ala Gly Thr Ala Glu Lys
            90                  95                  100

ctg ggc ata ccc gag ctg atc gac ccc acc ccg tcg cgg cgg cgc aac     870
Leu Gly Ile Pro Glu Leu Ile Asp Pro Thr Pro Ser Arg Arg Arg Asn
        105                 110                 115

ctg gtg ctg gcc atg ctg atc ggg cag atc atc gag ccc gga tcg aaa     918
Leu Val Leu Ala Met Leu Ile Gly Gln Ile Ile Glu Pro Gly Ser Lys
    120                 125                 130

ctg gcg atc gcg cgc ggg ctg cgc gcc cag acc gcc acc agc acg ctg     966
Leu Ala Ile Ala Arg Gly Leu Arg Ala Gln Thr Ala Thr Ser Thr Leu
135                 140                 145                 150

ggt gcg gtg ctg ggt gtc tcg ggc gcc gat gag gac gac ctg tat gac    1014
Gly Ala Val Leu Gly Val Ser Gly Ala Asp Glu Asp Asp Leu Tyr Asp
                155                 160                 165

gcg atg gac tgg gcg ctg gag cgc aaa gac ggc atc gaa aac gcc ttg    1062
Ala Met Asp Trp Ala Leu Glu Arg Lys Asp Gly Ile Glu Asn Ala Leu
            170                 175                 180

gcc gca cgg cat ctg acc aac ggc acc ctg gtg ctc tat gac gta tcc    1110
Ala Ala Arg His Leu Thr Asn Gly Thr Leu Val Leu Tyr Asp Val Ser
        185                 190                 195

tcg gcg gcg ttc gag ggc cac acc tgc ccg ctg gga gcg atc ggg cac    1158
Ser Ala Ala Phe Glu Gly His Thr Cys Pro Leu Gly Ala Ile Gly His
    200                 205                 210

gcc cgc gac ggg gtc aaa ggc cgg ctg cag atc gtc tac ggg ctg ctg    1206
Ala Arg Asp Gly Val Lys Gly Arg Leu Gln Ile Val Tyr Gly Leu Leu
215                 220                 225                 230

tgc tca ccc aag gga gcg ccg gtg gcc atc gag gtg ttc aag ggc aac    1254
Cys Ser Pro Lys Gly Ala Pro Val Ala Ile Glu Val Phe Lys Gly Asn
                235                 240                 245

acc gcc gac ccg aaa act ctg aaa gct caa atc gac aag ctc aaa acc    1302
```

-continued

```
Thr Ala Asp Pro Lys Thr Leu Lys Ala Gln Ile Asp Lys Leu Lys Thr
            250                 255                 260

cgg ttc ggg ttg acc cgc atc gcc ctg gtg ggc gat cgg ggc atg ctc      1350
Arg Phe Gly Leu Thr Arg Ile Ala Leu Val Gly Asp Arg Gly Met Leu
        265                 270                 275

act tcc gcg cgc atc cgt gac gag ctg cgt ccg gcg cac ctg gat tgg      1398
Thr Ser Ala Arg Ile Arg Asp Glu Leu Arg Pro Ala His Leu Asp Trp
    280                 285                 290

atc agc gcg ctg cgc gcc ccg cag atc aag atc ctg ctc gag gac ggg      1446
Ile Ser Ala Leu Arg Ala Pro Gln Ile Lys Ile Leu Leu Glu Asp Gly
295                 300                 305                 310

gcg ctg cag ctg tcg ctg ttc gat gag cag aac ctg ttc gag atc act      1494
Ala Leu Gln Leu Ser Leu Phe Asp Glu Gln Asn Leu Phe Glu Ile Thr
                315                 320                 325

cac ccc gac tat ccc ggt gag cgg ctg gtg tgc tgc cac aac ccc gcc      1542
His Pro Asp Tyr Pro Gly Glu Arg Leu Val Cys Cys His Asn Pro Ala
            330                 335                 340

ctg gcc gac gag cgc gcc cgc aaa cgc gcc gag ctg ctg gcg gcc acc      1590
Leu Ala Asp Glu Arg Ala Arg Lys Arg Ala Glu Leu Leu Ala Ala Thr
        345                 350                 355

gaa aag gag ctg cag gcc atc gcc gaa gcc acc cgc cgc caa cgc cgg      1638
Glu Lys Glu Leu Gln Ala Ile Ala Glu Ala Thr Arg Arg Gln Arg Arg
    360                 365                 370

ccg tta cgc ggt aca gac aag atc ggc ctg cgg gtg ggc aag gtg cgc      1686
Pro Leu Arg Gly Thr Asp Lys Ile Gly Leu Arg Val Gly Lys Val Arg
375                 380                 385                 390

aac aag ttc aag atg gcc aag cac ttt gac ctg cac atc acc gat gag      1734
Asn Lys Phe Lys Met Ala Lys His Phe Asp Leu His Ile Thr Asp Glu
                395                 400                 405

gcc ttc agc ttc acc cgc aac cag aac agt atc gcc gcc gag gcc gcc      1782
Ala Phe Ser Phe Thr Arg Asn Gln Asn Ser Ile Ala Ala Glu Ala Ala
            410                 415                 420

ctc gac ggc atc tac gtg cta cgc acc agc ctg ccc gac aac gcc ctg      1830
Leu Asp Gly Ile Tyr Val Leu Arg Thr Ser Leu Pro Asp Asn Ala Leu
        425                 430                 435

ggc cgc gac gac gtg gtg ggc cgc tac aaa gac ctc gcc gac gtc gaa      1878
Gly Arg Asp Asp Val Val Gly Arg Tyr Lys Asp Leu Ala Asp Val Glu
    440                 445                 450

cgc ttc ttc cgc acc ctc aac agc gaa ctg gac gta cgc ccc atc cgg      1926
Arg Phe Phe Arg Thr Leu Asn Ser Glu Leu Asp Val Arg Pro Ile Arg
455                 460                 465                 470

cat cgg ctg gcc gac cgg gtc cgc gcc cac atg ttc ttg cac atg ctc      1974
His Arg Leu Ala Asp Arg Val Arg Ala His Met Phe Leu His Met Leu
                475                 480                 485

tcc tac tac atc agc tgg cac atg aaa caa gcc ctg gcc cca atc ctg      2022
Ser Tyr Tyr Ile Ser Trp His Met Lys Gln Ala Leu Ala Pro Ile Leu
            490                 495                 500

ttc acc gac aac gac aaa ccc gcc gcc gcc gcc aaa cgc gcc gac ccc      2070
Phe Thr Asp Asn Asp Lys Pro Ala Ala Ala Ala Lys Arg Ala Asp Pro
        505                 510                 515

gtc gcg cca gcc caa cgc tcc gac gaa gcg ctg aac aag gca gca cgc      2118
Val Ala Pro Ala Gln Arg Ser Asp Glu Ala Leu Asn Lys Ala Ala Arg
    520                 525                 530

aaa cgc acc gaa gac aac caa ccg gtg cac agc ttc acc agc ctg ctc      2166
Lys Arg Thr Glu Asp Asn Gln Pro Val His Ser Phe Thr Ser Leu Leu
535                 540                 545                 550

acc gac ctg gcc acc atc tgc gcc aac tac atc caa ccc aca gac gac      2214
Thr Asp Leu Ala Thr Ile Cys Ala Asn Tyr Ile Gln Pro Thr Asp Asp
                555                 560                 565

ctg cca gca ttc acc aaa acc acc acc ccc acc ccc aca caa cgg cgc      2262
```

-continued

```
Leu Pro Ala Phe Thr Lys Thr Thr Thr Pro Thr Pro Thr Gln Arg Arg
            570                 575                 580

gcc ttc gac cta ctg gcc gtt tcc cac cgc cac ggc ctg gcg tag         2307
Ala Phe Asp Leu Leu Ala Val Ser His Arg His Gly Leu Ala
        585                 590                 595

tcagtaccga accacaaatg cccaggtcaa cgacacaaac cgcgccggat caggggggaac   2367

ttcgggctag ccgggcgcgc cgg                                            2390


<210> SEQ ID NO 20
<211> LENGTH: 596
<212> TYPE: PRT
<213> ORGANISM: Mycobacterium canettii

<400> SEQUENCE: 20

Val Ser Ser Ser Asp Asp Ala Ile Ile Ala Leu Thr Ala Cys Tyr Lys
1               5                   10                  15

Val Ile Met Tyr Ile Thr Arg Val Pro Asn Arg Gly Ser Pro Pro Ala
            20                  25                  30

Val Leu Leu Arg Glu Ser Phe Arg Glu Asn Gly Lys Val Lys Thr Arg
        35                  40                  45

Thr Leu Ala Asn Leu Ser Arg Trp Pro Glu His Lys Leu Asp Arg Leu
    50                  55                  60

Asp Arg Ala Leu Lys Gly Leu Pro Pro Ala Asp Trp Asp Leu Ala Glu
65                  70                  75                  80

Ala Phe Asp Ile Thr Arg Ser Leu Pro His Gly His Val Ala Ala Val
                85                  90                  95

Ala Gly Thr Ala Glu Lys Leu Gly Ile Pro Glu Leu Ile Asp Pro Thr
            100                 105                 110

Pro Ser Arg Arg Arg Asn Leu Val Leu Ala Met Leu Ile Gly Gln Ile
        115                 120                 125

Ile Glu Pro Gly Ser Lys Leu Ala Ile Ala Arg Gly Leu Arg Ala Gln
    130                 135                 140

Thr Ala Thr Ser Thr Leu Gly Ala Val Leu Gly Val Ser Gly Ala Asp
145                 150                 155                 160

Glu Asp Asp Leu Tyr Asp Ala Met Asp Trp Ala Leu Glu Arg Lys Asp
                165                 170                 175

Gly Ile Glu Asn Ala Leu Ala Ala Arg His Leu Thr Asn Gly Thr Leu
            180                 185                 190

Val Leu Tyr Asp Val Ser Ser Ala Ala Phe Glu Gly His Thr Cys Pro
        195                 200                 205

Leu Gly Ala Ile Gly His Ala Arg Asp Gly Val Lys Gly Arg Leu Gln
    210                 215                 220

Ile Val Tyr Gly Leu Leu Cys Ser Pro Lys Gly Ala Pro Val Ala Ile
225                 230                 235                 240

Glu Val Phe Lys Gly Asn Thr Ala Asp Pro Lys Thr Leu Lys Ala Gln
                245                 250                 255

Ile Asp Lys Leu Lys Thr Arg Phe Gly Leu Thr Arg Ile Ala Leu Val
            260                 265                 270

Gly Asp Arg Gly Met Leu Thr Ser Ala Arg Ile Arg Asp Glu Leu Arg
        275                 280                 285

Pro Ala His Leu Asp Trp Ile Ser Ala Leu Arg Ala Pro Gln Ile Lys
    290                 295                 300

Ile Leu Leu Glu Asp Gly Ala Leu Gln Leu Ser Leu Phe Asp Glu Gln
305                 310                 315                 320

Asn Leu Phe Glu Ile Thr His Pro Asp Tyr Pro Gly Glu Arg Leu Val
```

```
                325                 330                 335

Cys Cys His Asn Pro Ala Leu Ala Asp Glu Arg Ala Arg Lys Arg Ala
            340                 345                 350

Glu Leu Leu Ala Ala Thr Glu Lys Glu Leu Gln Ala Ile Ala Glu Ala
        355                 360                 365

Thr Arg Arg Gln Arg Arg Pro Leu Arg Gly Thr Asp Lys Ile Gly Leu
    370                 375                 380

Arg Val Gly Lys Val Arg Asn Lys Phe Lys Met Ala Lys His Phe Asp
385                 390                 395                 400

Leu His Ile Thr Asp Glu Ala Phe Ser Phe Thr Arg Asn Gln Asn Ser
                405                 410                 415

Ile Ala Ala Glu Ala Ala Leu Asp Gly Ile Tyr Val Leu Arg Thr Ser
            420                 425                 430

Leu Pro Asp Asn Ala Leu Gly Arg Asp Asp Val Val Gly Arg Tyr Lys
        435                 440                 445

Asp Leu Ala Asp Val Glu Arg Phe Phe Arg Thr Leu Asn Ser Glu Leu
    450                 455                 460

Asp Val Arg Pro Ile Arg His Arg Leu Ala Asp Arg Val Arg Ala His
465                 470                 475                 480

Met Phe Leu His Met Leu Ser Tyr Tyr Ile Ser Trp His Met Lys Gln
                485                 490                 495

Ala Leu Ala Pro Ile Leu Phe Thr Asp Asn Asp Lys Pro Ala Ala Ala
            500                 505                 510

Ala Lys Arg Ala Asp Pro Val Ala Pro Ala Gln Arg Ser Asp Glu Ala
        515                 520                 525

Leu Asn Lys Ala Ala Arg Lys Arg Thr Glu Asp Asn Gln Pro Val His
    530                 535                 540

Ser Phe Thr Ser Leu Leu Thr Asp Leu Ala Thr Ile Cys Ala Asn Tyr
545                 550                 555                 560

Ile Gln Pro Thr Asp Asp Leu Pro Ala Phe Thr Lys Thr Thr Thr Pro
                565                 570                 575

Thr Pro Thr Gln Arg Arg Ala Phe Asp Leu Leu Ala Val Ser His Arg
            580                 585                 590

His Gly Leu Ala
        595


<210> SEQ ID NO 21
<211> LENGTH: 1191
<212> TYPE: DNA
<213> ORGANISM: Mycobacterium tuberculosis
<220> FEATURE:
<221> NAME/KEY: CDS
<222> LOCATION: (1)..(1191)

<400> SEQUENCE: 21

gtg cag ggg att tca gtg act ggc ctg gtc aaa cgc ggc tgg atg gtg       48
Val Gln Gly Ile Ser Val Thr Gly Leu Val Lys Arg Gly Trp Met Val
1               5                   10                  15

aga tcc gtc ttt gac acg atc gac ggt atc gac caa ctc ggc gag cag       96
Arg Ser Val Phe Asp Thr Ile Asp Gly Ile Asp Gln Leu Gly Glu Gln
            20                  25                  30

ctg gcc agc gtg acc gta acc ttg gac aag ttg gct gcg atc cag cct      144
Leu Ala Ser Val Thr Val Thr Leu Asp Lys Leu Ala Ala Ile Gln Pro
        35                  40                  45

caa ttg gtg gcg ctg cta cca gac gag atc gcc agc cag cag atc aat      192
Gln Leu Val Ala Leu Leu Pro Asp Glu Ile Ala Ser Gln Gln Ile Asn
    50                  55                  60
```

-continued

```
cgg gaa ctg gcg ctg gct aac tac gcc acc atg tcc ggg atc tat gcc      240
Arg Glu Leu Ala Leu Ala Asn Tyr Ala Thr Met Ser Gly Ile Tyr Ala
65                  70                  75                  80

cag acg gcg gcc ttg atc gaa aac gct gcc gcc atg gga caa gcc ttt      288
Gln Thr Ala Ala Leu Ile Glu Asn Ala Ala Ala Met Gly Gln Ala Phe
                85                  90                  95

gac gcc gcc aag aac gac gac tcc ttc tat ctg ccg ccg gag gct ttt      336
Asp Ala Ala Lys Asn Asp Asp Ser Phe Tyr Leu Pro Pro Glu Ala Phe
            100                 105                 110

gac aac cca gat ttc cag cgc ggc ctg aaa ttg ttc ctg tcg gca gac      384
Asp Asn Pro Asp Phe Gln Arg Gly Leu Lys Leu Phe Leu Ser Ala Asp
        115                 120                 125

ggt aag gcg gct cgg atg atc atc tcc cat gaa ggc gat ccc gcc acc      432
Gly Lys Ala Ala Arg Met Ile Ile Ser His Glu Gly Asp Pro Ala Thr
    130                 135                 140

ccc gaa ggc att tcg cat atc gac gcg atc aag cag gcg gcc cac gag      480
Pro Glu Gly Ile Ser His Ile Asp Ala Ile Lys Gln Ala Ala His Glu
145                 150                 155                 160

gcc gtg aag ggc act ccc atg gcg ggt gct ggg atc tat ctg gcc ggc      528
Ala Val Lys Gly Thr Pro Met Ala Gly Ala Gly Ile Tyr Leu Ala Gly
                165                 170                 175

acg gcc gcc acc ttc aag gac att caa gac ggc gcc acc tac gac ctc      576
Thr Ala Ala Thr Phe Lys Asp Ile Gln Asp Gly Ala Thr Tyr Asp Leu
            180                 185                 190

ctg atc gcc gga ata gcc gcg ctg agc ttg att ttg ctc atc atg atg      624
Leu Ile Ala Gly Ile Ala Ala Leu Ser Leu Ile Leu Leu Ile Met Met
        195                 200                 205

atc att acc cga agc ctg gtt gcg gcg ctg gtg atc gtg ggc acg gtg      672
Ile Ile Thr Arg Ser Leu Val Ala Ala Leu Val Ile Val Gly Thr Val
    210                 215                 220

gcg ctg tcg ttg ggc gct tct ttt ggc ctg tcc gtg ctg gtg tgg cag      720
Ala Leu Ser Leu Gly Ala Ser Phe Gly Leu Ser Val Leu Val Trp Gln
225                 230                 235                 240

cat ctt ctc ggt atc cag ttg tac tgg atc gtg ctc gcg ctg gcc gtc      768
His Leu Leu Gly Ile Gln Leu Tyr Trp Ile Val Leu Ala Leu Ala Val
                245                 250                 255

atc ctg ctc ctg gcc gtg gga tcg gac tat aac ttg ctg ctg att tcc      816
Ile Leu Leu Leu Ala Val Gly Ser Asp Tyr Asn Leu Leu Leu Ile Ser
            260                 265                 270

cga ttc aag gag gag atc ggt gca ggt ttg aac acc ggc atc atc cgt      864
Arg Phe Lys Glu Glu Ile Gly Ala Gly Leu Asn Thr Gly Ile Ile Arg
        275                 280                 285

gcg atg gcc ggc acc ggc ggg gtg gtg acc gct gcc ggc ctg gtg ttc      912
Ala Met Ala Gly Thr Gly Gly Val Val Thr Ala Ala Gly Leu Val Phe
    290                 295                 300

gcc gcc act atg tct tcg ttc gtg ttc agt gat ttg cgg gtc ctc ggt      960
Ala Ala Thr Met Ser Ser Phe Val Phe Ser Asp Leu Arg Val Leu Gly
305                 310                 315                 320

cag atc ggg acc acc att ggt ctt ggg ctg ctg ttc gac acg ctg gtg     1008
Gln Ile Gly Thr Thr Ile Gly Leu Gly Leu Leu Phe Asp Thr Leu Val
                325                 330                 335

gtg cgc gcg ttc atg acc ccg tcc atc gcg gtg ctg ctc ggg cgc tgg     1056
Val Arg Ala Phe Met Thr Pro Ser Ile Ala Val Leu Leu Gly Arg Trp
            340                 345                 350

ttc tgg tgg ccg caa cga gtg cgc ccg cgc cct gcc agc agg atg ctt     1104
Phe Trp Trp Pro Gln Arg Val Arg Pro Arg Pro Ala Ser Arg Met Leu
        355                 360                 365

cgg ccg tac ggc ccg cgg ccc gtg gtt cgt gaa ttg ctg ctg cgc gag     1152
Arg Pro Tyr Gly Pro Arg Pro Val Val Arg Glu Leu Leu Leu Arg Glu
    370                 375                 380
```

```
ggc aac gat gac ccg aga act cag gtg gct acc cac cgt                 1191
Gly Asn Asp Asp Pro Arg Thr Gln Val Ala Thr His Arg
385                 390                 395
```

<210> SEQ ID NO 22
<211> LENGTH: 397
<212> TYPE: PRT
<213> ORGANISM: Mycobacterium tuberculosis

<400> SEQUENCE: 22

```
Val Gln Gly Ile Ser Val Thr Gly Leu Val Lys Arg Gly Trp Met Val
1               5                   10                  15

Arg Ser Val Phe Asp Thr Ile Asp Gly Ile Asp Gln Leu Gly Glu Gln
            20                  25                  30

Leu Ala Ser Val Thr Val Thr Leu Asp Lys Leu Ala Ala Ile Gln Pro
        35                  40                  45

Gln Leu Val Ala Leu Leu Pro Asp Glu Ile Ala Ser Gln Gln Ile Asn
    50                  55                  60

Arg Glu Leu Ala Leu Ala Asn Tyr Ala Thr Met Ser Gly Ile Tyr Ala
65                  70                  75                  80

Gln Thr Ala Ala Leu Ile Glu Asn Ala Ala Ala Met Gly Gln Ala Phe
                85                  90                  95

Asp Ala Ala Lys Asn Asp Asp Ser Phe Tyr Leu Pro Pro Glu Ala Phe
            100                 105                 110

Asp Asn Pro Asp Phe Gln Arg Gly Leu Lys Leu Phe Leu Ser Ala Asp
        115                 120                 125

Gly Lys Ala Ala Arg Met Ile Ile Ser His Glu Gly Asp Pro Ala Thr
    130                 135                 140

Pro Glu Gly Ile Ser His Ile Asp Ala Ile Lys Gln Ala Ala His Glu
145                 150                 155                 160

Ala Val Lys Gly Thr Pro Met Ala Gly Ala Gly Ile Tyr Leu Ala Gly
                165                 170                 175

Thr Ala Ala Thr Phe Lys Asp Ile Gln Asp Gly Ala Thr Tyr Asp Leu
            180                 185                 190

Leu Ile Ala Gly Ile Ala Ala Leu Ser Leu Ile Leu Leu Ile Met Met
        195                 200                 205

Ile Ile Thr Arg Ser Leu Val Ala Ala Leu Val Ile Val Gly Thr Val
    210                 215                 220

Ala Leu Ser Leu Gly Ala Ser Phe Gly Leu Ser Val Leu Val Trp Gln
225                 230                 235                 240

His Leu Leu Gly Ile Gln Leu Tyr Trp Ile Val Leu Ala Leu Ala Val
                245                 250                 255

Ile Leu Leu Leu Ala Val Gly Ser Asp Tyr Asn Leu Leu Leu Ile Ser
            260                 265                 270

Arg Phe Lys Glu Glu Ile Gly Ala Gly Leu Asn Thr Gly Ile Ile Arg
        275                 280                 285

Ala Met Ala Gly Thr Gly Gly Val Val Thr Ala Ala Gly Leu Val Phe
    290                 295                 300

Ala Ala Thr Met Ser Ser Phe Val Phe Ser Asp Leu Arg Val Leu Gly
305                 310                 315                 320

Gln Ile Gly Thr Thr Ile Gly Leu Gly Leu Leu Phe Asp Thr Leu Val
                325                 330                 335

Val Arg Ala Phe Met Thr Pro Ser Ile Ala Val Leu Leu Gly Arg Trp
            340                 345                 350

Phe Trp Trp Pro Gln Arg Val Arg Pro Arg Pro Ala Ser Arg Met Leu
        355                 360                 365
```

```
Arg Pro Tyr Gly Pro Arg Pro Val Val Arg Glu Leu Leu Leu Arg Glu
    370                 375                 380

Gly Asn Asp Asp Pro Arg Thr Gln Val Ala Thr His Arg
385                 390                 395


<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

ggcctggtca aacgcggctg gatgctg                                         27


<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

agatccgtct ttgacacgat cgacg                                           25


<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

gtcagccaag tcaggctacc                                                 20


<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

gaaacagtcc ccagcaggt                                                  19


<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

caacgttgtg gttgttgagg                                                 20


<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 28
ttcaacgggt tactgcgaat 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tatagctctc ggcaggttcc 20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ctcgaccgcg acgatgtgc 19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
atcggcatct atgtcggtgt 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cctcgttgtc accgcgtatg 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
ttatcttggc gttgacgatg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34

-continued ctgacgtcgt tgtcgaggta 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
catataaggg tgcccgctac 20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gtacccccag gcgatctt 18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
caaggggtat gaggttcacg 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ctcgtcgaag gccactaaag 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cggtgattcg tgattgaaca 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
aaggcgaaca gattcagcat 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
aatcacgctg ctgctactcc 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
caagttgggt ctggtcgaat 20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gtgcttttgc ctcttggtc 19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
gctacccaag gtctcctggt 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
cagctggtga gttcaaatgc 20

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
ctcccgacac ctgttcgt 18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
tggattgtcg acggtatgaa 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
ggtaatcgtg gccgacaag 19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
ggtcgataag gtcacggaac 20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
cagctcttcc cctctcgac 19

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
ggtgtgattt ggtgagacga tg 22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
caatcagggc tgtgctaacc 20

<210> SEQ ID NO 53
<211> LENGTH: 23

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
agttcctcct gactaatcca ggc 23

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
cgacagttgt gcgtactggt 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
cgatggtcaa caccactacg 20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
gtgtaggtca gccccatcc 19

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ctggacctcg atgaccactc 20

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
gcccaacagc tcgacatc 18

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
gtaaccgctt caccggaat 19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
ctgcaaccat ccggtacac 19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
gtcaactcca cggaaagacc 20

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
gtcatgaacg ccggacag 18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
cggcagctag acgacctc 18

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
tcacataggg gctgcgatag 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
aacgtgctgc gataggtttt 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
agaggaacct ttcggtggtt 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gaaatacgag tgcgctgacc 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gccatcaacg tcaagaacct 20

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ctctgaacca tcggtgtcg 19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
cggccaggta acaaggagt 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggatgtcact cggaacggca 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cgatggtgtt tcttggtgag 20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
caccgggctg atcgagcga 19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ggatcggctc agtgaatacc 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gtggagcacc ttgacctgat 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ttgattcgcc aacaactgaa 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cgtcgaatac gagtcgaaca 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
gggctggtta gtgtcgattc 20

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
agcgcgtcga acaccggc 18

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gagccactcc gatgttgact 20

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
cctgaatccg cgcaattcca t 21

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
cacgcgaacc ctacctacat 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
gttctcctgt cgaacctcca 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
ggacggtgac ggtatttgtc 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
acttcaccgg tttcatctcg 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tcgccaactt ctatggacct 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
atcgatcagg tcgtcaatgc 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
aaaccatgca gcgtctgcca 20

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
acgccaccat caagatcc 18

<210> SEQ ID NO 90

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
gcgtttctgc gtctggttga 20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
ggttgccaac gttaccgatg c 21

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
ccggtggtgg tggcggct 18

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
gggttcacgt tcattactgt tc 22

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
cccatcgtgg tcgttcacc 19

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
cctgcgctta tctctagcgg 20

<210> SEQ ID NO 96
<211> LENGTH: 19
<212> TYPE: DNA

<213> ORGANISM: Artificial Sequence
<220> FEATURE:
<223> OTHER INFORMATION: Description of Artificial Sequence: Synthetic primer

<400> SEQUENCE: 96
gtacccgcac cacctgctg 19

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
cgttcaaccc caaacaggta 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ctacctcatc ttccggtcca 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
aatcgaactc gtggaacacc 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
catagatccc ggacatggtg 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
ctaccagcac cgtcatctca 20

<210> SEQ ID NO 102
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 102
acaagctgat ccaccgagac 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
aggtcgtatg gacgaacacc 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
gttcgtgtgt tgcgtcaagt 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
cgggtgctct atgcaatgtt 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
cagctgggtg tgcttgtaaa 20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tatgcgatca ggcgtacttg 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
caaagcagtg gttcagcagt 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
caaagcagtg gttcagcagt 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
atcaggagct gcaaaccaac 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ggcgtcatgg accctatatc 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
ggcgtcatgg accctatatc 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
gtatcagagg gaccgagcag 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114

-continued

```
gtatcagagg gaccgagcag                                                  20


<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115

catagatccc ggacatggtg                                                  20


<210> SEQ ID NO 116
<211> LENGTH: 48
<212> TYPE: DNA
<213> ORGANISM: Mycobacterium bovis

<400> SEQUENCE: 116

ggcctggtcc gcggctggtg gtgctggttg ccgtggcggt ggtggcgg                   48


<210> SEQ ID NO 117
<211> LENGTH: 42
<212> TYPE: DNA
<213> ORGANISM: Mycobacterium tuberculosis

<400> SEQUENCE: 117

ggcctggtcc gcggctggtg gtggtccgtc tttgccgtcg cg                         42
```

DELETE SEQUENCE IN *M. TUBERCULOSIS*, METHOD FOR DETECTING MYCOBACTERIA USING THESE SEQUENCES AND VACCINES

The present invention pertains to the field of biology, more particularly the subject of the present invention is the identification of a nucleotide sequence which make it possible in particular to distinguish an infection resulting from *Mycobacterium tuberculosis* from an infection resulting from *Mycobacterium africanum, Mycobacterium canetti, Mycobacterium microti, Mycobacterium bovis, Mycobacterium bovis* BCG. The subject of the present invention is also a method for detecting the sequences in question by the products of expression of these sequences and the kits for carrying out these methods. Finally, the subject of the present invention is novel vaccines.

Despite more than a century of research since the discovery of *Mycobacterium tuberculosis*, the aetiological agent of tuberculosis, this disease remains one of the major causes of human mortality. *M. tuberculosis* is expected to kill 3 million people annually (Snider, 1989 Rev. Inf. Dis. S335) and the number of new people getting infected each year is rising and is estimated at 8.8 million. Although the majority of these are in developing countries, the disease is assuming renewed importance in the western countries due to the increasing number of homeless people, the impact of the AIDS epidemic, the changing global migration, and the travel patterns.

Early tuberculosis often goes unrecognized in an otherwise healthy individual. Classical initial methods of diagnosis include examination of a sputum smear under a microscope for acid-fast mycobacteria and an x-ray of the lungs. However, in a vast majority of cases the sputum smear examination is negative for *Mycobacteria* in the early stages of the disease, and lung changes may not be obvious on an x-ray until several months following infection. Another complicating factor is that acid-fast bacteria in a sputum smear may often be other species of mycobacteria. Antibiotics used for treating tuberculosis have considerable side effects, and must be taken as a combination of three or more drugs for a six to twelve month period. In addition, the possibility of inducing the appearance of drug resistant tuberculosis prevents therapy from being administered without solid evidence to support the diagnosis. Currently the only absolutely reliable method of diagnosis is based on culturing *M. tuberculosis* from the clinical specimen and identifying it morphologically and biochemically. This usually takes anywhere from three to six weeks, during which time a patient may become seriously ill and infect other individuals. Therefore, a rapid test capable of reliably detecting the presence of *M. tuberculosis* is vital for the early detection and treatment. Several molecular tests have been developed recently for the rapid detection and identification of *M. tuberculosis*, such as the Gen-Probe "Amplified *Mycobacterium tuberculosis* Direct Test"; this test amplifies *M. tuberculosis* 16S ribosomal RNA from respiratory specimens and uses a chemiluminescent probe to detect the amplified product with a reported sensitivity of about 91%. The discovery of the IS6110 insertion element (Cave et al., Eisenach et al., 1990 J. Infectious Diseases 161:977-981; Thierry et al. 1990 J. Clin. Microbiol. 28: 2668-2673) and the belief that this element may only be present in *Mycobacterium* complex (*M. tuberculosis, M. bovis, M. bovis*-BCG, *M. africanum, M. canettii* and *M. microti*) spawned a whole series of rapid diagnostic strategies (Brisson-Noel et al., 1991 Lancet 338: 364-366; Clarridge et al. 1993, J. Clin. Microbiol. 31: 2049-2056; Cormican et al. 1992 J. Clin. Pathology 1992, 45: 601-604; Cousins et al., 1992 J. Clin. Microbiol. 30: 255-258; Del Portillo et al. 1991 J. Clin. Microbiol. 29: 2163-2168; Folgueira et al., 1994 Neurology 44: 1336-1338; Forbes et al. 1993, J. Clin. Microbiol. 31: 1688-1694; Hermans et al. 1990 J. Clin. Microbiol. 28: 1204-1213; Kaltwasser et al. 1993 Mol. Cell. Probes 7: 465-470; Kocagoz et al. 1993 J. Clin. Microbiol. 31: 1435-1438; Kolk et al. 1992 J. Clin. Microbiol. 30: 2567-2575; Kox et al. 1994 J. Clin. Microbiol. 32: 672-678; Liu et al. 1994 Neurology 44: 1161-1164; Miller et al. 1994 J. Clin. Microbiol. 32: 393-397; Reischl et al. 1994 Biotechniques 17: 844-845; Schluger et al. 1994 Chest 105: 1116-1121; Shawar et al. 1993 J. Clin. Microbiol. 31: 61-65; Wilson et al 1993 J. Clin. Microbiol. 28: 2668-2673). These tests employ various techniques to extract DNA from the sputum. PCR is used to amplify IS6110 DNA sequences from the extracted DNA. The successful amplification of this DNA is considered to be an indicator of the presence of *M. tuberculosis* infection. U.S. Pat. Nos. 5,168,039 and 5,370,998 have been issued to Crawford et al. for the IS6110 based detection of tuberculosis. European patent EP 0,461,045 has been issued to Guesdon for the IS6110 based detection of tuberculosis.

Thus, these molecular assays used to detect *M. tuberculosis* depend on the IS6110 insertion sequence (about 10 copies) or the 16S ribosomal RNA (thousands of copies). However, these methods do not provide any information regarding the sub-type of the mycobacteria. Indeed several dozen species of *Mycobacteria* are known, and most are non-pathogenic for humans; tuberculosis is usually caused by infection due to *M. tuberculosis*, with a few cases being caused by *M. bovis, M. canettii*, and *M. africanum*. In order to choose an appropriate treatment and to conduct epidemiological investigations it is absolutely necessary to be able to rapidly and accurately identify isolates, i.e to distinguish the sub-type of mycobacteria of the *Mycobacterium* complex, originating from potential tuberculosis patients. That's the problem the present invention intends to solve.

The present invention provides an isolated or purified nucleic acid from *Mycobacterium* complex wherein said nucleic acid is selected from the group consisting of:

a) SEQ ID No 1, named TbD1 region;
b) Nucleic acid having a sequence fully complementary to SEQ ID No 1.
c) Nucleic acid fragment comprising at least 8, 12, 15, 20, 25, 30, 50, 100, 250, 500, 750, 1000, 1500, 2000, 2500, 3000 consecutive nucleotides of SEQ ID No 1;
d) Nucleic acid having at least 90% sequence identity after optimal alignment with a sequence defined in a) or b);
e) Nucleic acid that hybridizes under stringent conditions with the nucleic acid defined in a) or b);

As used herein, the terms <<isolated>> and <<purified>> according to the invention refer to a level of purity that is achievable using current technology. The molecules of the invention do not need to be absolutely pure (i.e., contain absolutely no molecules of other cellular macromolecules), but should be sufficiently pure so that one of ordinary skill in the art would recognize that they are no longer present in the environment in which they were originally found (i.e., the cellular middle). Thus, a purified or isolated molecule according to the present invention is one that have been removed from at least one other macromolecule present in the natural environment in which it was found. More preferably, the molecules of the invention are essentially purified and/or isolated, which means that the composition in which they are present is almost completely, or even absolutely, free of other macromolecules found in the environment in which the molecules of the invention are originally found. Isolation and purification thus does not occur by addition or removal of salts, solvents, or elements of the periodic table, but must include the removal of at least some macromolecules. The nucleic acids encompassed by the invention are purified and/or isolated by any appropriate technique known to the ordinary artisan. Such techniques are widely known, commonly practiced, and well within the skill of the ordinary artisan. As used herein, the term "nucleic acid" refers to a polynucleotide sequence such as a single or double stranded DNA sequence, RNA sequence, cDNA sequence; such a polynucleotide sequence has been isolated, purified or synthesized and may be constituted with natural or non natural nucleotides. In a preferred embodiment the DNA molecule of the invention is a double stranded DNA molecule. As used herein, the terms "nucleic acid", "oligonucleotide", "polynucleotide" have the same meaning and are used indifferently.

By the term "*Mycobacterium* complex" as used herein, it is meant the complex of mycobacteria causing tuberculosis which are *Mycobacterium tuberculosis, Mycobacterium bovis, Mycobacterium africanum, Mycobacterium microti, Mycobacterium canettii* and the vaccine strain *Mycobacterium bovis* BCG.

The present invention encompasses not only the entire sequence SEQ ID No 1, its complement, and its double-stranded form, but any fragment of this sequence, its complement, and its double-stranded form.

In embodiments, the fragment of SEQ ID No 1 comprises at least approximately 8 nucleotides. For example, the fragment can be between approximately 8 and 30 nucleotides and can be designed as a primer for polynucleotide synthesis. In another preferred embodiment, the fragment of SEQ ID No 1 comprises between approximately 1,500 and approximately 2,500 nucleotides, and more preferably 2153 nucleotides corresponding to SEQ ID No 4 (see FIG. 5). As used herein, "nucleotides" is used in reference to the number of nucleotides on a single-stranded nucleic acid. However, the term also encompasses double-stranded molecules. Thus, a fragment comprising 2,153 nucleotides according to the invention is a single-stranded molecule comprising 2,153 nucleotides, and also a double stranded molecule comprising 2153 base pairs (bp).

In a preferred embodiment, the nucleic acid fragment of the invention is specifically deleted in the genome of *Mycobacterium tuberculosis*, excepted in *Mycobacterium tuberculosis* strains having the sequence CTG at codon 463 of gene katG and having no or very few IS6110 sequences inserted in their genome and present in the genome of *Mycobacterium africanum, Mycobacterium canettii, Mycobacterium microti, Mycobacterium bovis, Mycobacterium bovis* BCG By the term "few IS6110 sequences inserted in the genome", it is meant less than ten copies in the genome of *M. tuberculosis*, more preferably less than 5 copies, for example less than two copies.

The nucleic acid fragment of the invention is preferably selected from the group consisting of:

a) SEQ ID No 4;

b) Nucleic acid having a sequence fully complementary to SEQ ID No 4.

c) Nucleic acid fragment comprising at least 8, 12, 15, 20, 25, 30, 50, 100, 250, 500, 750, 1000, 1500, 2000, 2500, 3000 consecutive nucleotides of SEQ ID No 4;

d) Nucleic acid having at least 90% sequence identity after optimal alignment with a sequence defined in a) or b);

e) Nucleic acid that hybridizes under stringent conditions with the nucleic acid defined in a) or b).

In embodiments, the stringent conditions under which a sequence according to the invention is determined are conditions which are no less stringent than 5×SSPE, 2×Denhardt's solution, and 0.5% (w/v) sodium dodecyl sulfate at 65° C. More stringent conditions can be utilized by the ordinary artisan, and the proper conditions for a given assay can be easily and rapidly determined without undue or excessive experimentation. As an illustrative embodiment, the stringent hybridization conditions used in order to specifically detect a polynucleotide according to the present invention are advantageously the following: pre-bybridization and hybridization are performed at 65° C. in a mixture containing:

5×SSPE (1×SSPE is 3 M NaCl, 30 mM tri-sodium citrate)

2×Denhardt's solution 0.5% (w/v) sodium dodecyl sulfate (SDS)

100 μg $ml^{-1}$ salmon sperm DNA.

The washings are performed as follows:

two washings at laboratory temperature (approximately 21-25° C.) for 10 min. in the presence of 2×SSPE and 0.1% SDS; and one washing at 65° C. for 15 min. in the presence of 1×SSPE and 0.1% SDS.

The invention also encompasses the isolated or purified nucleic acid of the invention wherein said nucleic acid comprises at least a deletion of a nucleic acid fragment as defined above. Preferably, such an isolated or purified nucleic acid of the invention is the SEQ ID No 21 that corresponds to SEQ ID No 1 in which SEQ ID No 4 is deleted (absent).

Polynucleotides of the invention can be characterized by the percentage of identity they show with the sequences disclosed herein. For example, polynucleotides having at least 90% identity with the polynucleotides of the invention, particularly those sequences of the sequence listing, are encompassed by the invention. Preferably, the sequences show at least 90% identity with those of the sequence listing. More preferably, they show at least 92% identity, for example 95% or 99% identity. The skilled artisan can identify sequences according to the invention through the use of the sequence analysis software BLAST (see for example, Coffin et al., eds., "*Retroviruses*", Cold Spring Harbor Laboratory Press, pp. 723-755). Percent identity is calculated using the BLAST sequence analysis program suite, Version 2, available at the NCBI (NIH). All default parameters are used. BLAST (Basic Local Alignment Search Tool) is the heuristic search algorithm employed by the programs blastp, blastn, blastx, tblastn and tblastx, all of which are available through the BLAST analysis software suite at the NCBI. These programs ascribe significance to their findings using the statistical methods of Karlin and Altschul (1990, 1993) with a few enhancements. Using this publicly available sequence analysis program suite, the skilled artisan can easily identify polynucleotides according to the present invention.

It is well within the skill of the ordinary artisan to identify regions of the nucleic acid sequence of the invention, which would be useful as a probe, primer, or other experimental, diagnostic, or therapeutic aid. For example, the ordinary artisan could utilize any of the widely available sequence analysis programs to select regions (fragments) of these sequences that are useful for hybridization assays such as Southern blots, Northern blots, DNA binding assays, and/or in vitro, in situ, or in vivo hybridizations. Additionally, the ordinary artisan, with the sequences of the present invention, can utilize widely available sequence analysis programs to identify regions that can be used as probes and primers, as well as for design of anti-sense molecules. The only practical limitation on the fragment chosen by the ordinary artisan is the ability of the fragment to be useful for the purpose for which it is chosen. For example, if the ordinary artisan wished to choose a hybridization probe, he would know how to choose one of sufficient length, and of sufficient stability, to give meaningful results. The conditions chosen would be those typically used in hybridization assays developed for nucleic acid fragments of the approximate chosen length.

Thus, the present invention provides short oligonucleotides, such as those useful as probes and primers. In embodiments, the probe and/or primer comprises 8 to 30 consecutive nucleotides of the polynucleotide according to the invention or the polynucleotide complementary thereto. Advantageously, a fragment as defined herein has a length of at least 8 nucleotides, which is approximately the minimal length that has been determined to allow specific hybridization. Preferably the nucleic fragment has a length of at least 12 nucleotides and more preferably 20 consecutive nucleotides of any of SEQ ID No 1 or SEQ ID No 4. The sequence of the oligonucleotide can be any of the many possible sequences according to the invention. Preferably, the sequence is selected from the following group SEQ ID No 13, SEQ ID No 14, SEQ ID No 15, SEQ ID No 16, SEQ ID No 17, SEQ ID No 18. More precisely, the primers SEQ ID No 13, SEQ ID No 14, SEQ ID No 15 and SEQ ID No 16 are contained in the nucleic acid fragment SEQ ID No 4. The primers SEQ ID No 17 and SEQ ID No 18 are contained in the nucleic acid sequence SEQ ID No 1 and are flanking the nucleic acid fragment of SEQ ID No 4 (see FIG. 5).

Thus, the polynucleotides of SEQ ID No 1 and SEQ ID No 4, and their fragments, can be used to select nucleotide primers, notably for an amplification reaction, such as the amplification reactions further described.

PCR is described in U.S. Pat. No. 4,683,202, which is incorporated in its entirety herein. The amplified fragments may be identified by agarose or polyacrylamide gel electrophoresis, by a capillary electrophoresis, or alternatively by a chromatography technique (gel filtration, hydrophobic chromatography, or ion exchange chromatography). The specificity of the amplification can be ensured by a molecular hybridization using as nucleic probes the polynucleotides of SEQ ID No 1 or SEQ ID No 4, and their fragments, oligonucleotides that are complementary to these polynucleotides or fragments thereof, or their amplification products themselves, and/or even by DNA sequencing.

The following other techniques related to nucleic acid amplification may also be used and are generally preferred to the PCR technique. The Strand Displacement Amplification (SDA) technique is an isothermal amplification technique based on the ability of a restriction enzyme to cleave one of the strands at a recognition site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA amplification technique is more easily performed than PCR (a single thermostatted water bath device is necessary), and is faster than the other amplification methods. Thus, the present invention also comprises using the nucleic acid fragments according to the invention (primers) in a method of DNA or RNA amplification according to the SDA technique.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

The non-labeled polynucleotides or oligonucleotides of the invention can be directly used as probes. Nevertheless, the polynucleotides or oligonucleotides are generally labeled with a radioactive element ($^{32}P$, $^{35}S$, $^{3}H$, $^{125}I$) or by a non-isotopic molecule (for example, biotin, acetylaminofluorene, digoxigenin, 5-bromodesoxyuridine, fluorescein) in order to generate probes that are useful for numerous applications. Examples of non-radioactive labeling of nucleic acid fragments are described in French patent No FR 78 10975 and by Urdea et al (1988, *Nucleic Acids Research* 11:4937-4957) or Sanchez-Pescador et al. (1988, *J. Clin. Microbiol.* 26(10): 1934-1938), the disclosures of which are hereby incorporated in their entirety. Other labeling techniques can also be used, such as those described in French patents FR 2 422 956 and FR 2 518 755. The hybridization step may be performed in different ways. See, for example, Matthews et al., 1988, *Anal. Biochem.* 169:1-25. A general method comprises immobilizing the nucleic acid that has been extracted from the biological sample on a substrate (for example, nitrocellulose, nylon, polystyrene) and then incubating, in defined conditions, the target nucleic acid with the probe. Subsequent to the hybridization step, the excess amount of the specific probe is discarded and the hybrid molecules formed are detected by an appropriate method (radioactivity, fluorescence or enzyme activity measurement, etc.).

Amplified nucleotide fragments are useful, among other things, as probes used in hybridization reactions in order to detect the presence of one polynucleotide according to the present invention or in order to detect mutations. The primers may also be used as oligonucleotide probes to specifically detect a polynucleotide according to the invention.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix may be a material able to act as an electron donor, the detection of the matrix positions in which an hybridization has occurred being subsequently determined by an electronic device. Such matrix libraries of probes and methods of specific detection of a target nucleic acid is described in the European patent application No EP-0 713 016 (Affymax technologies) and also in the U.S. Pat. No. 5,202,231 (Drmanac). Since almost the whole length of a mycobacterial chromosome is covered by BAC-based genomic DNA library (i.e. 97% of the *M. tuberculosis* chromosome is covered by the BAC library I-1945), these DNA libraries will play an important role in a plurality of post-genomic applications, such as in mycobacterial gene expression studies where the canonical set of BACs could be used as a matrix for hybridization studies. Thus it is also in the scope of the invention to provide a nucleic acid chips, more precisely a DNA chips or a protein chips that respectively comprises a nucleic acid or a polypeptide of the invention.

The present invention is also providing a vector comprising the isolated DNA molecule of the invention. A "vector" is a replicon in which another polynucleotide segment is attached, so as to bring the replication and/or expression to the attached segment. A vector can have one or more restriction endonuclease recognition sites at which the DNA sequences can be cut in a determinable fashion without loss of an essential biological function of the vector, and into which a DNA fragment can be spliced in order to bring about its replication and cloning. Vectors can further provide primer sites (e.g. for PCR), transcriptional and/or translational initiation and/or regulation sites, recombinational signals, replicons, selectable markers, etc. Beside the use of homologous recombination or restriction enzymes to insert a desired DNA fragment into the vector, UDG cloning of PCR fragments (U.S. Pat. No. 5,334,575), T:A cloning, and the like can also be applied. The cloning vector can further contain a selectable marker suitable for use in the identification of cells transformed with the cloning vector.

The vector can be any useful vector known to the ordinary artisan, including, but not limited to, a cloning vector, an insertion vector, or an expression vector. Examples of vectors include plasmids, phages, cosmids, phagemid, yeast artificial chromosome (YAC), bacterial artificial chromosome (BAC), human artificial chromosome (HAC), viral vector, such as adenoviral vector, retroviral vector, and other DNA sequences which are able to replicate or to be replicated in vitro or in a host cell, or to convey a desired DNA segment to a desired location within a host cell.

According to a preferred embodiment of the invention, the recombinant vector is a BAC pBeloBAC11 in which the genomic region of *Mycobacterium bovis*-BCG 1173P3 that spans the region corresponding to the locus 1,760,753 bp to 1,830,364 bp in the genome of *M. tuberculosis* H37Rv has been inserted into the Hind III restriction site; this recombinant vector is named X229. In this region, the inventors have demonstrated the deletion of a 2153 bp fragment, corresponding to SEQ ID No 4, in the vast majority of *M. tuberculosis* strains excepted strains of *M. tuberculosis* having the sequence CTG at codon 463 of gene katG and having no or very few IS6110 sequences inserted in their genome. That's the reason why the inventors named this deletion of 2153 bp TbD1 ("*M. tuberculosis* specific deletion 1"). TbD1 is flanked by the sequence GGC CTG GTC AAA CGC GGC TGG ATG CTG (SEQ ID NO: 23) and AGA TCC GTC TTT GAC ACG ATC GAC G (SEQ ID NO: 24). External primers hybridizing with such sequences outside TbD1 or the complementary sequences thereof can be used for the amplification of TbD1 to check for the presence or the absence of the deletion of the TbD1. The inventors design for example the following primers:

5'-CTA CCT CAT CTT CCG GTC CA-3' (SEQ ID N$^O$ 17)

5'-CAT AGA TCC CGG ACA TGG TG-3' (SEQ ID N$^O$ 18)

In order to get a specific 500 pb probe for hybridization experiments, a PCR amplification of a fragment comprised in TbD1 may be realized by using the plasmid X229 as a matrix. The amplification of a fragment of approximately 500 bp contained in TbD1 can be performed by using the following primers:

5'-CGT TCA ACC CCA AAC AGG TA-3' (SEQ ID N$^O$ 13)

5'-AAT CGA ACT CGT GGA ACA CC-3' (SEQ ID N$^O$ 14)

The amplification of a fragment of approximately 2,000 bp contained in TbD1 can be performed by using the following primers:

5'-ATT CAG CGT CTA TCG GTT GC-3' (SEQ ID N$^O$ 15)

5'-AGC AGC TCG GGA TAT CGT AG-3' (SEQ ID N$^O$ 16)

The PCR conditions are the following: denaturation 95° C. 1 min, then 35 cycles of amplification [95° C. during 30 seconds, 58° C. during 1 min], then elongation 72° C. during 4 min.

Thus, this invention also concerns a recombinant cell host which contains a polynucleotide or recombinant vector according to the invention. The cell host can be transformed or transfected with a polynucleotide or recombinant vector to provide transient, stable, or controlled expression of the desired polynucleotide. For example, the polynucleotide of interest can be subcloned into an expression plasmid at a cloning site downstream from a promoter in the plasmid and the plasmid can be introduced into a host cell where expression can occur. The recombinant host cell can be any suitable host known to the skilled artisan, such as a eukaryotic cell or a microorganism. For example, the host can be a cell selected from the group consisting of *Escherichia coli, Bacillus subtilis*, insect cells, and yeasts. According to a preferred embodiment of the invention, the recombinant cell host is a commercially available *Escherichia coli* DH10B (Gibco) containing the BAC named X229 previously described. This *Escherichia coli* DH10B (Gibco) containing the BAC named X229 has been deposited with the Collection Nationale de Cultures de Microorganisms (CNCM), Institut Pasteur, Paris, France, on Feb. 18, 2002 under number CNCM I-2799.

Another aspect of the invention is the product of expression of all or part of the nucleic acid according to the invention, including the nucleic acid fragment specifically deleted in the genome of *Mycobacterium tuberculosis*, excepted in *Mycobacterium tuberculosis* strains having the sequence CTG at codon 463 of gene katG and having no or very few IS6110 sequences inserted in their genome as defined previously. The expression "product of expression" is understood to mean any isolated or purified protein, polypeptide or polypeptide fragment resulting from the expression of all or part of the above-mentioned nucleotide sequences. Among those product of expression, one can cite the membrane protein mmpL6 corresponding to SEQ ID No 6, the membrane protein mmpS6 corresponding to SEQ ID No 3 or SEQ ID No 10 (the two sequences SEQ ID No 3 and SEQ ID No 10 are identical), and their truncated or rearranged forms due to the deletion of a nucleic acid fragment according to the invention. For example, SEQ ID No 8 is a truncated form of mmpL6 protein, SEQ ID No 12 is a truncated form of mmpS6 protein and SEQ ID No 22 is a fusion product [mmpS6-mmpL6] of both rearranged mmpL6 and mmpS6 proteins.

It is now easy to produce proteins in large amounts by genetic engineering techniques through the use of expression vectors, such as plasmids, phages, and phagemids. The polypeptide of the present invention can be produced by insertion of the appropriate polynucleotide into an appropriate expression vector at the appropriate position within the vector. Such manipulation of polynucleotides is well known and widely practiced by the ordinary artisan. The polypeptide can be produced from these recombinant vectors either in vitro or in vivo. All the isolated or purified nucleic acids encoding the polypeptide of the invention are in the scope of the invention. The polypeptide of the invention is a polypeptide encoded by a polynucleotide which hybridizes to any of SEQ ID No 1 or No 4 under stringent conditions, as defined herein.

More preferably, said isolated or purified nucleic acid according the invention is selected among:

- the mmpL6 gene of sequence SEQ ID No 5 contained in SEQ ID No 1 and encoding the mmpL6 protein of sequence SEQ ID No 6;
- the truncated form of mmppL6 gene of sequence SEQ ID No 7 contained in TbD1 of sequence SEQ ID No 4 and encoding a truncated form of mmpL6 protein of sequence SEQ ID No 8;

the mmpS6 gene of sequence SEQ ID No 9 contained in SEQ ID No 1 and encoding the mmpS6 protein of SEQ ID No 10;

the truncated form of mmpS6 gene of sequence SEQ ID No 11 contained in TbD1 of sequence SEQ ID No 4 and encoding a truncated form of mmpS6 protein of SEQ ID No 12.

the chimeric gene of SEQ ID No 21 issued from fusion of both truncated mmpS6 and mmpL6 genes due to the deletion of TbD1 in the genome of *M. tuberculosis* excepted strains of *M. tuberculosis* having the sequence CTG at codon 463 of gene katG and having no or very few IS6110 sequences inserted in their genome. This chimeric gene encodes the fusion polypeptide [mmpS6-mmpL6] of sequence SEQ ID No 22.

The present invention also provides a method for the discriminatory detection and identification of:

*Mycobacterium tuberculosis* excepted *Mycobacterium tuberculosis* strains having the sequence CTG at codon 463 of gene katG and having no or very few IS6110 sequences inserted in their genome; versus,

*Mycobacterium africanum, Mycobacterium canettii Mycobacterium microti, Mycobacterium bovis, Mycobacterium bovis* BCG in a biological sample, comprising the following steps:

a) isolation of the DNA from the biological sample to be analyzed or production of a cDNA from the RNA of the biological sample, b) detection of the nucleic acid sequences of the mycobacterium present in said biological sample, c) analysis for the presence or the absence of a nucleic acid fragment specifically deleted in the genome of *Mycobacterium tuberculosis*, excepted in *Mycobacterium tuberculosis* strains having the sequence CTG at codon 463 of gene katG and having no or very few IS6110 sequences inserted in their genome, as previously described.

By a biological sample according to the present invention, it is notably intended a biological fluid, such as sputum, saliva, plasma, blood, urine or sperm, or a tissue, such as a biopsy.

Analysis of the desired sequences may, for example, be carried out by agarose gel electrophoresis. If the presence of a DNA fragment migrating to the expected site is observed, it can be concluded that the analyzed sample contained mycobacterial DNA. This analysis can also be carried out by the molecular hybridization technique using a nucleic probe. This probe will be advantageously labeled with a nonradioactive (cold probe) or radioactive element. Advantageously, the detection of the mycobacterial DNA sequences will be carried out using nucleotide sequences complementary to said DNA sequences. By way of example, they may include labeled or nonlabeled nucleotide probes; they may also include primers for amplification. The amplification technique used may be PCR but also other alternative techniques such as the SDA (Strand Displacement Amplification) technique, the TAS technique (Transcription-based Amplification System), the NASBA (Nucleic Acid Sequence Based Amplification) technique or the TMA (Transcription Mediated Amplification) technique.

The primers in accordance with the invention have a nucleotide sequence chosen from the group comprising SEQ ID No 13, SEQ ID No 14, SEQ ID No 15, SEQ ID No 16, SEQ ID No 17, SEQ ID No 18. The primers SEQ ID No 13, SEQ ID No 14, SEQ ID No 15 and SEQ ID No 16 are contained in the nucleic acid fragment SEQ ID No 4, and the primers SEQ ID No 17 and SEQ ID No 18 are contained in the nucleic acid of the invention SEQ ID No 1 but not in the nucleic acid fragment SEQ ID No 4.

In a variant, the subject of the invention is also a method for the discriminatory detection and identification of:

*Mycobacterium tuberculosis* excepted *Mycobacterium tuberculosis* strains having the sequence CTG at codon 463 of gene katG and having no or very few IS6110 sequences inserted in their genome; versus,

*Mycobacterium africanum, Mycobacterium canettii, Mycobacterium microti, Mycobacterium bovis, Mycobacterium bovis BCG* in a biological sample, comprising the following steps:

a) bringing the biological sample to be analyzed into contact with at least one pair of primers as defined above, the DNA contained in the sample having been, where appropriate, made accessible to the hybridization beforehand, b) amplification of the DNA of the mycobacterium, c) visualization of the amplification of the DNA fragments.

The amplified fragments may be identified by agarose or polyacrylamide gel electrophoresis by capillary electrophoresis or by a chromatographic technique (gel filtration, hydrophobic chromatography or ion-exchange chromatography). The specification of the amplification may be controlled by molecular hybridization using probes, plasmids containing these sequences or their product of amplification. The amplified nucleotide fragments may be used as reagent in hybridization reactions in order to detect the presence, in a biological sample, of a target nucleic acid having sequences complementary to those of said amplified nucleotide fragments. These probes and amplicons may be labeled or otherwise with radioactive elements or with nonradioactive molecules such as enzymes or fluorescent elements.

The subject of the present invention is also a kit for the discriminatory detection and identification of:

*Mycobacterium tuberculosis* excepted *Mycobacterium tuberculosis* strains having the sequence CTG at codon 463 of gene katG and having no or very few IS6110 sequences inserted in their genome; versus,

*Mycobacterium africanum, Mycobacterium canettii, Mycobacterium microti, Mycobacterium bovis, Mycobacterium bovis* BCG in a biological sample, in a biological sample comprising the following elements:

a) at least one pair of primers as defined previously, b) the reagents necessary to carry out a DNA amplification reaction, c) optionally, the necessary components which make it possible to verify or compare the sequence and/or the size of the amplified fragment.

Indeed, in the context of the present invention, depending on the pair of primers used, it is possible to obtain very different results. Thus, the use of primers which are contained in the TbD1 deletion, such as for example SEQ ID No 13, SEQ ID No 14, SEQ ID No 15, SEQ ID No 16, is such that no amplification product is detectable in *M. tuberculosis* excepted in strains having the sequence CTG at codon 463 of gene katG and having no or very few IS6110 sequences in their genome, and that amplification product is detectable in *Mycobacterium africanum, Mycobacterium canettii, Mycobacterium microti, Mycobacterium bovis, Mycobacterium bovis* BCG, *Mycobacterium tuberculosis* having the sequence CTG at codon 463 of gene katG and having no or very few IS6110 sequences inserted in their genome. The use of a pair of primers outside the TbD1 deletion such as SEQ ID No 17 and SEQ ID No 18 is likely to give rise to an amplicon in *Mycobacterium africanum, Mycobacterium canettii, Mycobacterium microti, Mycobacterium bovis, Mycobacterium bovis* BCG, *Mycobacterium tuberculosis* having the sequence CTG at codon 463 of gene katG and having no or very few IS6110 sequences inserted in their genome, of about 2100 bp whereas the use of the pair of primers outside the TbD1 deletion will give rise in *M. tuberculosis* excepted in strains having the sequence CTG at codon 463 of gene katG and having no or very few IS6110 sequences inserted in their genome, to an amplicon of about few bp.

More generally, the invention pertains to the use of at least one pair of primers as defined previously for the amplification of a DNA sequence from *Mycobacterium tuberculosis* or *Mycobacterium africanum, Mycobacterium canettii, Mycobacterium microti, Mycobacterium bovis, Mycobacterium bovis* BCG, *Mycobacterium tuberculosis* having the sequence CTG at codon 463 of gene katG and having no or very few IS6110 sequences inserted in their genome.

Indeed, the subject of the present invention is also a method for the in vitro discriminatory detection of antibodies directed against *Mycobacterium tuberculosis* excepted *Mycobacterium tuberculosis* having the sequence CTG at codon 463 of gene katG and having no or very few IS6110 sequences inserted in their genome versus antibodies directed against *Mycobacterium africanum, Mycobacterium canettii, Mycobacterium microti, Mycobacterium bovis, Mycobacterium bovis* BCG, *Mycobacterium tuberculosis* having the sequence CTG at codon 463 of gene katG and having no or very few IS6110 sequences inserted in their genome, in a biological sample, comprising the following steps:

a) bringing the biological sample into contact with at least one product of expression of all or part of the nucleic acid fragment specifically deleted in *M. tuberculosis* excepted in strains of *M. tuberculosis* having the sequence CTG at codon 463 of gene katG and having no or very few IS6110 sequences inserted in their genome, as previously defined, b) detecting the antigen-antibody complex formed.

The subject of the present invention is also a method for the in vitro discriminatory detection of a vaccination with *Mycobacterium bovis* BCG, an infection by *M. bovis, M. canettii, M. microti, M. africanum* or *M. tuberculosis* strains having the sequence CTG at codon 463 of gene katG and having no or very few IS6110 sequences inserted in their genome, versus an infection by *Mycobacterium tuberculosis*, excepted by *Mycobacterium tuberculosis* strains having the sequence CTG at codon 463 of gene katG and having no or very few IS6110 sequences inserted in their genome in a mammal, comprising the following steps:

a) preparation of a biological sample containing cells, more particularly cells of the immune system of said mammal and more particularly T cells, b) incubation of the biological sample of step a) with at least one product of expression of all or part of the nucleic acid fragment specifically deleted in *M. tuberculosis* excepted in strains of *M. tuberculosis* having the sequence CTG at codon 463 of gene katG and having no or very few IS6110 sequences inserted in their genome, as previously defined, c) detection of a cellular reaction indicating prior sensitization of the mammal to said product, in particular cell proliferation and/or synthesis of proteins such as gamma-interferon. Cell proliferation may be measured, for example, by incorporating $^3$H-Thymidine.

The invention also relates to a kit for the in vitro discriminatory diagnosis of a vaccination with *M. bovis* BCG, an infection by *M. bovis, M. canettii, M. microti, M. africanum* versus an infection by *M. tuberculosis* excepted by strains having the sequence CTG at codon 463 of gene katG and having no or very few IS6110 sequences inserted in their genome, in a mammal comprising:

a) a product of expression of all or part of the nucleic acid fragment specifically deleted in *M. tuberculosis* excepted in strains of *M. tuberculosis* having the sequence CTG at codon 463 of gene katG and having no or very few IS6110 sequences inserted in their genome, as previously defined, b) where appropriate, the reagents for the constitution of the medium suitable for the immunological reaction, c) the reagents allowing the detection of the antigen-antibody complexes produced by the immunological reaction, d) where appropriate, a reference biological sample (negative control) free of antibodies recognized by said product, e) where appropriate, a reference biological sample (positive control) containing a predetermined quantity of antibodies recognized by said product.

The reagents allowing the detection of the antigen-antibody complexes may carry a marker or may be capable of being recognized in turn by a labeled reagent, more particularly in the case where the antibody used is not labeled.

The subject of the invention is also mono- or polyclonal antibodies, their chimeric fragments or antibodies, capable of specifically recognizing a product of expression in accordance with the present invention.

The present invention therefore also relates to a method for the in vitro discriminatory detection of the presence of an antigen of *Mycobacterium tuberculosis* excepted of strains having the sequence CTG at codon 463 of gene katG and having no or very few IS6110 sequences inserted in their genome, versus the presence of an antigen of *Mycobacterium africanum, Mycobacterium canettii, Mycobacterium microti, Mycobacterium bovis, Mycobacterium bovis*-BCG and *Mycobacterium tuberculosis having the sequence CTG at codon* 463 of gene katG and having no or very few IS6110 sequences inserted in their genome, in a biological sample comprising the following steps:

a) bringing the biological sample into contact with an antibody of the invention, b) detecting the antigen-antibody complex formed.

The invention also relates to a kit for the discriminatory detection of the presence of an antigen of *Mycobacterium tuberculosis* excepted strains of *M. tuberculosis* having the sequence CTG at codon 463 of gene katG and having no or very few IS6110 sequences inserted in their genome versus the presence of an antigen of *Mycobacterium africanum, Mycobacterium canettii, Mycobacterium microti, Mycobacterium bovis, Mycobacterium bovis* BCG, *Mycobacterium tuberculosis* having the sequence CTG at codon 463 of gene katG and having no or very few IS6110 sequences inserted in their genome, in a biological sample comprising the following steps:

a) an antibody as previously claimed, b) the reagents for constituting the medium suitable for the immunological reaction, c) the reagents allowing the detection of the antigen-antibody complexes produced by the immunological reaction.

The above-mentioned reagents are well known to a person skilled in the art who will have no difficulty adapting them to the context of the present invention.

The subject of the invention is also an immunogenic composition, characterized in that it comprises at least one product of expression in accordance with the invention. Such an immunogenic composition will be used to protect animals and humans against infections by *M. africanum, M. bovis, M. canettii, M. microti* and *M. tuberculosis.*

In a particular embodiment, such an immunogenic composition will comprise a product of expression of all or part of the nucleic fragment specifically deleted in the genome of *Mycobacterium tuberculosis*, excepted in *Mycobacterium tuberculosis* strains having the sequence CTG at codon 463 of gene katG and having no or very few IS6110 sequences inserted in their genome. And in a preferable embodiment, such an immunogenic composition will comprise a product of expression of all or part of TbD1. In this case, such an immunogenic composition will be used to protect animals and humans against infections by *M. africanum, M. bovis, M. canettii, M. microti* and *M. tuberculosis* strains having the sequence CTG at codon 463 of gene katG and having no or very few IS6110 sequences inserted in their genome.

In an other particular embodiment, such an immunogenic composition will comprise the fusion product [mmpS6-mmpL6] of SEQ ID No 22. This fusion product is due to the absence of TbD1 in *M. tuberculosis* excepted strains having the sequence CTG at codon 463 of gene katG and having no or very few IS6110 sequences inserted in their genome. An immunogenic composition comprising this fusion product will be used to protect animals and humans specifically against infection by the vast majority of *M. tuberculosis* strains excepted strains having the sequence CTG at codon 463 of gene katG and having no or very few IS6110 sequences inserted in their genome.

Advantageously, the immunogenic composition in accordance with the invention enters into the composition of a vaccine when it is provided in combination with a pharmaceutically acceptable vehicle and optionally with one or more immunity adjuvant(s) such as alum or a representative of the family of muramylpeptides or incomplete Freund's adjuvant.

The invention also relates to a vaccine comprising at least one product of expression in accordance with the invention in combination with a pharmaceutically compatible vehicle and, where appropriate, one or more appropriate immunity adjuvant(s).

The invention also provide an in vitro method for the detection and identification of *Mycobacterium tuberculosis* excepted *Mycobacterium tuberculosis* strains having the sequence CTG at codon 463 of gene katG and having no or very few IS6110 sequences inserted in their genome in a biological sample, comprising the following steps:

a) isolation of the DNA from the biological sample to be analyzed or production of a cDNA from the RNA of the biological sample, b) detection of the nucleic acid sequences of the *mycobacterium* present in said biological sample, c) analysis for the presence or the absence of a nucleic acid fragment of the invention.

In another embodiment, the invention provides an in vitro method for the detection and identification of *Mycobacterium tuberculosis* excepted *Mycobacterium tuberculosis* strains having the sequence CTG at codon 463 of gene katG and having no or very few IS6110 sequences inserted in their genome in a biological sample, comprising the following steps:

a) bringing the biological sample to be analyzed into contact with at least one pair of primers selected among nucleic acid fragments of the invention, and more preferably selected among the primers chosen from the group comprising SEQ ID No 13, SEQ ID No 14, SEQ ID No 15, SEQ ID No 16, SEQ ID No 17, SEQ ID No 18, the DNA contained in the sample having been, where appropriate, made accessible to the hybridization beforehand, b) amplification of the DNA of the *mycobacterium,* c) visualization of the amplification of the DNA fragments.

The invention also provides a kit for the detection and identification of *Mycobacterium tuberculosis* excepted *Mycobacterium tuberculosis* strains having the sequence CTG at codon 463 of gene katG and having no or very few IS6110 sequences inserted in their genome in a biological sample, comprising the following elements:

a) at least one pair of primers selected among nucleic acid fragments of the invention, and more preferably selected among the primers chosen from the group comprising SEQ ID No 13, SEQ ID No 14, SEQ ID No 15, SEQ ID No 16, SEQ ID No 17, SEQ ID No 18, b) the reagents necessary to carry out a DNA amplification reaction, c) optionally, the necessary components which make it possible to verify or compare the sequence and/or the size of the amplified fragment.

The invention also relates to a method for the in vitro detection of antibodies directed against *Mycobacterium tuberculosis* excepted *Mycobacterium tuberculosis* strains having the sequence CTG at codon 463 of gene katG and having no or very few IS6110 sequences inserted in their genome, in a biological sample, comprising the following steps:

a) bringing the biological sample into contact with at least one product of expression of all or part of the nucleic acid fragment specifically deleted in *M. tuberculosis* excepted in strains of *M. tuberculosis* having the sequence CTG at codon 463 of gene katG and having no or very few IS6110 sequences inserted in their genome, b) detecting the antigen-antibody complex formed.

It is also a goal of the invention to use the TbD1 deletion as a genetic marker for the differentiation of *Mycobacterium* strains of *Mycobacterium* complex.

It is also a goal of the invention to use mmpL6$^{551}$ polymorphism as a genetic marker for the differentiation of *Mycobacterium* strains of *Mycobacterium* complex.

The use of such genetic marker(s) in association with at least one genetic marker selected among RD1, RD2, RD3, RD4, RD5, RD6, RD7, RD8, RD9, RD10, RD11, RD13, RD14, RvD1, RvD2, RvD3, RvD4, RvD5, katG$^{463}$, gyrA$^{95}$, oxyR'$^{285}$, pncA$^{57}$ and the specific insertion element of *M. canettii* (IS *canettii*) allows the differentiation of *Mycobacterium* strains of *Mycobacterium* complex (see example 4).

The present invention provides an in vitro method for the detection and identification of *Mycobacteria* from the *Mycobacterium* complex in a biological sample, comprising the following steps:

a) analysis for the presence or the absence of a nucleic acid fragment specifically deleted in *M. tuberculosis* excepted in strains of *M. tuberculosis* having the sequence CTG at codon 463 of gene katG and having no or very few IS6110 sequences inserted in their genome, and b) analysis of at least one additional genetic marker selected among RD1, RD2, RD3, RD4, RD5, RD6, RD7, RD8, RD9, RD10, RD11, RD13, RD14, RvD1, RvD2, RvD3, RvD4, RvD5, katG$^{463}$, gyrA$^{95}$, oxyR'$^{285}$, pncA$^{57}$, the specific insertion element of *M. canettii.*

In a preferred embodiment, two additional markers are used, preferably RD4 and RD9. The analysis is performed by a technique selected among sequence hybridization, nucleic acid amplification, antigen-antibody complex.

It is also a goal of the present invention to provide a kit for the detection and identification of *Mycobacteria* from the *Mycobacterium* complex in a biological sample comprising the following elements:

a) at least one pair of primers selected among nucleic acid fragments of the invention, and more preferably selected among the primers chosen from the group comprising SEQ ID No 13, SEQ ID No 14, SEQ ID No 15, SEQ ID No 16, SEQ ID No 17, SEQ ID No 18, b) at least one pair of primers specific of the genetic markers selected among RD1, RD2, RD3, RD4, RD5, RD6, RD7, RD8, RD9, RD10, RD11, RD13, RD14, RvD1, RvD2, RvD3, RvD4, RvD5, $katG^{463}$, $gyrA^{95}$, $oxyR'^{285}$, $pncA^{57}$, the specific insertion element of *M. canettii*.

c) the reagents necessary to carry out a DNA amplification reaction, d) optionally, the necessary components which make it possible to verify or compare the sequence and/or the size of the amplified fragment.

In a preferred embodiment, the kit comprises the following elements:

a) at least one pair of primers selected among nucleic acid fragments of the invention, and more preferably selected among the primers chosen from the group comprising SEQ ID No 13, SEQ ID No 14, SEQ ID No 15, SEQ ID No 16, SEQ ID No 17, SEQ ID No 18, b) one pair of primers specific of the genetic marker RD4, c) one pair of primers specific of the genetic marker RD9, d) the reagents necessary to carry out a DNA amplification reaction, e) optionally, the necessary components which make it possible to verify or compare the sequence and/or the size of the amplified fragment.

The figures and examples presented below are provided as further guide to the practitioner of ordinary skill in the art and are not to be construed as limiting the invention in anyway.

FIGURES

FIG. 1: Amplicons obtained from strains that have the indicated genomic region present or deleted. Sizes of amplicons in each group are uniform. Numbers correspond to strain designation used in Kremer et al. (1999, J. Clin Microbiol. 37: 2607-2618) (Ref. 8) and Supply et al (2001, J. Clin. Microbiol. 39: 3563-3571) (ref. 9).

Figure 2:
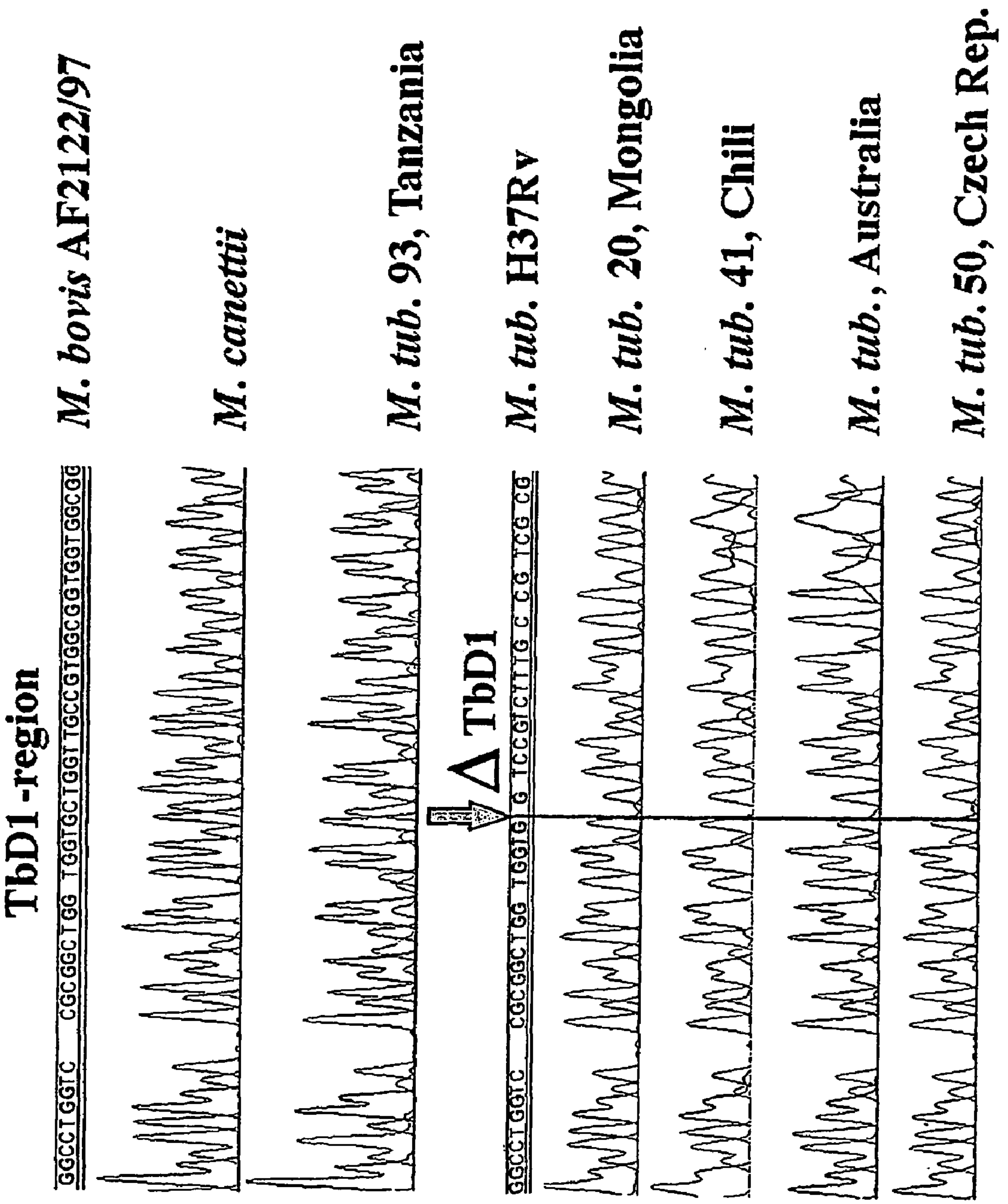

FIG. 2: Sequences (SEQ ID NOS 116-117) in the TbD1 region obtained from strains of various geographic regions.

refers to groups based on $katG^{c463}/gyrA^{c95}$ sequence polymorphism defined by Sreevatsan and colleagues (Ref. 2). Numbers correspond to strain designation used in Kremer et al. (1999, J. Clin Microbiol. 37: 2607-2618) (Ref. 8) and Supply et al (2001, J. Clin. Microbiol. 39: 3563-3571) (ref. 9).

Figure 3:
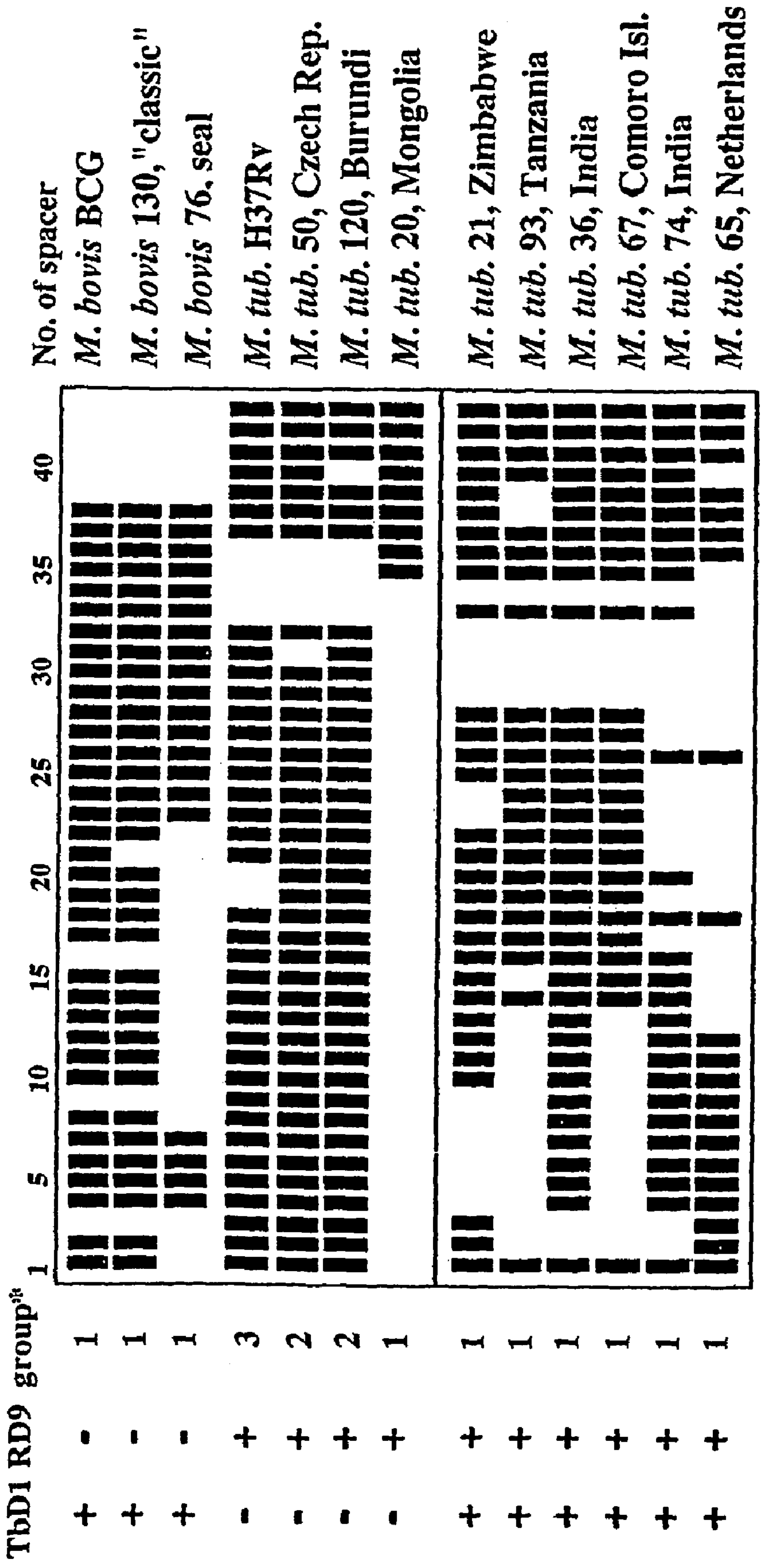

FIG. 3: Spoligotypes of selected *M. tuberculosis* and *M. bovis* strains. Numbers correspond to strain designation used in Kremer et al. (1999, J. Clin Microbiol. 37: 2607-2618) (Ref. 8) and Supply et al (2001, J. Clin. Microbiol. 39: 3563-3571) (ref. 9).

Figure 4:
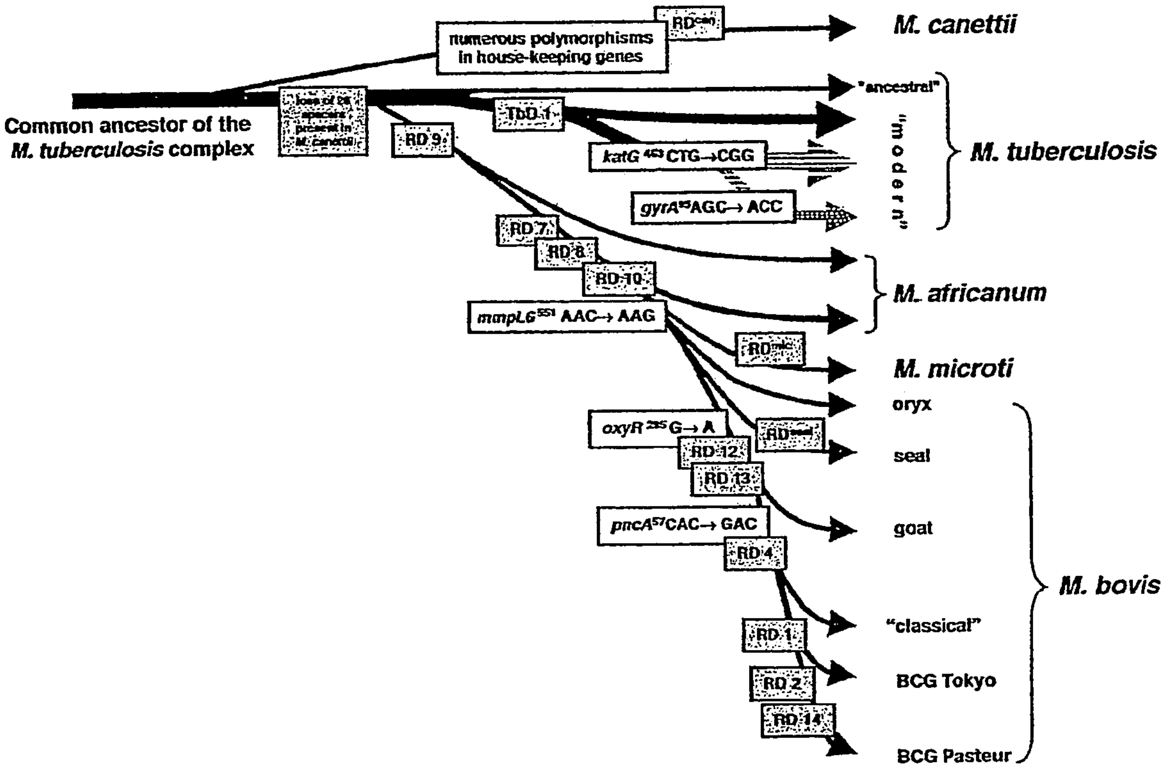

FIG. 4: Scheme of the proposed evolutionary pathway of the tubercle bacilli illustrating successive loss of DNA in certain lineages (grey boxes). The scheme is based on presence or absence of conserved deleted regions and on sequence polymorphisms in five selected genes. Note that the distances between certain branches may not correspond to actual phylogenetic differences calculated by other methods.

Dark arrows indicate that strains are characterized by $katG^{c463}$ CTG (Leu), $gyrA^{c95}$ ACC (Thr), typical for group 1 organisms. Arrows with white lines indicate that strains belong to group 2 characterized by $katG^{c463}$ CGG (Arg), $gyrA^{c95}$ ACC (Thr). The arrow with white boxes indicates that strains belong to group 3, characterized by $katG^{c463}$ CGG (Arg), $gyrA^{c95}$ AGC (Ser), as defined by Sreevatsan and colleagues (Sreevastan et al., 1997 Proc. Natl. Acad. Sci USA 151: 9869-9874) (Ref. 2).

Figure 5:
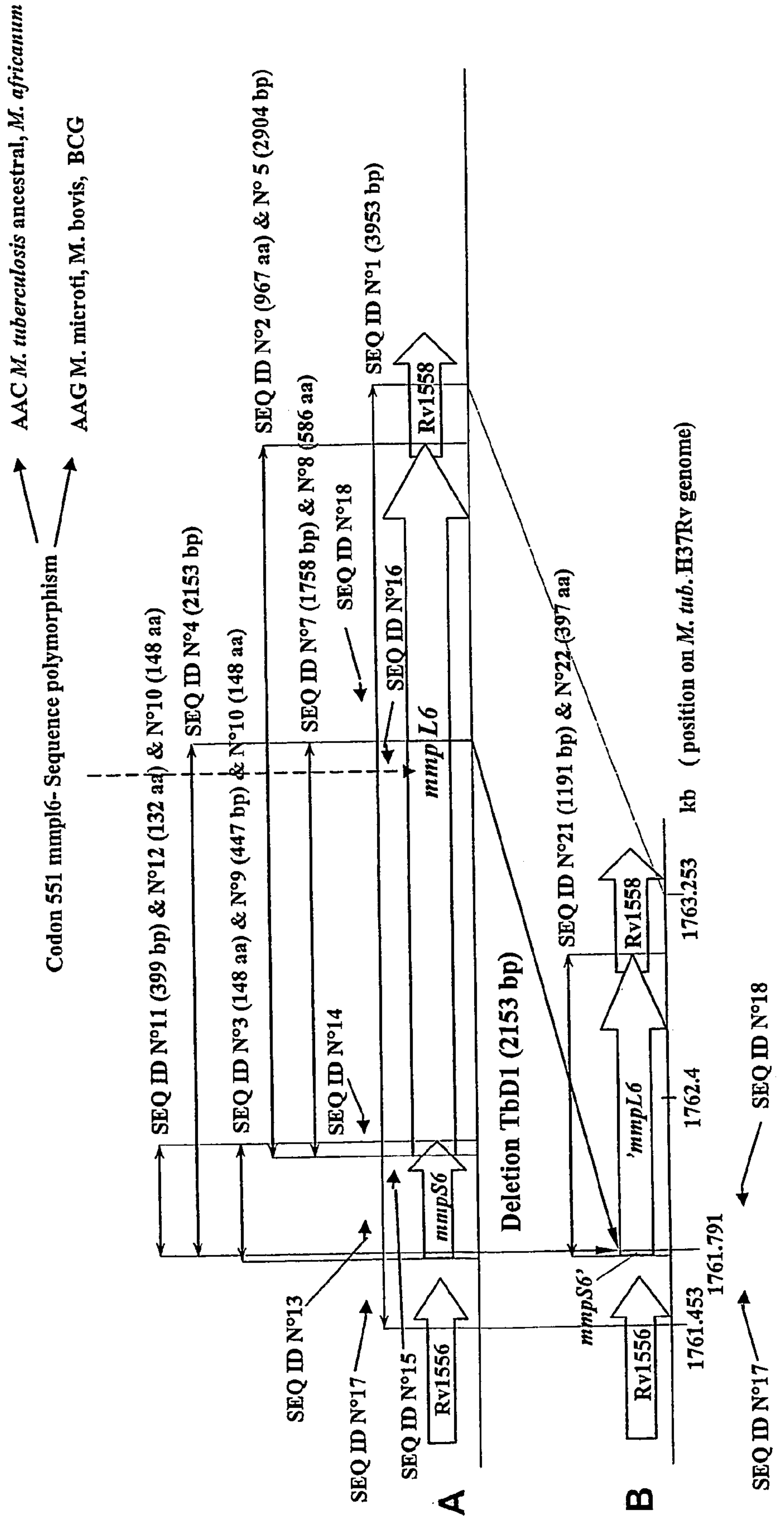

FIG. 5: Scheme of the TbD1 deletion and surrounding region in *Mycobacterium* complex.

A: Scheme of TbD1 and surrounding region in genome of *M. bovis, M. bovis* BCG, *M. africanum, M. canettii, M. microti* and ancestral strains of *M. tuberculosis* characterized by having the sequence CTG at codon 463 of gene katG and having no or very few IS6110 sequences inserted in their genome. The mmpL6 gene, the mmpS6 gene, the different primers, the different nucleic acid fragments and polypeptides coded by them are approximately localized in the region. The 2153 pb deletion named TbD1, specifically deleted in *M. tuberculosis* excepted in ancestral strains of *M. tuberculosis*, is delimited by its two end points.

B: Scheme of TbD1 and surrounding region in genome of *M. tuberculosis* excepted ancestral strains of *M. tuberculosis*. Positions of the TbD1 deletion and of the nucleic acid of sequence SEQ ID No 1 in the genome of *M. tuberculosis* strain H37Rv are marked below the scheme. An chimeric ORF [mmpS6-mmpL6] resulting from the absence of TbD1 is drawn, the sequence of this chimeric ORF, SEQ ID No 21 and the sequence of the encoded polypeptide, SEQ ID No 22, are approximately localized above the scheme.

FIG. 6: Sequence (SEQ ID NO: 19) of the specific insertion element in genome of *Mycobacterium canettii* strains. The beginning of this insertion element is at position 399 and the end of this insertion element is at position 2378. This insertion element contains the coding sequence of a putative transposase (sequence in bold characters, from position 517 to position 2307) that shows significant homology with a transposase of *Mycobacterium smegmatis*. This coding sequence is framed by two 20 bp inverted repeats (sequences underlined from position 399 to 418 and from position 2359 to 2378).

EXAMPLES

1. Material and Methods 1.1. Bacterial Strains: The 100 *M. tuberculosis* complex strains comprised 46 *M. tuberculosis* strains isolated in 30 countries, 14 *M. africanum* strains, 28 *M. bovis* strains originating in 5 countries, 2 *M. bovis* BCG vaccine strains (Pasteur and Japan), 5 *M. microti* strains, and 5 *M. canetti* strains. The strains were isolated from human and animal sources and were selected to represent a wide diversity including 60 strains that have been used in a multi-center study (8). The *M. africanum* strains were retrieved from the collection of the Wadsworth Center, New York State Department of Health, Albany, N.Y., whereas the majority of the *M. bovis* isolates came from the collection of the University of Zaragoza, Spain. Four *M. canettii* strains are from the culture collection of the Institut Pasteur, Paris, France. The strains have been extensively characterized by reference typing methods, i.e. IS6110 restriction fragment length polymorphism (RFLP) typing and spoligotyping. *M. tuberculosis* H37Rv, *M. tuberculosis* H37Ra, *M. tuberculosis* CDC1551, *M. bovis* AF2122/97, *M. microti* OV254, and *M. canettii* CIPT 140010059 were included as reference strains. DNA was prepared as previously described (10).

1.2. Genome Comparisons and Primer Design

For preliminary genome comparisons between *M tuberculosis* and *M bovis* websites [[http://]]genolist.pasteur.fr/TubercuList/ and [[http://www.]]sanger.ac.uklProjects/*M__bo-* vis/ as well as inhouse databases were used. For primer design, sequences inside or flanking RD and RvD regions were obtained from the same websites. Primers were designed using the primer 3 website [[http://www-]]genome.wi.mit.edu/cgi-bin/primer/primer3_www.cgi that would amplify ca. 500 base pair fragments in the reference strains (Table 1).

1.3. RD-PCR Analysis

Reactions were performed in 96 well plates and contained per reaction 1.25 μl of 10×PCR buffer (600 mM Tris HCl pH 8.8, 20 mM $MgCl_2$, 170 mM $(NH_4)_2SO_4$, 100 mM β-mercaptoethanol), 1.25 μl 20 mM nucleotide mix, 50 nM of each primer, 1-10 ng of template DNA, 10% DMSO, 0.2 units Taq polymerase (Gibco-BRL) and sterile distilled water to 12.5 μl. Thermal cycling was performed on a PTC-100 amplifier (MJ Inc.) with an initial denaturation step of 90 seconds at 95° C., followed by 35 cycles of 30 seconds at 95° C., 1 min at 58° C., and 4 min at 72° C.

1.4. Sequencing of Junction Regions (RDs, TbD1,) katG, gyrA, oxyR and pncA Genes PCR products were obtained as described above, using primers listed in Table 1.

For primer elimination, 6 μl PCR product was incubated with 1 unit of Shrimp Alkaline phosphatase (USB), 10 units of exonuclease I (USB), and 2 μl of 5× buffer (200 mM Tris HCl pH 8.8, 5 mM $MgCl_2$) for 15 min at 37° C. and then for 15 min at 80° C. To this reaction mixture 2 μl of Big Dye sequencing mix (Applied Biosystems), 2 μl (2 μM) of primer and 3 μl of 5× buffer (5 mM $MgCl_2$, 200 mM Tris HCl pH 8.8) were added and 35 cycles (96° C. for 30 sec; 56° C. for 15 sec; 60° C. for 4 min) performed in a thermocycler (MJ-research Inc., Watertown, Mass.). DNA was precipitated using 80 μl of 76% ethanol, centrifuged, rinsed with 70% ethanol, and dried. Reactions were dissolved in 2 μl of formamide/EDTA buffer, denatured and loaded onto 48 cm, 4% polyacrylamide gels and electrophoresis performed on 377 automated DNA sequencers (Applied Biosystems) for 10 to 12 h. Alternatively, reactions were dissolved in 0.3 mM EDTA buffer and subjected to automated sequencing on a 3700 DNA sequencer (Applied Biosystems). Reactions generally gave between 500-700 bp of unambiguous sequence.

1.5. Accession Numbers

The sequence of the TbD1 region from the ancestral *M. tuberculosis* strain No. 74 (Ref. 8) containing genes mmpS6 and mmpL6 was deposited in the EMBL database under accession No. AJ426486. Sequences bordering RD4, RD7, RD8, RD9 and RD10 in BCG are available under accession numbers AJ003103, AJ007301, AJ131210, Y18604, and AJ132559, respectively.

2. Experimental Data

The distribution of 20 variable regions resulting from insertion-deletion events in the genomes of the tubercle bacilli has been evaluated in a total of 100 strains of *Mycobacterium tuberculosis, M. africanum, M. canettii, M. microti* and *M. bovis*. This approach showed that the majority of these polymorphisms did not occur independently in the different strains of the *M. tuberculosis* complex but, rather, result from ancient, irreversible genetic events in common progenitor strains. Based on the presence or absence of an *M. tuberculosis* specific deletion (TbD1), *M. tuberculosis* strains can be divided into ancestral and "modern" strains, the latter comprising representatives of major epidemics like the Beijing, Haarlem and African *M. tuberculosis* clusters. Furthermore, successive loss of DNA, reflected by RD9 and other subsequent deletions, was identified for an evolutionary lineage represented by *M. africanum, M. microti* and *M. bovis* that diverged from the progenitor of the present *M. tuberculosis* strains before TbD1 occurred. These findings contradict the often-presented hypothesis that *M. tuberculosis*, the etiological agent of human tuberculosis evolved from *M. bovis*, the agent of bovine disease. *M. canettii* and ancestral *M. tuberculosis* strains lack none of these deleted regions and therefore appear to be direct descendants of tubercle bacilli that existed before the *M. africanum*→*M. bovis* lineage separated from the *M. tuberculosis* lineage. This suggests that the common ancestor of the tubercle bacilli resembled *M. tuberculosis* or *M. canettii* and could well have been a human pathogen already.

The mycobacteria grouped in the *M. tuberculosis* complex are characterized by 99.9% similarity at the nucleotide level and identical 16S rRNA sequences (1, 2) but differ widely in terms of their host tropisms, phenotypes and pathogenicity. Assuming that they are all derived from a common ancestor, it is intriguing that some are exclusive human (*M. tuberculosis, M. africanum, M. canettii*) or rodent pathogens (*M. microti*) whereas others have a wide host spectrum (*M. bovis*). What was the genetic organization of the last common ancestor of the tubercle bacilli and in which host did it live? Which genetic events may have contributed to the fact that the host spectrum is so different and often specific? Where and when did *M. tuberculosis* evolve? Answers to these questions are important for a better understanding of the pathogenicity and the global epidemiology of tuberculosis and may help to anticipate future trends in the spread of the disease.

Because of the unusually high degree of conservation in their housekeeping genes it has been suggested that the members of the *M. tuberculosis* complex underwent an evolutionary bottleneck at the time of speciation, estimated to have occurred roughly 15,000-20,000 years ago (2). It also has been speculated that *M. tuberculosis*, the most widespread etiological agent of human tuberculosis has evolved from *M. bovis*, the agent of bovine tuberculosis, by specific adaptation of an animal pathogen to the human host (3). However, both hypotheses were proposed before the whole genome sequence of *M. tuberculosis* (4) was available and before comparative genomics uncovered several variable genomic regions in the members of the *M. tuberculosis* complex. Differential hybridization arrays identified 14 regions (RD1-14) ranging in size from 2 to 12.7 kb that were absent from BCG Pasteur relative to *M. tuberculosis* H37Rv (5, 6). In parallel, six regions, RvD1-5, and TbD1, that were absent from the *M. tuberculosis* H37Rv genome relative to other members of the *M. tuberculosis* complex were revealed by comparative genomics approaches employing pulsed-field gel electrophoresis (PFGE) techniques (5, 7) and in silico comparisons of the near complete *M. bovis* AF2122/97 genome sequence and the *M. tuberculosis* H37Rv sequence.

In the present study the inventors have analyzed the distribution of these 20 variable regions situated around the genome (Table 1) in a representative and diverse set of 100 strains belonging to the *M. tuberculosis* complex. The strains were isolated from different hosts, from a broad range of geographic origins, and exhibit a wide spectrum of typing characteristics like IS6110 and spoligotype hybridization patterns or variable-number tandem repeats of mycobacterial interspersed repetitive units (MIRU-VNTR) (8, 9). The inventors have found striking evidence that deletion of certain variable genomic regions did not occur independently in the different strains of the *Mycobacterium* complex and, assuming that there is little or no recombination of chromosomal segments between the various lineages of the complex, this allows the inventors to propose a completely new scenario for the evolution of the *Mycobacterium* complex and the origin of human tuberculosis.

Variable Genomic Regions and their Occurrence in the Members of the *M. tuberculosis* complex.

The PCR screening assay for the 20 variable regions (Table 1) within 46 *M. tuberculosis,* 14 *M. africanum,* 5 *M. canettii,* 5 *M. microti,* 28 *M. bovis* and 2 BCG strains employed oligonucleotides internal to known RDs and RvDs, as well as oligonucleotides flanking these regions (Table 1). This approach generated a large data set that was robust, highly reliable, and internally controlled since PCR amplicons obtained with the internal primer pair correlated with the absence of an appropriately sized amplicon with the flanking primer-pair, and vice-versa.

According to the conservation of junction sequences flanking the variable regions three types of regions were distinguished, each having different importance as an evolutionary marker. The first type included mobile genetic elements, like the prophages phiRv1 (RD3) and phiRv2 (RD11) and insertion sequences IS1532 (RD6) and IS6110 (RD5), whose distribution in the tubercle bacilli was highly divergent (Table 2). The second type of deletion is mediated by homologous recombination between adjacent IS6110 insertion elements resulting in the loss of the intervening DNA segment (RvD2, RvD3, RvD4, and RvD5 (7)) and is variable from strain to strain (Table 2).

The third type includes deletions whose bordering genomic regions typically do not contain repetitive sequences. Often this type of deletion occurred in coding regions resulting in the truncation of genes that are still intact in other strains of the *M. tuberculosis* complex. The exact mechanism leading to this type of deletion remains obscure, but possibly rare strand slippage errors of DNA polymerase may have contributed to this event. As shown in detail below, RD1, RD2, RD4, RD7, RD8, RD9, RD10, RD12, RD13, RD14, and TbD1 are representatives of this third group whose distribution among the 100 strains allows us to propose an evolutionary scenario for the members of the *M. tuberculosis* complex, that identified *M. tuberculosis* and/or *M. canettii* as most closely related to the common ancestor of the tubercle bacilli.

2.1. *M. tuberculosis* Strains:

Investigation of the 46 *M. tuberculosis* strains by deletion analysis revealed that most RD regions were present in all *M. tuberculosis* strains tested (Table 2). Only regions RD3 and RD 11, corresponding to the two prophages phiRv1 and phiRv2 of *M. tuberculosis* H37Rv (4), RD6 containing the insertion sequence IS1532, and RD5 that is flanked by a copy of IS6110 (5) were absent in some strains. This is an important observation as it implies that *M. tuberculosis* strains are highly conserved with respect to RD1, RD2, RD4, RD7, RD8, RD9, RD10, RD12, RD13, and RD14, and that these RDs represent regions that can differentiate *M. tuberculosis* strains independent of their geographical origin and their typing characteristics from certain other members of the *M. tuberculosis* complex. Furthermore, this suggests that these regions may be involved in the host specificity of *M. tuberculosis.*

In contrast, the presence or absence of RvD regions in *M. tuberculosis* strains was variable. The region which showed the greatest variability was RvD2, since 18 from 46 tested *M. tuberculosis* strains did not carry the RvD2 region. Strains with a high copy number of IS6110 (>14) missed regions RvD2 to RvD5 more often than strains with only a few copies. As an example, all six tested strains belonging to the Beijing cluster (8) lacked regions RvD2 and RvD3. This is in agreement with the proposed involvement of recombination of two adjacent copies of IS6110 in this deletion event (7).

However, the most surprising finding concerning the RvD regions was that TbD1 was absent from 40 of the tested *M. tuberculosis* strains (87%), including representative strains from major epidemics such as the Haarlem, Beijing and Africa clusters (8). To accentuate this result we named this region "*M. tuberculosis* specific deletion 1" (TbD1). In silico sequence comparison of *M. tuberculosis* H37Rv with the corresponding section in *M. bovis* AF21122/97 revealed that in *M. bovis* this locus comprises two genes encoding membrane proteins belonging to a large family, whereas in *M. tuberculosis* H37Rv one of these genes (mmpS6) was absent and the second was truncated (mmpL6). Unlike the RvD2-RvD5 deletions, the TbD1 region is not flanked by a copy of IS6110 in *M. tuberculosis* H37Rv, suggesting that insertion elements were not involved in the deletion of the 2153 bp fragment. To further investigate whether the 40 *M. tuberculosis* strains lacking the TbD1 region had the same genomic organization of this locus as *M. tuberculosis* H37Rv, we amplified the TbD1-junction regions of the various strains by PCR using primers flanking the deleted region (Table 1). This approach showed that the size of the amplicons obtained from multiple strains was uniform (FIG. 1) and subsequent sequence analysis of the PCR products revealed that in all tested TbD1-deleted strains the sequence of the junction regions was identical to that of *M. tuberculosis* H37Rv (FIG. 2). The perfect conservation of the junction sequences in TbD1-deleted strains of wide geographical diversity suggests that the genetic event which resulted in the deletion occurred in a common progenitor. However, six *M. tuberculosis* strains, all characterized by very few or no copies of IS6110 and spoligotypes that resembled each other (FIG. 3) still had the TbD1 region present. Interestingly, these six strains were also clustered together by MIRU-VNTR analysis (9).

Analysis of partial gene sequences of oxyR, pncA, katG, and gyrA which have been described as variable between different tubercle bacilli (2, 11, 12, 13) revealed that all tested *M. tuberculosis* strains showed oxyR and pncA partial sequences typical for *M. tuberculosis* (oyxR-nucleotide 285 (oxyR$^{285}$):G, pncA-codon 57 (pncA$^{57}$: CAC). Based on the katG codon 463 (katG$^{463}$) and gyrA codon 95 (gyrA$^{95}$) sequence polymorphism, Sreevatsan and colleagues (2) defined three groups among the tubercle bacilli, group 1 showing katG$^{463}$ CTG (Leu), gyrA$^{95}$ ACC (Thr), group 2 exhibiting katG$^{463}$ CGG (Arg), gyrA$^{95}$ ACC (Thr), and group 3 showing katG$^{463}$ CGG (Arg), gyrA$^{95}$ AGC (Ser). According to this scheme, in our study 16 of the 46 tested *M. tuberculosis* strains belonged to group 1, whereas 27 strains belonged to group 2 and only 3 isolates to group 3. From the 40 strains that were deleted for region TbD1, 9 showed characteristics of group 1, including the strains belonging to the Beijing cluster, 28 of group 2, including the strains from the Haarlem and Africa clusters and 3 of group 3, including H37Rv and H37Ra. Most interestingly, all six *M. tuberculosis* strains where the TbD1 region was not deleted, contained a leucine (CTG) at katG$^{463}$, which was described as characteristic for ancestral *M. tuberculosis* strains (group 1) (2). As shown in FIG. 4, this suggests that during the evolution of *M. tuberculosis* the katG mutation at codon 463 CTG (Leu)→CGG (Arg) occurred in a progenitor strain that had region TbD1 deleted. This proposal is supported by the finding that strains belonging to group 1 may or may not have deleted region TbD1, whereas all 30 strains belonging to groups 2 and 3 lacked TbD1 (FIG. 4). Furthermore, all strains of groups 2 and 3 characteristically lacked spacer sequences 33-36 in the direct repeat (DR) region (FIG. 3). It appears that such spacers may be lost but not gained (14). Therefore, TbD1 deleted strains will be referred to hereafter as "modern" *M. tuberculosis* strains.

2.2. *M. canettii:*

*M. canettii* is a very rare smooth variant of *M. tuberculosis*, isolated usually from patients from, or with connection to, Africa. Although it shares identical 16S rRNA sequences with the other members of the *Mycobacterium* complex, *M. canettii* strains differ in many respects including polymorphisms in certain house-keeping genes, IS1081 copy number, colony morphology, and the lipid content of the cell wall (15, 16). Therefore, we were surprised to find that in *M. canettii* all the RD, RvD, and TbD1 regions except the prophages (phiRv1, phiRv2) were present. In contrast, we identified a region ($RDC^{can}$) being specifically absent from all five *M. canettii* strains that partially overlapped RD12 (FIG. 4).

The conservation of the RD, RvD, and TbD1 regions in the genome of *M. canettii* in conjunction with the many described and observed differences suggest that *M. canettii* diverged from the common ancestor of the *Mycobacterium* complex before RD, RvD and TbD1 occurred in the lineages of tubercle bacilli (FIG. 4). This hypothesis is supported by the finding that *M. canettii* was shown to carry 26 unique spacer sequences in the direct repeat region (14), that are no longer present in any other member of the *Mycobacterium* complex. An other specific feature of *M. canettii* is the presence of an insertion element whose sequence has been searched, by using PCR and hybridization approaches, without success in the other member strains of *Mycobacterium* complex (including *M. tuberculosis, M. bovis, M. africanum* and *M. microti*). This insertion element contained an ORF encoding a putative transposase framed by two inverted repeats. The sequence of this insertion element is represented in FIG. 6 and in SEQ ID No 19 where it begins at position 399 and ends at position 2378. The amino acids sequence of the putative transposase is drawn in SEQ ID No 20. As such, this insertion element can be used to differentiate between *M. tuberculosis* ancestral strains and *M. canettii* strains that may show the same TbD1, RD4 and RD9 profiles. Therefore, *M. canettii* represents a fascinating tubercle *bacillus*, whose detailed genomic analysis may reveal further insights into the evolution of *Mycobacterium* complex.

2.3. *M. africanum:*

The isolates designated as *M. africanum* studied here originate from West and East-African sources. 11 strains were isolated in Sierra Leone, Nigeria and Guinea and 2 strains in Uganda. One strain comes from the Netherlands.

For the 11 West African isolates, RD analysis indicated that these strains all lack the RD9 region containing cobL. Sequence analysis of the RD9 junction region showed that the genetic organization of this locus in West African strains was identical to that of *M. bovis* and *M. microti* in that the 5' part of cobL as well as the genes Rv2073c and Rv2074c were absent. In addition, six strains (2 from Sierra Leone, 4 from Guinea) also lacked RD7, RD8 and RD10 (Table 2). The junction sequences bordering RD7, RD8 and RD10, like those for RD9, were identical to those of *M. bovis* and *M. microti* strains. As regards the two prophages phiRv1 and phiRv2, the West African strains all contained phiRv2, whereas phiRv1 was absent. No variability was seen for the RvD regions. RvD1-RvD5 and TbD1 were present in all tested West African strains. This shows that *M. africanum* prevalent in West Africa can be differentiated from "modern" *M. tuberculosis* by at least two variable genetic markers, namely the absence of region RD9 and the presence of region TbD1.

In contrast, for East African *M. africanum* and for the isolate from the Netherlands, no genetic marker was found which could differentiate them from *M. tuberculosis* strains. With the exception of prophage phiRv1 (RD3) the 3 strains from Uganda and the Netherlands did not exhibit any of the RD deletions, but lacked the TbD1 region, as do "modern" *M. tuberculosis* strains. The absence of the TbD1 region was also confirmed by sequence analysis of the TbD1 junction region, which was found to be identical to that of TbD1 deleted *M. tuberculosis* strains. These results indicate a very close genetic relationship of these strains to *M. tuberculosis* and suggest that they should be regarded as *M. tuberculosis* rather than *M. africanum* strains.

2.4. *M. microti:*

*M. microti* strains were isolated in the 1930's from voles (17) and more recently from immuno-suppressed patients (18). These strains are characterized by an identical, characteristic spoligotype, but differ in their IS6110 profiles. Both, the vole and the human isolates, lacked regions RD7, RD8, RD9, and RD10 as well as a region that is specifically deleted from *M. microti* ($RD^{mic}$). $RD^{mic}$ was revealed by a detailed comparative genomics study of *M. microti* isolates (19) using clones from a *M. microti* Bacterial Artificial Chromosome (BAC) library. $RD^{mic}$ partially overlaps RD1 from BCG (data not shown). Furthermore, vole isolates missed part of the RD5 region, whereas this region was present in the human isolate. As the junction region of RD5 in *M. microti* was different to that in BCG (data not shown), RD5 was not used as an evolutionary marker.

2.5. *M. bovis* and *M. bovis* BCG:

*M. bovis* has a very large host spectrum infecting many mammalian species, including man. The collection of *M. bovis* strains that was screened for the RD and RvD regions consisted of 2 BCG strains and 18 "classical" *M. bovis* strains generally characterized by only one or two copies of IS6110 from bovine, llama and human sources in addition to three goat isolates, three seal isolates, two oryx isolates, and two *M. bovis* strains from humans that presented a higher number of IS6110 copies.

Excluding prophages, the distribution of RDs allowed us to differentiate five main groups among the tested *M. bovis* strains. The first group was formed by strains that lack RD7, RD8, RD9, and RD10. Representatives of this group are three seal isolates and two human isolates containing between three and five copies of IS6110 (data not shown). Two oryx isolates harboring between 17 and 20 copies of IS6110 formed the second group that lacked parts of RD5 in addition to RD7-RD10, and very closely resembled the *M. microti* isolates. However, they did not show $RD^{mic}$, the deletion characteristic of *M. microti* strains (data not shown). Analysis of partial oxyR and pncA sequences from strains belonging to groups one and two, showed sequence polymorphisms characteristic of *M. tuberculosis* strains ($oxyR^{285}$: G, $pncA^{57}$: CAC, Ref. 12, 13).

Group three consists of goat isolates that lack regions RD5, RD7, RD8, RD9, RD10, RD12, and RD13. As previously described by Aranaz and colleagues, these strains exhibited an adenosine at position 285 of the oxyR pseudogene that is specific for "classical" *M. bovis* strains whereas the sequence of the $pncA^{57}$ polymorphism was identical to that in *M. tuberculosis* (20). This is in good agreement with our results from sequence analysis (Table 2) and the finding that except for RD4, the goat isolates displayed the same deletions as "classical" *M. bovis* strains. Taken together, this suggests that the $oxyR^{285}$ mutation (G→A) occurred in *M. bovis* strains before RD4 was lost. Interestingly, the most common *M. bovis* strains ("classical" *M. bovis* (21)), isolated from cattle from Argentina, the Netherlands, the UK and Spain, as well as from humans (e. g. multi-drug resistant *M. bovis* from Spain (22)) showed the greatest number of RD deletions and appear to have undergone the greatest loss of DNA relative to other members of the *M. tuberculosis* complex. These lacked regions RD4, RD5, RD6, RD7, RD8, RD9, RD10, RD12 and RD13, confirming results obtained with reference strains (5, 6). These strains together with the two BCG strains were the only ones that showed the $pncA^{57}$ polymorphism GAC (Asp) in addition to the $oxyR^{285}$ mutation (G→A) characteristic of *M. bovis*. Analysis of BCG strains indicate that BCG lacked the same RD regions as "classical" *M. bovis* strains in addition to RD1, RD2 and RD14 which apparently occurred during and after the attenuation process (FIG. 4) (6, 23).

In contrast to RDs, the RvD regions were highly conserved in the *M. bovis* strains. With the exception of the two IS6110-rich oryx isolates, that lacked RvD2, RvD3 and RvD4, all other strains had the five RvD regions present. It is particularly noteworthy that TbD1 was present in all *M. bovis* strains.

However, except for the two human isolates, containing between three and five copies of IS6110 from group 1, strains designated as *M. bovis* showed a single nucleotide polymorphism in the TbD1 region at codon 551 (AAG) of the mmpL6 gene, relative to *M. canettii, M. africanum* and ancestral *M. tuberculosis* strains, which are characterized by codon AAC. Even the strains isolated from seals and from oryx with oxyR or pncA loci like those of *M. tuberculosis* and with fewer deleted regions than the classical *M. bovis* strains, showed the $mmpL6^{551}$ AAG polymorphism typical for *M. bovis* and *M. microti* (Table 2, FIG. 4). As such, this polymorphism could serve as a very useful genetic marker for the differentiation of strains that lack RD7, RD8, RD9, and RD10 and have been classified as *M. bovis* or *M. africanum*, but may differ from other strains of the same taxon.

3. Discussion

3.1. Origin of Human Tuberculosis

For many years, it was thought that human tuberculosis evolved from the bovine disease by adaptation of an animal pathogen to the human host (3). This hypothesis is based on the property of *M. tuberculosis* to be almost exclusively a human pathogen, whereas *M. bovis* has a much broader host range. However, the results from this study unambiguously show that *M. bovis* has undergone numerous deletions relative to *M. tuberculosis*. This is confirmed by the preliminary analysis of the near complete genome sequence of *M. bovis* AF2122/97, a "classical" *M. bovis* strain isolated from cattle, which revealed no new gene clusters that were confined specifically to *M. bovis*. This indicates that the genome of *M. bovis* is smaller than that of *M. tuberculosis* (24). It seems plausible that *M. bovis* is the final member of a separate lineage represented by *M. africanum* (RD9), *M. microti* (RD7, RD8, RD9, RD10) and *M. bovis* (RD4, RD5, RD7, RD8, RD9, RD10, RD12, RD13) (25) that branched from the progenitor of *M. tuberculosis* isolates. Successive loss of DNA may have contributed to clonal expansion and the appearance of more successful pathogens in certain new hosts.

Whether the progenitor of extant *M. tuberculosis* strains was already a human pathogen when the *M. africanum*→*M. bovis* lineage separated from the *M. tuberculosis* lineage is a subject for speculation. However, we have two reasons to believe that this was the case. Firstly, the six ancestral *M. tuberculosis* strains ($TbD1^+$, $RD9^+$) (FIG. 3) that resemble the last common ancestor before the separation of *M. tuberculosis* and *M. africanum* are all human pathogens. Secondly, *M. canettii*, which probably diverged from the common ancestor of today's *M. tuberculosis* strains prior to any other known member of the *M. tuberculosis* complex is also a human pathogen. Taken together, this means that those tubercle bacilli, which are thought to most closely resemble the progenitor of *M. tuberculosis* are human and not animal pathogens. It is also intriguing that most of these strains were of African or Indian origin (FIG. 3). It is likely that these ancestral strains predominantly originated from endemic foci (15, 26), whereas "modern" *M. tuberculosis* strains that have lost TbD1 may represent epidemic *M. tuberculosis* strains that were introduced into the same geographical regions more recently as a consequence of the worldwide spread of the tuberculosis epidemic.

3.2. The Evolutionary Timescale of the *M. tuberculosis* Complex

Because of the high sequence conservation in housekeeping genes, Sreevatsan et al. previously hypothesized that the tubercle bacilli encountered a major bottleneck 15,000-20,000 years ago (2). As the conservation of the TbD1 junction sequence in all tested TbD1 deleted strains suggests descendance from a single clone, the TbD1 deletion is a perfect indicator that "modern" *M. tuberculosis* strains that account for the vast majority of today's tuberculosis cases definitely underwent such a bottleneck and then spread around the world.

As described in detail in the results section, our analysis showed that the $katG^{463}$ CTG→CGG and the subsequent $gyrA^{95}$ ACC→AGC mutations, that were used by Sreevatsan and colleagues to designate groups 2 and 3 of their proposed evolutionary pathway of the tubercle bacilli (2), occurred in a lineage of *M. tuberculosis* strains that had already lost TbD1 (FIG. 4). Although deletions are more stable markers than point mutations, which may be subject to reversion, a perfect correlation of deletion and point mutation data was found for the tested strains.

This information, together with results from a recent study by Fletcher and colleagues (27), who have shown that *M. tuberculosis* DNAs amplified from naturally mummified Hungarian villagers from the $18^{th}$ and $19^{th}$ century belonged to $katG^{463}/gyrA^{95}$ groups 2 and 3, suggests that the TbD1 deletion occurred in the lineage of *M. tuberculosis* before the $18^{th}$ century. This could mean that the dramatic increase of tuberculosis cases later in the $18^{th}$ century in Europe mainly involved "modern" *M. tuberculosis* strains. In addition, it shows that *tuberculosis* was caused by *M. tuberculosis* and not by *M. bovis*, a fact which is also described for cases in rural medieval England (28).

There is good evidence that mycobacterial infections occurred in man several thousand years ago. We know that tuberculosis occurred in Egypt during the reign of the pharaohs because spinal and rib lesions pathognomonic of tuberculosis have been identified in mummies from that period (29). Identification of acid fast bacilli as well as PCR amplification of IS6110 from Peruvian mummies (30) also suggest that tuberculosis existed in pre-Columbian societies of Central and South America. To estimate when the TbD1 bottleneck occurred, it would now be very interesting to know whether the Egyptian and South American mummies carried *M. tuberculosis* DNA that had TbD1 deleted or not.

The other major bottleneck, which seems to have occurred for members of the *M. africanum*→*M. microti*→*M. bovis* lineage is reflected by RD9 and the subsequent RD7, RD8 and RD10 deletions (FIG. 4). These deletions seem to have occurred in the progenitor of tubercle bacilli that—today—show natural host spectra as diverse as humans in Africa, voles on the Orkney Isles (UK), seals in Argentina, goats in Spain, and badgers in the UK. For this reason it is difficult to imagine that spread and adaptation of RD9-deleted bacteria to their specific hosts could have appeared within the postulated 15,000-20,000 years of speciation of the *M. tuberculosis* complex.

However, more insight into this matter could be gained by RD analysis of ancient DNA samples, e. g. mycobacterial DNA isolated from a 17,000 year old bison skeleton (31). The *mycobacterium* whose DNA was amplified showed a spoligotype that was most closely related to patterns of *M. africanum* and could have been an early representative of the lineage *M. africanum*→*M. bovis*. With the TbD1 and RD9 junction sequences that we supply here, PCR analyses of ancient DNAs should enable very focused studies to be undertaken to learn more about the timescale within which the members of the *M. tuberculosis* complex have evolved.

3.3. Concluding Comments

Our study provides an overview of the diversity and conservation of variable regions in a broad range of tubercle bacilli. Deletion analysis of 100 strains from various hosts and countries has identified some evolutionarily "old" *M. canettii, M. tuberculosis* and *M. africanum*) strains, most of them of African origin, as well as "modern" *M. tuberculosis* strains, the latter including representatives from major epidemic clusters like Beijing, Haarlem and Africa. The use of deletion analysis in conjunction with molecular typing and analysis of specific mutations was shown to represent a very powerful approach for the study of the evolution of the tubercle bacilli and for the identification of evolutionary markers. In a more practical perspective, these regions, primarily RD9 and TbD1 but also RD1, RD2, RD4, RD7, RD8, RD10, RD12 and RD13 represent very interesting candidates for the development of powerful diagnostic tools for the rapid and unambiguous identification of members of the *M. tuberculosis* complex (32). This genetic approach for differentiation can now be used to replace the often confusing traditional division of the *M. tuberculosis* complex into rigidly defined subspecies.

Moreover, functional analyses will show whether the TbD1 deletion confers some selective advantage to "modern" *M. tuberculosis*, or whether other circumstances contributed to the pandemic of the TbD1 deleted *M. tuberculosis* strains.

Example 4

The members of the *M. tuberculosis* complex share an unusually high degree of conservation such that the commercially-available nucleic acid probes and amplification assays cannot differentiate these organisms. In addition conventional identification methods are often ambiguous, cumbersome and time consuming because of the slow growth of the organisms.

In the present invention the inventors, by a deletion analysis, solve the problem faced by clinical mycobacteriology laboratories for differentiation within the *M. tuberculosis* complex.

This approach allows to perform a diagnostic on a biological fluid by using at least three markers including TbD1. The following table 3 illustrates such a combination sufficient to realize the distinction between the members of the *Mycobacterium* complex.

TABLE 3

| MYCOBACTERIUM | MARKERS | | |
|---|---|---|---|
| STRAIN | RD4 | RD9 | TBD1 |
| *M. bovis* BCG | − | − | + |
| *M. bovis* | − | − | + |
| *M. africanum* | + | − | + |
| *M. tuberculosis* | + | + | − |
| *M. tuberculosis* ancestral | + | + | + |
| *M. canettii* | + | + | + |

Beside TbD1 marker, preferably at least 2 other markers should be used. Examples of such additional markers available in the literature are listed in the following table 1. Although ancestral strains of *Mycobacterium tuberculosis* represent only 5% of all *Mycobacterium tuberculosis* strains, persons who would be interested in distinguishing the ancestral strains of *Mycobacterium tuberculosis* from the strains of *Mycobacterium canettii*, could consider using the genetic marker RD12 in combination with the three markers described in table 3. Because the region $RD^{can}$ partially overlapped RD12 in genome of *Mycobacterium canettii*, flanking primers as described in table 1 do not hybridize on genomic DNA of *Mycobacterium canettii*. Therefore, PCR amplification with these flanking primers results in 2.8 kb PCR product in *Mycobacterium tuberculosis* and no PCR product in *Mycobacterium canettii*.

An other way to distinguish ancestral strains of *Mycobacterium tuberculosis* from *Mycobacterium canettii* would be the detection of the insertion element specific for *M. canettii* strains and corresponding to SEQ ID No 19.

Supplemental Data:

TABLE 1

RD, RvD and TbD1 regions and selected primers

| Region absent from BCG | Gene | Size (kb) | Internal Primerpair | Flanking primers or $2^{nd}$ internal * primerpair |
|---|---|---|---|---|
| RD1 | Rv3871-Rv3879c | 9.5 | RD1in-Rv3878F GTC AGC CAA GTC AGG CTA CC (SEQ ID NO: 25) RD1in-Rv3878R CAA CGT TGT GGT TGT TGA GG (SEQ ID NO: 27) | RD1-flank.left GAA ACA GTC CCC AGC AGG T (SEQ ID NO: 26) RD1-flank.right TTC AAC GGG TTA CTG CGA AT (SEQ ID NO: 28) |
| RD2 | Rv1978-Rv1988 | 10.8 | RD2-Rv1979.int.F TAT AGC TCT CGG CAG GTT CC (SEQ ID NO: 29) RD2-Rv1979-int.R ATC GGC ATC TAT GTC GGT GT (SEQ ID NO: 31) | RD2-flank.F CTC GAC CGC GAC GAT GTG C (SEQ ID NO: 30) RD2-flank.R CCT CGT TGT CAC CGC GTA TG (SEQ ID NO: 32) |

TABLE 1-continued

RD, RvD and TbD1 regions and selected primers

| Region absent from BCG | Gene | Size (kb) | Internal Primerpair | Flanking primers or $2^{nd}$ internal * primerpair |
|---|---|---|---|---|
| RD3* | Rv1573-Rv1586c | 9.2 | RD3-Rv1586.int.F<br>TTA TCT TGG CGT TGA CGA TG<br>(SEQ ID NO: 33)<br>RD3-Rv1586.int.R<br>CAT ATA AGG GTG CCC GCT AC<br>(SEQ ID NO: 35) | RD3.int-REP.F<br>CTG ACG TCG TTG TCG AGG TA*<br>(SEQ ID NO: 34)<br>RD3-int-REP.R<br>GTA CCC CCA GGC GAT CTT*<br>(SEQ ID NO: 36) |
| RD4 | Rv1505c-Rv1516c | 12.7 | RD4-Rv1516.int.F<br>CAA GGG GTA TGA GGT TCA CG<br>(SEQ ID NO: 37)<br>RD4-Rv1516.int.R<br>CGG TGA TTC GTG ATT GAA CA<br>(SEQ ID NO: 39) | RD4-flank.F<br>CTC GTC GAA GGC CAC TAA AG<br>(SEQ ID NO: 38)<br>RD4-flank.R<br>AAG GCG AAC AGA TTC AGC AT<br>(SEQ ID NO: 40) |
| RD5* | Rv2346c-Rv2353c | 9.0 | RD5A-Rv2348.int.F<br>AAT CAC GCT GCT GCT ACT CC<br>(SEQ ID NO: 41)<br>RD5A-Rv2348.int.R<br>GTG CTT TTG CCT CTT GGT C<br>(SEQ ID NO: 43) | RD5B-plcA.int.F<br>CAA GTT GGG TCT GGT CGA AT<br>(SEQ ID NO: 42)<br>RDSB-plcA.int.R<br>GCT ACC CAA GGT CTC CTG GT<br>(SEQ ID NO: 44) |
| RD6* | Rv3425-Rv3428c | 4.9 | RD6-IS1532F<br>CAG CTG GTG AGT TCA AAT GC<br>(SEQ ID NO: 45)<br>RD6-IS1532R<br>CTC CCG ACA CCT GTT CGT<br>(SEQ ID NO: 46) | ND<br><br><br>ND |
| RD7 | Rv1964-Rv1977 | 12.7 | RD7-Rv1976.int.F<br>TGG ATT GTC GAC GGT ATG AA<br>(SEQ ID NO: 47)<br>RD7-Rv1976.int.R<br>GGT CGA TAA GGT CAC GGA AC<br>(SEQ ID NO: 49) | RD7-flank.F<br>GGT AAT CGT GGC CGA CAA G<br>(SEQ ID NO: 48)<br>RD7-flank.R<br>CAG CTC TTC CCC TCT CGA C<br>(SEQ ID NO: 50) |
| RD8 | ephA-lpqG | 5.9 | RD8-ephA.F<br>GGT GTG ATT TGG TGA GAC GAT G<br>(SEQ ID NO: 51)<br>RD8-ephA.R<br>AGT TCC TCC TGA CTA ATC CAG GC<br>(SEQ ID NO: 53) | RD8-flank.F<br>CAA TCA GGG CTG TGC TAA CC<br>(SEQ ID NO: 52)<br>RD8-flank.R<br>CGA CAG TTG TTG TGC GTA CTG GT<br>(SEQ ID NO: 54) |
| RD9 | cobL-Rv2075 | 2.0 | RD9-intF<br>CGA TGG TCA ACA CCA CTA CG<br>(SEQ ID NO: 55)<br>RD9-intR<br>CTG GAC CTC GAT GAC CAC TC<br>(SEQ ID NO: 57) | RD9-flankF<br>GTG TAG GTC AGC CCC ATC C<br>(SEQ ID NO: 56)<br>RD9-flankR<br>GCC CAA CAG CTC GAC ATC<br>(SEQ ID NO: 58) |
| RD10 | Rv0221-Rv0223 | 1.9 | RD10-intF<br>GTA ACC GCT TCA CCG GAA T<br>(SEQ ID NO: 59)<br>RD10-intR<br>GTC AAC TCC ACG GAA AGA CC<br>(SEQ ID NO: 61) | RD10-flankF<br>CTG CAA CCA TCC GGT ACA C<br>(SEQ ID NO: 60)<br>RD10-flankR<br>GTC ATG AAC GCC GGA CAG<br>(SEQ ID NO: 62) |
| RD11 | Rv2645-Rv2695c | 11.0 | RD11-Rv2646F<br>CGG CAG CTA GAC GAC CTC<br>(SEQ ID NO: 63)<br>RD11-Rv2646R<br>AAC GTG CTG CGA TAG GTT TT<br>(SEQ ID NO: 65) | RD11-fla-F<br>TCA CAT AGG GGC TGC GAT AG<br>(SEQ ID NO: 64)<br>RD11-fla-R<br>AGA GGA ACC TTT CGG TGG TT<br>(SEQ ID NO: 66) |
| RD12 | sseC-Rv3121 | 2.8 | RD12-Rv3120.int.F<br>GAA ATA CGA GTG CGC TGA CC<br>(SEQ ID NO: 67)<br>RD12-Rv3120.int.R<br>CTC TGA ACC ATC GGT GTC G<br>(SEQ ID NO: 69) | RD12.flank.F<br>GCC ATC AAC GTC AAG AAC CT<br>(SEQ ID NO: 68)<br>RD12-flank.R<br>CGG CCA GGT AAC AAG GAG T<br>(SEQ ID NO: 70) |
| RD13 | Rv1255C-Rv1257c | 3.0 | RD13intF<br>GGA TGT CAC TCG GAA CGG CA<br>(SEQ ID NO: 71)<br>RD13intR | RD13.flank.F<br>CGA TGG TGT TTC TTG GTG AG<br>(SEQ ID NO: 72)<br>RD13-flank.R |

TABLE 1-continued

| RD, RvD and TbD1 regions and selected primers | | | | |
|---|---|---|---|---|
| Region absent from BCG | Gene | Size (kb) | Internal Primerpair | Flanking primers or $2^{nd}$ internal * primerpair |
| | | | CAC CGG GCT GAT CGA GCG A (SEQ ID NO: 73) | GGA TCG GCT CAG TGA ATA CC (SEQ ID NO: 74) |
| RD14 | Rv1765c-Rv1773c | 9.0 | RD14-Rv1769.int.F GTG GAG CAC CTT GAC CTG AT (SEQ ID NO: 75) RD14-Rv1769.int.R CGT CGA ATA CGA GTC GAA CA (SEQ ID NO: 77) | RD14-flankF TTG ATT CGC CAA CAA CTG AA (SEQ ID NO: 76) RD14-flankR GGG CTG GTT AGT GTC GAT TC (SEQ ID NO: 78) |
| Region missing from *M. tuberculosis* H37Rv | | | | |
| RvD1* | | 5.0 | RvD1-int1F AGC GCG TCG AAC ACC GGC (SEQ ID NO: 79) RvD1-int1R CCT GAA TCC GCG CAA TTC CAT (SEQ ID NO: 81) | RvD1-int2.F GAG CCA CTC CGA TGT TGA CT (SEQ ID NO: 80) RvD1-int2.R CAC GCG AAC CCT ACC TAC AT (SEQ ID NO: 82) |
| RvD2* | plcD | 5.1 | RvD2-int1F GTT CTC CTG TCG AAC CTC CA (SEQ ID NO: 83) RvD2-int1R ACT TCA CCG GTT TCA TCT CG (SEQ ID NO: 85) | RvD2-int2F GGA CGG TGA CGG TAT TTG TC (SEQ ID NO: 84) RvD2-int2R TCG CCA ACT TCT ATG GAC CT (SEQ ID NO: 86) |
| RvD3 | | 1.0 | RvD3-intF ATC GAT CAG GTC GTC AAT GC (SEQ ID NO: 87) RvD3-intR ACG CCA CCA TCA AGA TCC (SEQ ID NO: 89) | RvD3-flank.F AAA CCA TGC AGC GTC TGC CA (SEQ ID NO: 88) RvD3-flankR GCG TTT CTG CGT CTG GTT GA (SEQ ID NO: 90) |
| RvD4* | PPE gene | 0.8 | RvD4-intF-PPE GGT TGC CAA CGT TAC CGA TGC (SEQ ID NO: 91) RvD4-intR-PPE CCG GTG GTG GTG GCG GCT (SEQ ID NO: 92) | ND ND |
| RvD5 | moa | 4.0 | RvD5intF GGG TTC ACG TTC ATT ACT GTT C (SEQ ID NO: 93) RvD5intR CCT GCG CTT ATC TCT AGC GG (SEQ ID NO: 95) | RvD5-flankF CCC ATC GTG GTC GTT CAC C (SEQ ID NO: 94) RvD5-flankR CCC ATC GTG GTC GTT CAC C (SEQ ID NO: 96) |
| TbD1 | mmpL6 | 2.1 | TBD1intS.R CGT TCA ACC CCA AAC AGG TA (SEQ ID NO: 97) TBD1intS.R AAT CGA ACT CGT GGA ACA CC (SEQ ID NO: 99) | TBD1fla1-R CTA CCT CAT CTT CCG GTC CA (SEQ ID NO: 98) TBD1fla1-R CAT AGA TCC CGG ACA TGG TG (SEQ ID NO: 100) |
| katG, gyrA, oxyR', pncA and mmpL6 PCR and sequencing primers | | | | |
| katG[463] | | | katG-2154,225-PCR-F CTA CCA GCA CCG TCA TCT CA (SEQ ID NO: 101) katG-2155,157-PCR-R AGG TCG TAT GGA CGAACA CC (SEQ ID NO: 103) | katG-2154,872-SEQ-R ACA AGC TGA TCC ACC GAG AC (SEQ ID NO: 102) |
| gyrA[95] | | | gyrA-7,127-PCR-F GTT CGT GTG TTG CGT CAA GT (SEQ ID NO: 104) gyrA-8,312-PCR-R CAG CTG GGT GTG CTT GTA AA (SEQ ID NO: 106) | gyrA-7,461F CGG GTG CTC TAT GCA ATG TT (SEQ ID NO: 105) |
| oxyR'[285] | | | oxyR 2725,559F TAT GCG ATC AGG CGT ACT TG (SEQ ID NO: 107) oxyR-2726,024-PCR-R | oxyR-2726,024-SEQ-R CAA AGC AGT GGT TCA GCA GT (SEQ ID NO: 108) |

TABLE 1-continued

RD, RvD and TbD1 regions and selected primers

| Region absent from BCG | Gene | Size (kb) | Internal Primerpair | Flanking primers or 2nd internal * primerpair |
|---|---|---|---|---|
| | | | CAA AGC AGT GGT TCA GCA GT (SEQ ID NO: 109) | |
| pncA[57] | | | pncA-2288,678-PCR-F ATC AGG AGC TGC AAA CCA AC (SEQ ID NO: 110) pncA-2289,319-PCR-R GGC GTC ATG GAC CCT ATA TC (SEQ ID NO: 112) | pncA-2289,319-SEQ-R GGC GTC ATG GAC CCT ATA TC (SEQ ID NO: 111) |
| mmpL6[551] | | | mmpL-seq5F GTA TCA GAG GGA CCG AGC AG (SEQ ID NO: 113) TBD1fla1-R CAT AGA TCC CGG ACA TGG TG (SEQ ID NO: 115) | mmpL-seq5F GTA TCA GAG GGA CCG AGC AG (SEQ ID NO: 114) |

The RD nomenclature used in this table is based on that used by Brosch et al. (2000), (Ref. 25) and differs from that proposed by Behr and coworkers (1999), (Ref. 6). Primer sequences are shown in 5'→3' direction.
*Regions where a second pair of internal primers was used rather than flanking primers, due to flanking repetitive regions, andlor mobile genetic elements.

REFERENCES

1. Boddinghaus, B., Rogall, T., Flohr, T., Blocker, H. & Bottger, E. C. (1990) *J Clin Microbiol* 28, 1751-9.
2. Sreevatsan, S., Pan, X., Stockbauer, K. E., Connell, N. D., Kreiswirth, B. N., Whittam, T. S. & Musser, J. M. (1997) *Proc Natl Acad Sci USA* 94, 9869-74.
3. Stead, W. W., Eisenach, K. D., Cave, M. D., Beggs, M. L., Templeton, G. L., Thoen, C. O. & Bates, J. H. (1995) *Am J Respir Crit Care Med* 151, 1267-8.
4. Cole, S. T., Brosch, R., Parkhill, J., Gamier, T., Churcher, C., Harris, D., Gordon, S. V., Eiglmeier, K., Gas, S., Barry, C. E., 3rd, Tekaia, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K., Barrell, B. G. & et al. (1998) *Nature* 393, 537-44.
5. Gordon, S. V., Broscb, R., Billault, A., Garnier, T., Eiglmeier, K. & Cole, S. T. (1999) *Mol Microbiol* 32, 643-55.
6. Behr, M. A., Wilson, M. A., Gill, W. P., Salamon, H., Schoolnik, G. K., Rane, S. & Small, P. M. (1999) *Science* 284, 1520-3.
7. Brosch, R., Philipp, W. J., Stavropoulos, E., Colston, M. J., Cole, S. T. & Gordon, S. V. (1999) *Infect Immun* 67, 5768-74.
8. Kreiner, K., van Soolingen, D., Frothingham, R., Haas, W. H., Hermans, P. W., Martin, C., Palittapongarnpim, P., Plikaytis, B. B., Riley, L. W., Yakrus, M. A., Musser, J. M. & van Embden, J. D. (1999) *J Clin Microbiol* 37, 2607-18.
9. Supply, P., Lesjean, S., Savine, E., Kremer, K., van Soolingen, D., & Locht, C. (2001) *J Clin Microbiol* 39, 3563-71.
10. Van Soolingen, D., de Haas, P. E. W., Hermans, P. W. M. & van Embden, J. D. A. (1994) *Methods Enzymol* 235, 196-205.
11. Heym, B., Honore, N., Truffot-Pernot, C., Banerjee, A., Schurra, C., Jacobs, W. R., Jr., van Embden, J. D., Grosset, J. H. & Cole, S. T. (1994) *Lancet* 344, 293-8.
12. Scorpio, A., Collins, D., Whipple, D., Cave, D., Bates, J. & Zhang, Y. (1997) *J Clin Microbiol* 35, 106-10.
13. Sreevatsan, S., Escalante, P., Pan, X., Gillies, D. A., 2nd, Siddiqui, S., Khalaf, C. N., Kreiswirth, B. N., Bifani, P., Adams, L. G., Ficht, T., Perumaalla, V. S., Cave, M. D., van Embden, J. D. & Musser, J. M. (1996) *J Clin Microbiol* 34, 2007-10.
14. Van Embden, J. D., van Gorkom, T., Kremer, K., Jansen, R., van Der Zeijst, B. A. & Schouls, L. M. (2000) *J Bacteriol* 182, 2393-401.
15. Van Soolingen, D., Hoogenboezem, T., de Haas, P. E., Hermans, P. W., Koedam, M. A., Teppema, K. S., Brennan, P. J., Besra, G. S., Portaels, F., Top, J., Schouls, L. M. & Van Embden, J. D. (1997) *Int J Syst Bacteriol* 47, 1236-45.
16. Papa, F., Laszlo, A., David, H. L. & Daffe, M. (1989) *Acta Leprol* 7 (Suppl.) 98-101.
17. Wells, A. Q., (1937) *Lancet* 1221.
18. Van Soolingen, D., Van der Zanden, A. G., de Haas, P. E., Noordhoek, G. T., Kiers, A., Foudraine, N. A., Portaels, F., Kolk, A. H., Kremer, K. & Van Embden, J. D. (1998) *J Clin Microbiol* 36, 1840-5.
19. Brodin, P., et al. (2002) in preparation
20. Aranaz, A., Liebana, E., Gomez-Mampaso, E., Galan, J. C., Cousins, D., Ortega, A., Blazquez, J., Baquero, F., Mateos, A., Suarez, G. & Dominguez, L. (1999) *Int J Syst Bacteriol* 49, 1263-73.
21. Van Soolingen, D., P. E. W. de Haas, J. Haagsma, T. Eger, P. W. M. Hermans, V. Ritacco, A. Alito, & J. D. A van Embden. (1994) *J. Clin. Microbiol.* 32, 2425-33.
22. Samper, S., Martin, C., Pinedo, A., Rivero, A., Blazquez, 3., Baquero, F., van Soolingen, D. & Van Embden, J. (1997) *Aids* 11, 1237-42.
23. Mahairas, G. G., Sabo, P. J., Hickey, M. J., Singh, D. C. & Stover, C. K. (1996) *J Bacteriol* 178, 1274-82.
24. Gordon, S. V., Eiglmeier, K., Garnier, T., Brosch, R., Parkhill, J., Barrell, B., Cole, S. T. & Hewinson, R. G. (2001) *Tuberculosis* 81, 157-63.
25. Brosch, R., S. V. Gordon, K. Eiglmeier, T. Garnier, F. Tekaia, E. Yeramanian, & S. T. Cole. (1999) in Molecular genetics of mycobacteria, eds. Hatful G. F. & Jacobs, W. R. Jr. (American Society for Microbiology, Washington, D.C.), pp. 19-36.
26. Radhakrishnan, I., K, M. Y., Kumar, R. A. & Mundayoor, S. (2001) *J Clin Microbiol* 39, 1683.

27. Fletcher, H. A., Donoghue, H. D., Holton, J., Pap, I. & Spigelman, M. (2002) *Am. J. Phys. Anthropol*, in press.

28. Mays, S., Taylor, G. M., Legge, A. J., Young, D. B. & Turner-Walker, G. (2001) Am J Phys Anthropol 114, 298-311.

29. Nerlich, A. G., Haas, C. J., Zink, A., Szeimies, U. & Hagedorn, H. G. (1997) *Lancet* 350, 1404.

30. Salo, W. L., Aufderheide, A. C., Buikstra, J. & Holcomb, T. A. (1994) *Proc Natl Acad Sci USA* 91, 2091-4.

31. Rothschild, B. M., Martin, L. D., Lev, G., Bercovier, H., Bar-Gal, G. K., Greenblatt, C., Donoghue, H., Spigelman, M. & Brittain, D. (2001) *Clin Infect Dis* 33, 305-11.

32. Parsons, L. M., Brosch, R., Cole, S. T., Somoskovi, A., Loder, A., Britzel, G., van Soolingen, D., Hale, Y., & Salfinger, M. (2001) in preparation

---

The invention claimed is:

1. An isolated or purified nucleic acid, wherein said nucleic acid is selected from the group consisting of:

a. SEQ ID NO:1; and b. Nucleic acid having a sequence fully complementary to SEQ ID NO:1.

2. The purified or isolated nucleic acid fragment, obtained by PCR amplification of a nucleic acid from *Mycobacterium* complex with the pair of primers SEQ ID NO:17 and SEQ ID NO:18.

3. A nucleic acid selected from the group consisting of:

a. SEQ ID NO:4; and b. Nucleic acid having a sequence fully complementary to SEQ ID NO:4.

4. A purified or isolated nucleic acid comprising up to 2000 consecutive nucleotides of SEQ ID NO:4 or its complement, said nucleic acid obtained by PCR amplification of a nucleic acid from *Mycobacterium* complex with one pair of primers chosen from the group consisting of: SEQ ID NO:13, SEQ ID NO:14, SEQ ID NO:15, and SEQ ID NO:16.

5. The purified or isolated nucleic acid according to claim 4, wherein it is obtained by PCR amplification of a nucleic acid from *Mycobacterium* complex with the pair of primers SEQ ID NO:13 and SEQ ID NO:14.

6. The purified or isolated nucleic acid according to claim 4, wherein it is obtained by PCR amplification of a nucleic acid from *Mycobacterium* complex with the pair of primers SEQ ID NO:15 and SEQ ID NO:16.

7. A recombinant vector comprising a nucleic acid selected among nucleic acids according to any of claims 1, 2, 3, 4, 5, and 6.

8. The recombinant vector of claim 7 consisting of vector named X229 included in the recombinant *Escherichia coli* deposited at the CNCM on Feb. 18, 2002 under NO: I-2799.

9. A recombinant cell which is the *Escherichia coli* deposited at the CNCM on Feb. 18, 2002 under NO: I-2799.

10. A method for the discriminatory detection and identification of:

*Mycobacterium tuberculosis* except *Mycobacterium tuberculosis* strains having the sequence CTG at codon 463 of gene katG and having no or very few IS6110 sequences inserted in their genome; versus,

*Mycobacterium africanum, Mycobacterium canetti, Mycobacterium microti, Mycobacterium bovis, Mycobacterium bovis* BCG in a biological sample, comprising the following steps:

a) isolating DNA from the biological sample to be analyzed or producing a cDNA from the RNA of the biological sample, b) detecting SEQ ID NO: 1 or SEQ ID NO: 4, or both SEQ ID NO:1 and SEQ ID NO:4 nucleic acid in said biological sample, wherein the presence of SEQ ID NO:1 or SEQ ID NO: 4 is indicative of *Mycobacterium africanum, Mycobacterium canetti, Mycobacterium microti, Mycobacterium bovis, Mycobacterium bovis* BCG or *Mycobacterium tuberculosis* strains having the sequence CTG at codon 463 of gene katG and having no or very few IS6110 sequences in the biological sample.

11. The method as claimed in claim 10, wherein the detection of the mycobacterial DNA sequences is carried out using nucleotide sequences complementary to said DNA sequences.

12. The method as claimed in claim 10, wherein the detection of the mycobacterial DNA sequences is carried out by amplification of these sequences using primers.

13. The method as claimed in claim 12, wherein the primers have a nucleotide sequence chosen from the group consisting of: SEQ ID NO:13, SEQ ID NO:14, SEQ ID NO:15, SEQ ID NO:16, SEQ ID NO:17, or SEQ ID NO:18.

14. An in vitro method for the detection and identification of *Mycobacteria* from the *Mycobacterium* complex in a biological sample, comprising the following steps:

a. isolating DNA from the biological sample to be analyzed or producing cDNA from the RNA of the biological sample;

b. detecting SEQ ID NO:1 or SEQ ID NO:4, or both SEQ ID NO:1 and SEQ ID NO:4; and c. detecting at least one additional genetic marker selected among RD1, RD2, RD3, RD4, RD5, RD6, RD7, RD8, RD9, RD10, RD11, RD13, RD14, RvD1, RvD2, RvD3, RvD4, RvD5, katG463, gyrA95, oxyR'285, pncA57, and $mmpL6^{551}$, the specific insertion element of *M. canettii*.

15. The in vitro method of claim 14 wherein two additional markers selected from RD4 and RD9 are used.

16. The in vitro method of claim 14 wherein three additional markers selected from RD4, RD9, and RD12 are used.

17. A nucleic acid consisting of at least 30 consecutive nucleotides of SEQ ID NO:1, or its complement; or SEQ ID NO:4, or its complement.

18. The nucleic acid according to claim 17, wherein the fragment comprises at least 50 consecutive nucleotides of SEQ ID NO:1, or its complement; or SEQ ID NO:4, or its complement.

19. The nucleic acid according to claim 17, wherein the fragment comprises at least 100 consecutive nucleotides of SEQ ID NO:1, or its complement; or SEQ ID NO:4, or its complement.

20. The nucleic acid according to claim 17, wherein the fragment comprises at least 250 consecutive nucleotides of SEQ ID NO:1, or its complement; or SEQ ID NO:4, or its complement.

* * * * *